US010724097B2

(12) United States Patent
Patel

(10) Patent No.: US 10,724,097 B2
(45) Date of Patent: Jul. 28, 2020

(54) METHODS AND COMPOSITIONS FOR DIAGNOSIS AND MANAGEMENT OF DIABETES AND METABOLIC SYNDROME

(71) Applicants: University of South Florida, Tampa, FL (US); THE U.S. GOVERNMENT AS REPRESENTED BY THE DEPARTMENT OF VETERANS AFFAIRS OFFICE OF GENERAL COUNSEL, Washington, DC (US)

(72) Inventor: Niketa A. Patel, Land O'Lakes, FL (US)

(73) Assignees: University of South Florida, Tampa, FL (US); The United States Government as Represented by the Department of Veterans Affairs Office of General Counsel, Washington, DC (US)

( * ) Notice: Subject to any disclaimer, the term of this patent is extended or adjusted under 35 U.S.C. 154(b) by 199 days.

(21) Appl. No.: 15/528,894

(22) PCT Filed: Nov. 30, 2015

(86) PCT No.: PCT/US2015/062912
§ 371 (c)(1),
(2) Date: May 23, 2017

(87) PCT Pub. No.: WO2016/089732
PCT Pub. Date: Jun. 9, 2016

(65) Prior Publication Data
US 2017/0321277 A1 Nov. 9, 2017

Related U.S. Application Data

(60) Provisional application No. 62/086,052, filed on Dec. 1, 2014.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/158* (2013.01); *C12Q 2600/178* (2013.01); *G01N 2800/042* (2013.01)

(58) Field of Classification Search
None
See application file for complete search history.

(56) References Cited

U.S. PATENT DOCUMENTS

| 6,716,234 B2 | 4/2004 | Grafton et al. |
| 8,163,691 B2 | 4/2012 | Durden |
| 2003/0088270 A1 | 5/2003 | Lubbers et al. |
| 2008/0262544 A1 | 10/2008 | Burkhart |
| 2008/0319478 A1 | 12/2008 | Foerster et al. |
| 2014/0162888 A1 | 6/2014 | Kuslich et al. |

FOREIGN PATENT DOCUMENTS

| WO | 2007034527 A2 | 3/2007 |
| WO | 2014160032 A1 | 10/2014 |

OTHER PUBLICATIONS

Lee et al; Diabetologia, vol. 48, pp. 1776-1783; 2005.*
Fragouli et al; European Society for Paediatric Endocrinology, Sep. 20-22, 2014.*
International Search Report for PCT/US2015/062912 dated Jun. 9, 2016.
Carter, Gay, et al. "Circulating long noncoding RNA GAS5 levels are correlated to prevalence of type 2 diabetes mellitus." BBA clinical 4 (2015): 102-107.
Arthrex, TightRope Syndesmosis Fixation, 2007, pp. 1-6.
Carter, Gay, et al. "Dysregulated alternative splicing pattern of PKC during differentiation of human preadipocytes represents distinct differences between lean and obese adipocytes." ISRN obesity 2013 (2013).
Hamdorf, Matthias, et al. "PKCδ-Induced PU. 1 Phosphorylation Promotes Hematopoietic Stem Cell Differentiation to Dendritic Cells." Stem cells 29.2 (2011): 297-306.
Lee, Hyo-Jong, et al. "PKC-δ inhibitors sustain self-renewal of mouse embryonic stem cells under hypoxia in vitro." Experimental & molecular medicine 42.4 (2010): 294.
Watson, James E., et al. "Comparison of markers and functional attributes of human adipose-derived stem cells and dedifferentiated adipocyte cells from subcutaneous fat of an obese diabetic donor." Advances in wound care 3.3 (2014): 219-228.
Katakura, Yoshinori, et al. "Protein kinase C δ plays a key role in cellular senescence programs of human normal diploid cells." Journal of biochemistry 146.1 (2009): 87-93.
Bortolotto, Josiane W., et al. "Higher content of trans fatty acids in abdominal visceral fat of morbidly obese individuals undergoing bariatric surgery compared to non-obese subjects." Obesity surgery 15.9 (2005): 1265-1270.
Caserta, Frank, et al. "Fat depot origin affects fatty acid handling in cultured rat and human preadipocytes." American Journal of Physiology-Endocrinology and Metabolism 280.2 (2001): E238-E247.
Baglioni, Silvana, et al. "Functional differences in visceral and subcutaneous fat pads originate from differences in the adipose stem cell." PLoS one 7.5 (2012): e36569.
Dusserre, Eric, Philippe Moulin, and Hubert Vidal. "Differences in mRNA expression of the proteins secreted by the adipocytes in human subcutaneous and visceral adipose tissues." Biochimica et Biophysica Acta (BBA)-Molecular Basis of Disease 1500.1 (2000): 88-96.
Oñate, Blanca, et al. "Stem cells isolated from adipose tissue of obese patients show changes in their transcriptomic profile that indicate loss in stemcellness and increased commitment to an adipocyte-like phenotype." BMC genomics 14.1 (2013): 625.

(Continued)

Primary Examiner — Jehanne S Sitton
(74) Attorney, Agent, or Firm — Thomas|Horstemeyer, LLP

(57) ABSTRACT

Described herein are assays, methods, and devices for diagnosing/prognosing diabetes, metabolic syndrome, pre-diabetic state and/or the early-onset of diabetes in a subject. The assays, methods, and devices described herein can be configured to detect one or more long-coding RNAs in a sample from a subject.

5 Claims, 9 Drawing Sheets

Specification includes a Sequence Listing.

(56) References Cited

OTHER PUBLICATIONS

Zubiri, Irene, Fernando Vivanco, and Gloria Alvarez-Llamas. "Proteomic analysis of urinary exosomes in cardiovascular and associated kidney diseases by two-dimensional electrophoresis and LC-MS/MS." Vascular Proteomics. Humana Press, Totowa, NJ, 2013. 209-220.
Schageman, Jeoffrey, et al. "The complete exosome workflow solution: from isolation to characterization of RNA cargo." BioMed research international 2013 (2013).
Karastergiou, Kalypso, et al. "Distinct developmental signatures of human abdominal and gluteal subcutaneous adipose tissue depots." The journal of Clinical Endocrinology & Metabolism 98.1 (2013): 362-371.
Shen, Xiao, et al. "Adipose-derived stem cells promote human dermal fibroblast function and increase senescence-associated β-galactosidase mRNA expression through paracrine effects." Molecular medicine reports 10.6 (2014): 3068-3072.
Mantovani, Cristina, Giorgio Terenghi, and Valerio Magnaghi. "Senescence in adipose-derived stem cells and its implications in nerve regeneration." Neural regeneration research 9.1 (2014): 10.
Jun, Hee-Sook, et al. "Effect of cell senescence on the impedance measurement of adipose tissue-derived stem cells." Enzyme and microbial technology 53.5 (2013): 302-306.
Markowski, Dominique Nadine, et al. "HMGA2 expression in white adipose tissue linking cellular senescence with diabetes." Genes & nutrition 8.5 (2013): 449.
Abdelmohsen, Kotb, et al. "Senescence-associated lncRNAs: senescence-associated long noncoding RNAs." Aging cell 125 (2013): 890-900.
Byun, H-O., et al. "PKCδ phosphorylation is an upstream event of GSK3 inactivation-mediated ROS generation in TGF-β1-induced senescence." Free radical research 48.9 (2014): 1100-1108.
Patel, Rekha S., et al. "Transformer 2 beta homolog (Drosophila)(TRA2B) regulates Protein Kinase C deltaI (PKCδI) splice variant expression during 3T3L1 pre-adipocyte cell cycle." Journal of Biological Chemistry (2014): jbc-M114.
Colosia, Ann D., Roberto Palencia, and Shahnaz Khan. "Prevalence of hypertension and obesity in patients with type 2 diabetes mellitus in observational studies: a systematic literature review." Diabetes, metabolic syndrome and obesity: targets and therapy 6 (2013): 327.
Raj, Srilakshmi M., et al. "Variation at Diabetes-and Obesity-Associated Loci May Mirror Neutral Patterns of Human Population Diversity and Diabetes Prevalence in India." Annals of human genetics 77.5 (2013): 392-408.
Sundborn, Gerhard, et al. "Overweight and obesity prevalence among adult Pacific peoples and Europeans in the Diabetes Heart and Health Study (DHAHS) 2002-2003, Auckland New Zealand." NZ Med J 123 (2010).
Crawford, Albert G., et al. "Prevalence of obesity, type II diabetes mellitus, hyperlipidemia, and hypertension in the United States: findings from the GE Centricity Electronic Medical Record database." Population health management 13.3 (2010): 151-161.
Xu, X. Julia, et al. "What distinguishes adipose tissue of severely obese humans who are insulin sensitive and resistant?." Current opinion in lipidology 24.1 (2013): 49.
Chen, Xing, and Gui-Ying Yan. "Novel human lncRNA—disease association inference based on lncRNA expression profiles." Bioinformatics 29.20 (2013): 2617-2624.
Arase, Mayu, et al. "Transforming growth factor-β-induced lnc RNA-Smad7 inhibits apoptosis of mouse breast cancer Jyg MC (A) cells." Cancer science 105.8 (2014): 974-982.
Liu, Qian, et al. "LncRNA loc285194 is a p53-regulated tumor suppressor." Nucleic acids research 41.9 (2013): 4976-4987.
International Human Genome Sequencing Consortium. "Initial sequencing and analysis of the human genome." Nature 409.6822 (2001): 860.
Williams, Gwyn T., Mirna Mourtada-Maarabouni, and Farzin Farzaneh. "A critical role for non-coding RNA GAS5 in growth arrest and rapamycin inhibition in human T-lymphocytes." (2011): 482-486.
Budczies, Jan, et al. "Cutoff Finder: a comprehensive and straightforward Web application enabling rapid biomarker cutoff optimization." PloS one 7.12 (2012): e51862.
Taneera, Jalal, et al. "Identification of novel genes for glucose metabolism based upon expression pattern in human islets and effect on insulin secretion and glycemia." Human molecular genetics 24.7 (2014): 1945-1955.
Fadista, João, et al. "Global genomic and transcriptomic analysis of human pancreatic islets reveals novel genes influencing glucose metabolism." Proceedings of the National Academy of Sciences 111.38 (2014): 13924-13929.
Ding, Guo-Lian, et al. "Transgenerational glucose intolerance with Igf2/H19 epigenetic alterations in mouse islet induced by intrauterine hyperglycemia." Diabetes (2012): DB_111314.
Pasmant, Eric, et al. "ANRIL, a long, noncoding RNA, is an unexpected major hotspot in GWAS." The FASEB Journal 25.2 (2011): 444-448.
Divoux, Adeline, et al. "Identification of a novel lncRNA in gluteal adipose tissue and evidence for its positive effect on preadipocyte differentiation." Obesity 22.8 (2014): 1781-1785.
Cooper, Denise R., et al. "Long non-coding RNA NEAT1 associates with SRp40 to temporally regulate PPARγ2 splicing during adipogenesis in 3T3-L1 cells." Genes 5.4 (2014): 1050-1063.
Yacqub-Usman, Kiren, Mark R. Pickard, and Gwyn T. Williams. "Reciprocal regulation of GAS5 lncRNA levels and mTOR inhibitor action in prostate cancer cells." The prostate 75.7 (2015): 693-705.
Pickard, Mark R., and Gwyn T. Williams. "Regulation of apoptosis by long non-coding RNA GAS5 in breast cancer cells: implications for chemotherapy." Breast cancer research and treatment 145.2 (2014): 359-370.
Pickard, M. R., M. Mourtada-Maarabouni, and G. T. Williams. "Long non-coding RNA GAS5 regulates apoptosis in prostate cancer cell lines." Biochimica et Biophysica Acta (BBA)-Molecular Basis of Disease 1832.10 (2013): 1613-1623.
Mourtada-Maarabouni, M., et al. "GAS5, a non-protein-coding RNA, controls apoptosis and is downregulated in breast cancer" Oncogene 28.2 (2009): 195.
Huang, Xiaoyi, et al. "Characterization of human plasma-derived exosomal RNAs by deep sequencing." BMC genomics 141 (2013): 319.
Tsui, Nancy BY, Enders KO Ng, and YM Dennis Lo. "Molecular analysis of circulating RNA in plasma." Clinical Applications of PCR. Humana Press, 2006. 123-134.
Wang, Kai, et al. "The spectrum of circulating RNA: a window into systems toxicology." toxicological sciences 132.2 (2013): 478-492.
Baraniskin, Alexander, et al. "Circulating U2 small nuclear RNA fragments as a novel diagnostic biomarker for pancreatic and colorectal adenocarcinoma." International journal of cancer 132.2 (2013): E48-E57.
Payne, R. E., et al. "Viable circulating tumour cell detection using multiplex RNA in situ hybridisation predicts progression-free survival in metastatic breast cancer patients." British journal of cancer 106.11 (2012): 1790.
Xie, Jianling, and Terence P. Herbert. "The role of mammalian target of rapamycin (mTOR) in the regulation of pancreatic β-cell mass: implications in the development of type-2 diabetes." Cellular and Molecular Life Sciences 69.8 (2012): 1289-1304.
Öst, Anita, et al. "Attenuated mTOR signaling and enhanced autophagy in adipocytes from obese patients with type 2 diabetes." Molecular medicine 16.7-8 (2010): 235.
Fraenkel, Merav, et al. "mTOR inhibition by rapamycin prevents β-cell adaptation to hyperglycemia and exacerbates the metabolic state in type 2 diabetes." Diabetes 57.4 (2008): 945-957.

* cited by examiner

SEQUENCE LISTING

<160> NUMBER OF SEQ ID NOS: 46

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
agctggaagt tgaaatgg                                                 18

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
caagccgact ctccatacc                                                19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tgacgtgccg cctggagaac                                               20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ccggcatcga aggtggaaga g                                             21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agatcttggt aaagcgaatg                                               20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
tggtgagaag ggtgagaa                                                 18

<210> SEQ ID NO 7
<211> LENGTH: 21
<212> TYPE: DNA
<213> ORGANISM: Artificial Sequence

```
<220> FEATURE:
<223> OTHER INFORMATION: primer

<400> SEQUENCE: 7
ccttccagaa acgtgatcca a                                              21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggccagcacg tgaagaagat                                                20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
agagctacaa tgagacgtgg c                                              21

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgatgtagag gtagcggggg                                                20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tctctccgta atggaagacc                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcattatgag acatccccac                                                20

<210> SEQ ID NO 13
<211> LENGTH: 324
<212> TYPE: DNA
<213> ORGANISM: Artificial Sequence
<220> FEATURE:
<223> OTHER INFORMATION: 21A

<400> SEQUENCE: 13
aaatagttga ccaagtgtgg tggctcacgt agtcccagca ctttgggagg ctgaggcagg    60
```

```
aggatcactt gagcccagga atttgagacc agcttgggca acatagtgag acctcatctc     120
ttaaaaaaaa aaattagctg ggtgtggtag tgcacacctg tggtcccagc tactttagag     180
gctgaggtag aggattgctt gagcctggga agttggggct gtagtgagct ttgattgcat     240
cactgcactc cagcctgggt gacagagcaa gaccctgtct ctaaaaaatt aaataaataa     300
taaaaaaatt aaaaagtaac tccc                                            324

<210> SEQ ID NO 14
<211> LENGTH: 299
<212> TYPE: DNA
<213> ORGANISM: Artificial Sequence
<220> FEATURE:
<223> OTHER INFORMATION: 7sl

<400> SEQUENCE: 14
gccgggcgcg gtggcgcgtg cctgtagtcc cagctactcg ggaggctgag gctggaggat      60
cgcttgagtc caggagttct gggctgtagt gcgctatgcc gatcgggtgt ccgcactaag     120
ttcggcatca atatggtgac ctcccggag cggggacca ccaggttgcc taaggagggg      180
tgaaccggcc caggtcggaa acggagcagg tcaaaactcc cgtgctgatc agtagtggga     240
tcgcgcctgt gaatagccac tgcactccag cctgggcaac atagcgagac cccgtctct     299

<210> SEQ ID NO 15
<211> LENGTH: 10156
<212> TYPE: DNA
<213> ORGANISM: Artificial Sequence
<220> FEATURE:
<223> OTHER INFORMATION: dlg2as

<400> SEQUENCE: 15
agacgggttg ataggtgcag tacaccacca tggcactta tacctgtata acaaccagc        60 acgttctgca catgtatccc acaaagtaa aaaataaat aaaatacatc tacatgttga     120
ataattttaa aaacaaaga cattaaaaaa agaaaattaa aaaatattg ttcacatatc      180 aatctccatt cctccacttc tcctcactaa ttactgacaa tatcccttca cctgtgtggg     240
tagaagaaaa attctagcag ttcaaatcct tggcctaaac catcattgct aaaatattca     300 cttttttaact tccaagaagt tagttaaatc atattctcac tcaaaataca agtaatttaa     360
atgagttttt atcagtgagt ttcttctgga ggctttgttt cttcattac tctcagcagc      420 atgtaagaag caatagggtg atactaaaat ggttttgtct aacctgaacg ctgtgtgtct     480
ggatcttcat tcactctgtg gaatctgtat tctatgaat tttaagtcct tttggcagga      540
aattgtaaag tgaacagaaa catgggtccc atgagacttc ttgtgccaaa acactatgca     600
ttatcctggt acctttaagt ccaaagagaa ttgtttaact tcttcattct taatattatg     660
ttgataacaa taacaaataa aggattctaa gctactcaca catgacatat aaattaaaga     720
gtgttttttg tcacccaaag tcaaaacaca aattaggata tttactctct tgcttccga      780 gggtgatttc tattgctgta gacaatttt agagaaaata aaagctttta attttaagtg      840
acctgatagt ctgatgttag ttatctctgt tgagcatttt ctgttgaaga taggctcact     900
ttatctttag gctatgaggt cttagtgtga tggatttgtc taaatgtaaa acaaacaaa      960 acaaaactat gctctctaag taaccactaa attctgttta taatagaag gctaaaaaat    1020 gaagggtgat atgctacttg gaattcaatt aaaaggaact aaaaaataaa ttataatatt    1080
atgcagaagc atcctcagat ctatttaagt atttcagctt tatagtccta aggaaattca    1140
aaagcagtga cagtaatggg tgaccattca atgtaacctt gattggacaa ctttgactat    1200
```

-continued

```
acaactaact tcagattaat ttttagtggg agttttttaaa ttgctctttg taaggtggac   1260
agtgatgtga gtggtccttt tagaagttttt ttttttcctg atctcaacca ctagtatatt   1320
ttattttcat tagcatatcc aggggataca gtagtgcctt cttatctgca gattctcttt   1380
ccacaatttc agttacttgt ggccaaccat ggctaaaaat attaaatgaa aaattacaac   1440
aataaacaat tcatcagttt tacattgtgt gccttttgag taacatgctg aaatcatgtg   1500
ctatcccact ctatgccaca aggaatgtaa aatgtccctt tgtccagggt attcacacta   1560
tataaactag ctgcccatta gccattaaca ttgtttgatc ctgacatcta accaacaaca   1620
tcatcatggc ttgaagatcc aggatcacct aaagctatgt cgcaatgcct gcatcactca   1680
cctcacttca tcttatcata caggcatttt gtcatctcat atcatcacaa gaaggttgag   1740
gactactgta aaatggaaag catatccatt aacctcacag agatcagtac cctggcaaag   1800
gttgtttgca tactggagga caaatatttt atcgtaaaga acttagaaaa ctttcaaaaa   1860
tgttttggaa acaatttaat gaaccagaat ttttttaagca tctaatgatt ttctggcatg   1920
cacaaaggta tgcacattag gaaagcaata cagaataatt ttttttaagag atggggtctt   1980 gctctgtcac ccaaggatag attgcagtgg catattcata gcttattgcg gcctcaaact   2040
cctgggctca agtgatcctc ctgcctcaac ctccaaagtg ttgggattac aggtgtgagg   2100
ccatgcctgg cctggaataa tgttttgtaa tggtttatag tatggaaatc agagttggaa   2160
ataatgactt taattctttg gtcctgcata ttactggctc tggatgtcca ggcaaccact   2220
tagttcctta aagcttcagt tttcatacct gcaaaatggg agattaaaat acccatctca   2280
tagggataaa tgtgtgtagc acagtacctg gtgcatagta ggtattcatg aaatgtggct   2340
cccgctataa gcaatgaaaa ccagcaccac cttaacattg acccttttag gatacaacgt   2400
tccaaggaaa agtttaattt tgcactggtt aaaggaattt caaatcatta ccaggggaaa   2460
agtgtaataa actgccaaga taactcaata atattgagtt attctcaata gatacacgaa   2520
ataatattct acttggaaat tcaattaaat aagctccaca aatgtttatt gaatgcccac   2580
tattcactag gtattgcatt gggttcagga gatttaaaca ttagttaaga cagggatctt   2640
gtttccatgg ggcttacaat ctcatgaggg agacagattc acaaacacaa aaatcccctta   2700 aaggagtttc aaagaagggg aggcaacagc ttaacctggg aaggtcagga aaagctttga   2760
agaatggata atactgaaat ataagctagg tttagttgta gagtgtaaca ggttttcttt   2820
atcatcaatc tctgtcaact gcctcatcct ctgccacaac cccaagatat tcctagagc    2880 tactttcaaa ttttcatgtg cttttgggga gcagaaaaga caatatgctt attgattatc   2940
atatttatag aagaaacaac aagatcattt tctttactgt tactcattgt ctaccaatct   3000
attatggtaa tgaatgagaa gaaaaaataa ggaagatgtt tagaggttat tttccttaaa   3060
gggagattcc acatcctgtg cctgccttgg aagccttgaa gaaaagacta tgcttaccca   3120
caaacatctc ttggcaccac tgtcaggttt gagtggacca cagcaacaac tcatgagatc   3180
atttatattt gtatattctt tgtgtataaa cttggaattt atctaaaaat agcacattag   3240
aaggtgcaaa accatttaat ttgccaagta cttgtcataa ccttaatgaa gcagttcact   3300
tggttgggaa ccaataataa tatagacagg tagaaaacac agtgatcagg tgaggacatg   3360
aagaatgttt gacagaatgt atttatttct gtttatcttc acatgcaacc ttgtcaaaca   3420
cggtcaaatt ttcaatgcaa aagattaagc atgctaatgc ataattctga gatacctatt   3480
ttaaactgca ggttgcatga aattaatctt tttaaactac tcatcttcag gagttctcac   3540
```

```
ccttctatca aagtagtata taagctcaga ttctcattca gattctaatt atatcaaaca    3600
atcacaagaa tgctactaaa ctgaagagat tctctctctg ttaagggaga agtgttgatg    3660
tggacttgaa actatacagt cacttttcct tttccatata ttttcagtta tacaatgtta    3720
aattcatact ttaggttctg atatgaaaga gatacagagc acctttaaaa agacactgaa    3780
aagcaccatc tgttcatgct caaatcttga agaaaaaatt tttaacttgt taatcataaa    3840
ttgctctaca aatagtatac tggaaacatc cggatgtgag gttataatta aaaatgaaag    3900
caaaacagct tccctgaaaa gaaagaaaac tcttaattca aacctaccag atagctgatt    3960
tatgaaagtg aaaatgctgg catgtataga tattgggaag tcttgggatc tggattttat    4020
cactgaccat ctggttatag tcagagtgaa attttaaaat agcaaaatat tcattaaaag    4080
cctaaagaag ctcataccaa cttgacatgc cacaattagt tatatatccc atgtatcccc    4140
ttctgatatc aattatgtca gttccattgg tgacatcccc gttaatattt gatgacacat    4200
aaacgtccag ccactttaat taggatcaag agaatgggca tcaaatgagt attttttccgt    4260
caagctggga ataataatac tttatcaaga ccaccttttg atccctacat gtgggaaaac    4320
tgaggctcag acagttaaat tacttgccca tagtcacatt tctagagatt gggagaggag    4380
gaaatcaaat ctaggtctat ctgcctccat accgtttctt cacaagaaga gactatcgat    4440
tccctgagct gcataatggg atttgtttgt tcctttcagt ttcctcaagc atgaccacta    4500
catctgctgt aactagtatc cacaattacc cagctgcatt taactaattt aaagctcctc    4560
ataccaattc attacctcaa aaactatttg agagttgaag aagtttctca gaaattaatg    4620
ttgtaataaa caacaacaac accaatactg ggccctctca ttgattcata ttttcttatt    4680
tatcccttct ccatagaaca ctgcaaattg ataaccaaac agaaatttct ctttgtgata    4740
gtttatttta catgtcaact tggctgggct aagagatgcc cagatagctg ataaaacatt    4800
gtttctgaat gtgtctggag ggtgtttcgg agtaaattag catttgaatg agtagaatga    4860
gtgaaaaaga tcgactctca ccaatgtgga caggtattat ccaatcgatt cagggtctca    4920
ataaaacaaa aaggcaaagg aagggtgaat ttttgctctc ccttcttgag ctgggctatc    4980
tatctttttcc tgccctcaga catcggacct gcttgttctt ggtcctttgg actctaggac    5040
ttaaaacagc accattccta cttttcagtt cttaggcttt tggagtgaaa ttgaatgata    5100
ccatttttcca acttgcagac agcaagtgat ggaatttctt ggcctccata atcatgtgag    5160
ccaattctca taataaatct cttctctcc ttttatata tctcctattg gctatttctc    5220
tggaaacccc taatatactc ttgttcatat attttgttac tttttaactc atttgcatct    5280
caggcaaaaa aaaatctttt cttattagct tctatcctcc aatttctttc ccttgtctcc    5340
aagaaagtca ctaccaccct ttttcttcct tcattctttc caagatgtca acccatgtgg    5400
gctggtctgc tatcatctaa atcattctgc tattactgtg gtcagtggga ggcagaagtg    5460
ataagcagca aatatacatc atctagaact tcagttctga cccactggca aagcgtcttc    5520
accacaactg aaaaggttct gaggtagatc tgggtttatt atgaaagatt gacacaattg    5580
aatattaatg tcttccactg aagaagaaag gtaatgatac ctatgtctta tgttttctat    5640
ccttggcata aggcctcaat aatctcaatt caaatccaaa agttttcagg aggaaacctc    5700
tggacacatt aaaatctctt atattaaact tacagatatt tatttagacc ttttcatgga    5760
gtctaccatg gcttatcact gacaaacgga caaagaaata taaggcacg atcctcatct    5820
ctatagttac ttaaagggc aagacaaact ctacagcatt atggattgtt aagcgctagg    5880
taatagcaaa tagaataaac agtataagaa tgcattagat gataacacta ctgagggctg    5940
```

```
taaaaatctc tgaaggcttc aggtgagggg gagatttaaa ctgggcctta actgatttgc    6000
aaaactaaac aagaagacag atatgggtgt tccaagatag agtgggaagc tttagcggtg    6060
gtatttgggg aaaattaatt ggtcagtatt cctacggcat ccattctaca gacagcaaca    6120
gtatagacaa ggaactgtct gaagggacaa aagtgagatg ttcagcaggg taaataggggg   6180 atggtgtgat aatgataatt tctttgatta tagctatctg ctaagccctg tgctaattta    6240
attttttaaa ttaaattaaa actgcataat tcagagataa ttattatctc ttttctttat    6300
cagaaaatta taaacagttg aggtcttcca aggcaaagcc cttgttgtta cccatcatgc    6360
tgagggttag ttcaggtgct tgcgcaatgg catgtacatc tatctccttt gttttgatac    6420
atccatcctt gactcaggaa tagacctaga gacctacaaa agtctcgagt ttgccgagac    6480
acatggcaga tgagggaaca caccactgtg gttccctcag gaaacagatt ctaatctggc    6540
tttacatttt ccattgtaat cttgagatgc ctcatagtca aataatagtt cctcagtgaa    6600
atatatggat agtcatatga tagtagaatg aataaagacc ttatatagct acttggcatt    6660
tcaggccaag ttttattgac agactagttt gctacaaact tatgaaccca ttttattttt    6720
ctagatagca aaatgttaac aattagggac ctgattgaag ggtataaagg attgactgaa    6780
ttattgttgc agtttttatc taagcttatt ttttagtact ttttggatat tggaaatgtg    6840
gctaagagac tgtggacact taagcgttca ataactgtta gttcccttct cttgtgctgt    6900
agaaaaagta caaaaggtcc aagttacctc tcagatatca ggcagatgat taattgtact    6960
gtgaagcggt caagtcctcc agaatactgc attttgggaa cactgattag tcatattctt    7020
ataagaattg ggagctgcca ttttttaacag tttgaataag aaagttgcat tgccaattct    7080
gtacctatct gatatgttct ctccccggag gagaagaaac aggccttatt catctccccc    7140
tccccaaccc taaacattct tcccaagtcc tgaatatgcc tgaaaagaca tgtcattatg    7200 gttttttcctg tggagtctag agttccccca cctgcaccct actgaagtca ttcataggaa    7260
aaggcaatga cagccagatc ttgacagatc accccctagca cagtttcact gtgatcccac    7320 agggggcttta ctgaatatca gtcccagagc tgtctgtctt ttccatttgg gctgctgcag    7380
actgagctga gtaggtcagg gatatgtttt acaggcatta cgcaggccag tcttcagagg    7440
ccagtgtgca tggtgggtcc agccatcctc agacatactc tgcacatgtc atgctggggg    7500
acagagcagc gtgtgtgctg tctggatgat tcctcttgga atgttggttg cctagcaaca    7560
agatcatgct ttgctcttaa gtccaattct caggactttg gcttagttac ttctgatcct    7620 tagactttt cttaccatcc ctcacccggg ttcccagaaa gtcaggggct tcaaattcca    7680
aataatgtag ttattttagc tacgtggtgg cagtctatat gttagatttc cctttggcat    7740
cctacctgta ctttatacac accaacattt ctctaacagt tttaaatatg ctacatttta    7800
aaagactaca cagttggctt tccttttta acacagacac atgtacagca tatgtatgta    7860
ttagaaaaag aatggaagga taaccacaat ataaataac agcagctttc cctttatggt    7920
aggaatatta gatttttaaa ttatcttcaa taaatgtgtt aattttgtaa taaggataaa    7980
tattagcata atatatattg ggattatatg ctattaactg acatttaaaa atatatacaa    8040
agtaatggta aaggaagaaa tactgtcaca cataagtaca ccacaatttc aaccctatat    8100
atgtggaaaa atatgacagg aaattaatga atgaagaggg tttcatcagg ataacagtaa    8160
ttttttctta aattcttgaa ttttaattta aaaataacaa accttaaaaa tatatagtat    8220
tggcatattt acagccatat gttttaaaag gcagaggaaa tcatctttat catggcaaca    8280
```

| | | | | |
|---|---|---|---|---|
| agggtcattt | gggcagattc | ccatagtaaa | agattaaaat | atattttgga cccagagttt | 8340 |
| gttccaatca | ttccacttct | tcattcactc | aaaaagccat | gtttaagcat ctgctttgtg | 8400 |
| ccagatatgt | gaccagccct | gtgaatacag | acctaaagca | gagcatctct gccctcaaag | 8460 |
| aatctatatt | aaaagtcaga | tgagggataa | aaaaatagga | tgcaccattt attataatac | 8520 |
| ttctcaaacc | atgttttgtg | ggtgttttca | agtgaatttt | agatttctct acaagtctta | 8580 |
| attttatatt | tatatggtaa | tctatttaat | taagcaagtt | tttcagaatc atttaaatgg | 8640 |
| caccttataa | ctgagtgcta | acacaggact | tcaaggtcta | cagttatact tgggaatata | 8700 |
| attgcatagt | actgagtatt | atttcatagt | cttggctaat | gagaaaggga cctaaatata | 8760 |
| aatgatatgt | tgtgacacat | gaaaggcaac | tgatgtcata | ggatatttgc caataatttg | 8820 |
| aatagtgaca | aatggccaga | taattgagtc | atattgggat | gtgcaggatg gcatggtcat | 8880 |
| gccaaactca | aaagctgtta | agactatatt | catgctgtaa | tcagagatct tgtttcagca | 8940 |
| aaatgtcatt | ctttatatta | ataaccatt | gttaatgtta | atttcattcc actagaatgc | 9000 |
| agctctatgg | caaaaaaaag | gctttatctg | ttttatctgc | tgctataccc ctaggacctg | 9060 |
| gctcataact | gcctattaaa | catttgctgg | atggattaat | aaataaattg agtattttta | 9120 |
| tttatttata | tatgttttct | aaatttatgc | ttatagttta | ataaagtta tgcctgtttt | 9180 |
| gtgttgacat | gtgtttaaat | atattttata | ataaaaataa | cactggtgga cttaagagaa | 9240 |
| ttttctcct | ttaagaaga | aatatttaat | attaattaag | ggtgctgttg gcccttaaaa | 9300 |
| aaccataggg | ttaaacctaa | ctcttccttt | ttctgtgata | tccgttttct ggctcttctc | 9360 |
| ttctactttt | gcttcccacc | aattcacttt | tcaaaattcc | cacatgccct ttctccctct | 9420 |
| taccttta | cttcctatac | ttgccaaccc | tagcaacttc | ctcactctat catcatacac | 9480 |
| taaaacagag | gaagagaaga | gaagaaaaaa | caaaccagag | aataaggcag gttttccaca | 9540 |
| gccccccaag | accgtcaaag | tgaaggtaag | agactcagaa | gttaccagct aagggttcaa | 9600 |
| atgctaattt | caccatttat | atactgccca | tcagaaccga | gtagacatta accaattttg | 9660 |
| acggcgtact | cttcttgtca | ataaaatttt | taagcgctta | gcatattact tgcaatagct | 9720 |
| ctgggctgga | gcatccgttt | cctctgttca | catactttag | aaggtctcac tccgatcttt | 9780 |
| ctctgataag | aactcctcct | catcaggtga | ggagcttgta | ggatcaaggg gatgtgccca | 9840 |
| tctggtgcct | aagcaccacc | tcatcaagag | ttcgaccctg | catcctgccc aaattgtcct | 9900 |
| gtttctagac | cctagatatg | tgcctaattc | attttttaat | ggtggaccat ctctgcgggt | 9960 |
| gtgtgtactc | ctaagtatca | aatgggtttt | caaatggtgt | ggcttaaaag catgtgctaa | 10020 |
| agtgtcaata | gctctaaatg | tgagtcatga | acagtgcag | aagaaatctt catggggagg | 10080 |
| gaagaaaacg | aggtggttct | tagcccagga | gctcaggtcc | cttcttccta tgctacctcc | 10140 |
| ttatggctag | gaattc | | | | 10156 |

<210> SEQ ID NO 16
<211> LENGTH: 651
<212> TYPE: DNA
<213> ORGANISM: Artificial Sequence
<220> FEATURE:
<223> OTHER INFORMATION: gas5 (SNHG2))

<400> SEQUENCE: 16

| | | | | |
|---|---|---|---|---|
| tttcgaggta | ggagtcgact | cctgtgaggt | atggtgctgg | gtgcggatgc agtgtggctc | 60 |
| tggatagcac | cttatggaca | gttgtgtccc | caaggaagga | tgagaatagc tactgaagtc | 120 |
| ctaaagagca | agcctaactc | aagccattgg | cacacaggca | ttagacagaa agctggaagt | 180 |

```
tgaaatggtg gagtccaact tgcctggacc agcttaatgg ttctgctcct ggtaacgttt    240
ttatccatgg atgacttgct tgggtaagga catgaagaca gttcctgtca tacctttaa    300 aggtatggag agtcggcttg actacactgt gtggagcaag ttttaaagaa gcaaaggact    360
cagaattcat gattgaagaa atgcaggcag acctgttatc ctaaactagg gttttaatg    420 accacaacaa gcaagcatgc agcttactgc ttgaaagggt cttgcctcac ccaagctaga    480
gtgcagtggc ctttgaagct tactacagcc tcaaacttct gggctcaagt gatcctcagc    540
ctcccagtgg tctttgtaga ctgcctgatg gagtctcatg cacaagaag attaaaacag     600 tgtctccaat tttaataaat ttttgcaatc caaaaaaaaa aaaaaaaaa a              651

<210> SEQ ID NO 17
<211> LENGTH: 2370
<212> TYPE: DNA
<213> ORGANISM: Artificial Sequence
<220> FEATURE:
<223> OTHER INFORMATION: hotair

<400> SEQUENCE: 17
ccagttctca ggcgagagcc gcggctgaca gggtctggga cagaaggaaa gccctccagc     60
ctccaggccc tgccttctgc ctgcacattc tgccctgatt tccggaacct ggaagcctag    120
gcaggcagtg gggaactctg actcgcctgt gctctggagc ttgatccgaa agcttccaca    180
gtgaggactg ctccgtgggg gtaagagagc accaggcact gaggcctggg agttccacag    240
accaacaccc ctgctcctgg cggctcccac ccgggactta ccctcagg tccctaatat      300 cccggaggtg ctctcaatca gaaaggtcct gctccgcttc gcagtggaat ggaacggatt    360
tagaagcctg cagtagggga gtggggagtg gagagaggga gcccagagtt acagacggcg    420
gcgagaggaa ggagggggcgt ctttattttt ttaaggcccc aaagagtctg atgtttacaa   480
gaccagaaat gccacggccg cgtcctggca gagaaaaggc tgaaatggag gaccggcgcc    540
ttccttataa gctcgttggg gcctaagcca gtaccgacct ggtagaaaaa gcaaccacga    600
agctagagag agagccagag gagggaagag agcgccagac gaaggtgaaa gcgaaccacg    660
cagagaaatg caggcaaggg agcaaggcgg cagttcccgg aacaaacgtg gcagagggca    720
agacgggcac tcacagacag aggttttatgt attttttattt ttaaaatct gatttggtgt   780 tccatgagga aagggaaaa tctagggaac gggagtacag agagaataat ccgggtccta    840
gctcgccaca tgaacgccca gagaacgctg gaaaaacctg agcgggtgcc ggggcagcac    900
ccggctcggt tcagccactg ccccacaccg ggcccaccaa gccccgcccc tcgcggccac    960
cggggcttcc ttgctcttct tatcatctcc atctttatga tgaggcttgt taacaagacc   1020
agagagctgg ccaagcacct ctatctcagc cgcgcccgct cagccgagca gcggtcggtg   1080
gggggactgg gaggcgctaa ttaattgatt ccttttggact gtaaaatatg gcggcgtcta  1140
cacgaacccc atggactcat aaacaatata tctgttgggc gtgagtgcac tgtctctcaa   1200 ataattttc cataggcaaa tgtcagaggg ttctggattt ttagttgcta aggaaagatc   1260
caaatgggac caattttagg aggcccaaac agagtccgtt cagtgtcaga aaatgcttcc   1320 ccaaagggt tgggagtgtg ttttgttgga aaaaagcttg ggttatagga aagcctttcc   1380
ctgctacttg tgtagaccca gcccaattta agaattacaa ggaagcgaag gggttgtgta   1440
ggccggaagc ctctctgtcc cggctggatg caggggactt gagctgctcc ggaatttgag   1500
aggaacatag aagcaaaggt ccagcctttg cttcgtgctg attcctagac ttaagattca   1560
```

| | | |
|---|---|---|
| aaaacaaatt tttaaaagtg aaaccagccc tagcctttgg aagctcttga aggttcagca | 1620 | |
| cccacccagg aatccacctg cctgttacac gcctctccaa gacacagtgg caccgctttt | 1680 | |
| ctaactggca gcacagagca actctataat atgcttatat taggtctaga agaatgcatc | 1740 | |
| ttgagacaca tgggtaacct aattatataa tgcttgttcc atacaggagt gattatgcag | 1800 | |
| tgggaccctg ctgcaaacgg gactttgcac tctaaatata gaccccagct tgggacaaaa | 1860 | |
| gttgcagtag aaaatagac ataggagaac acttaaataa gtgatgcatg tagacacaga | 1920 | |
| aggggtattt aaaagacaga aataatagaa gtacagaaga acagaaaaaa aatcagcaga | 1980 | |
| tggagattac cattcccaat gcctgaactt cctcctgcta ttaagattgc tagagaattg | 2040 | |
| tgtcttaaac agttcatgaa cccagaagaa tgcaatttca atgtatttag tacacacaca | 2100 | |
| gtatgtatat aaacacaact cacagaatat attttccata cattgggtag gtatgcactt | 2160 | |
| tgtgtatata taataatgta ttttccatgc agttttaaaa tgtagatata ttaatatctg | 2220 | |
| gatgcatttt ctgtgcactg gttttatatg ccttatggag tatatactca catgtagcta | 2280 | |
| aatagactca ggactgcaca ttccttgtgt aggttgtgtg tgtgtggtgg ttttatgcat | 2340 | |
| aaataaagtt ttacatgtgg tgaatataaa | 2370 | |

<210> SEQ ID NO 18
<211> LENGTH: 1052
<212> TYPE: DNA
<213> ORGANISM: Artificial Sequence
<220> FEATURE:
<223> OTHER INFORMATION: htairm1

<400> SEQUENCE: 18

| | | |
|---|---|---|
| aaaagtttgc cggcttccgc agtgatggat caccgtttta gtggcattta aatccccggc | 60 | |
| gctccgccgt ctaggtgacg cgcagtcgcc ccccaggca gcctaggcgg cggcagctgc | 120 | |
| tgcggcgact gcaaaggccg atttggagtg ctggagcgaa gaagagcaaa agctgcgttc | 180 | |
| tgcgcgcgcc cgactccgct gcccgccccg ccaggcctcc gggaggtggg ggctgggagg | 240 | |
| cgtcccccgc tcccgccccc tccccaccgt tcaatgaaag atgaactggc gagaggacga | 300 | |
| atcgcatcca ggagctgcgc agccctggcc gctgccggga cgccctgctc cgcgctgagc | 360 | |
| ttggggccag aaaccagcca tagtccccac actccgccgc cgcagctgag atttagcgga | 420 | |
| ggaaggggcg agggaaggta gggagcaaac ctatgaagaa acatcgcgtt gtcattggaa | 480 | |
| cttccaagcc tttgctgtta agagccaggt tcttaaatca acccgcccca cacacatgtt | 540 | |
| gcttacatgc tgcgtttttct cacggtctgt tttgcctgaa cccatcaaca gctgggagat | 600 | |
| taatcaacca cactgaaaat gtggagggat ttatggggga gggggttgaa atgtgggtgt | 660 | |
| ttgaaacaaa agtgtataaa caaatgaatt gttgataact tagttattga cctgagagact | 720 | |
| ggtagcttat taaagaaact ccgtgttact cattcctgga gttgggggtt tctgtaggca | 780 | |
| ctttatttct ccactttcaa gagcttgggc ttggcccaaa tcttagactg tccaattctg | 840 | |
| cctctattac caatttaaat ctatggcttg aacctgtgca ctgaaaatca aatcctttaa | 900 | |
| aaagaaagag gagaagaaga agcaaaaaag aaagaaaaaa cacttattag aagccctagt | 960 | |
| cattttttgg ctttctgttt tgttgctgtc cattgaagac tttgaacatg ccgccttaat | 1020 | |
| aaatgtatta aaattgaaaa aagaaaaaaa aa | 1052 | |

<210> SEQ ID NO 19
<211> LENGTH: 1386
<212> TYPE: DNA
<213> ORGANISM: Artificial Sequence
<220> FEATURE:
<223> OTHER INFORMATION: Lust

<400> SEQUENCE: 19

```
aaatgccgcc acagactttc actatgttct cttcactgtc aaatggagag tttgatatac    60
taagcttact ctcaatggac ataataggaa tataacaaac tagaaaaaag ggaaacatta   120
agatgtttta gtgattacca gacaggtatt cagtagttaa caaagccctg ccaggtaggt   180
agccatgttt aaaggcagaa caaattctat aatgaagtcc ttggtactgt acttattcta   240
gtaacatcaa ttttaatata tacaaagctt ttttttttaaa aaaagtcac tcctttggaa   300
caaaccactc cttcaacctt tttttaaaat tgtacagact tgttccattt tcatgaatat   360
ctagacttgg tgagtgaagc aacctgattg gcttccatcc agctggtagc atcttgcaag   420
tgataaaact ccacgaaggc gaaaccacgg cttacaccta gagacagcat tcagatatag   480
acgggatact tgtgttagtc agttccttta taacaggtga atctctctcc cactgcttca   540
acactgcgtg acaaagccaa ttgggaagca gctttacaaa tgtgacttga cttggggatc   600
ttcttgatac tttgccatgg caaggaacaa gccgcctgaa ctaaatgcca ctccatttga   660
ttccacgctt aaagtaacca tgcaaccgac tatagtcaaa aaaaaaaagg agtttataaa   720
tcattactta cctaaggaaa aaaaagtccc taaaacaaag tttaaaaaag ttcctcagat   780
gctaacatgg ttttcaaaga gtcacattcc ttagccatgg caaacctttc attctgaatt   840
catgtgcttg aagactgggg gaatcaggat gttctttagg gactgaggtg ggaatgggga   900
agagaacaat aatatcagga actaagcaag ctctcacctg ttttcctctt catcagcctc   960
acatccgcag gctgagggcc ttcgaaggac tccatcattt ctcgaatctg cacagggttt  1020
tacattattt acagttaaag cttttgccac acactattcc ccatggaata ggaattacat  1080
caactgtttta attagccaag ttttttttttt ttttaagatg ggagtctctg tctctcactc  1140
acttgattgc ccaggctgga gtgcagtggc atgatctcag ctcactgcaa ccaccacctc  1200
ctgggttcaa gcaattctcc tgcctcagcc tcccgagtag ctgggattat aggtgtgcac  1260
caccatgcgt gactgatttt tttttttttt tgagacggag tctcgctctg tcacccaggc  1320
tggagtacag tgacgtgatc tcggctcact tcaacctcca cctcctggat tcaagcgatt  1380
cttctg                                                              1386
```

<210> SEQ ID NO 20
<211> LENGTH: 8708
<212> TYPE: DNA
<213> ORGANISM: Artificial Sequence
<220> FEATURE:
<223> OTHER INFORMATION: malat 1

<400> SEQUENCE: 20

```
gtaaaggact ggggccccgc aactggcctc tcctgccctc ttaagcgcag cgccatttta    60
gcaacgcaga agcccggcgc cgggaagcct cagctcgcct gaaggcaggt ccctctgac   120
gcctccggga gccaggtttt cccagagtcc ttgggacgca gcgacgagtt gtgctgctat   180
cttagctgtc cttataggct ggccattcca ggtggtggta tttagataaa accactcaaa   240
ctctgcagtt tggtcttggg gtttggagga aagcttttat ttttcttcct gctccggttc   300
agaaggtctg aagctcatac ctaaccaggc ataacacaga atctgcaaaa caaaaacccc   360
taaaaaagca gacccagagc agtgtaaaca cttctgggtg tgtccctgac tggctgccca   420
aggtctctgt gtcttcggag acaaagccat tcgcttagtt ggtctacttt aaaaggccac   480
```

```
ttgaactcgc tttccatggc gatttgcctt gtgagcactt tcaggagagc ctggaagctg    540
aaaaacggta gaaaaatttc cgtgcgggcc gtgggggget ggcggcaact ggggggccgc    600
agatcagagt gggccactgg cagccaacgg cccccggggc tcaggcgggg agcagctctg    660
tggtgtggga ttgaggcgtt ttccaagagt gggttttcac gtttctaaga tttcccaagc    720
agacagcccg tgctgctccg atttctcgaa caaaaaagca aaacgtgtgg ctgtcttggg    780
agcaagtcgc aggactgcaa gcagttgggg agaaagtcc gccattttgc cacttctcaa     840
ccgtccctgc aaggctgggg ctcagttgcg taatggaaag taaagccctg aactatcaca    900
ctttaatctt ccttcaaaag gtggtaaact atacctactg tccctcaaga gaacacaaga    960
agtgctttaa gaggtatttt aaaagttccg ggggttttgt gaggtgtttg atgacccgtt   1020
taaaatatga tttccatgtt tcttttgtct aaagtttgca gctcaaatct ttccacacgc   1080
tagtaattta agtatttctg catgtgtagt ttgcattcaa gttccataag ctgttaagaa   1140
aaatctagaa aagtaaaact agaaccatt tttaaccgaa gaactacttt ttgcctccct    1200
cacaaaggcg gcggaaggtg atcgaattcc ggtgatgcga gttgttctcc gtctataaat   1260
acgcctcgcc cgagctgtgc ggtaggcatt gaggcagcca gcgcaggggc ttctgctgag   1320
ggggcaggcg gagcttgagg aaaccgcaga taagttttt tctctttgaa agatagagat    1380
taatacaact acttaaaaaa tatagtcaat aggttactaa gatattgctt agcgttaagt   1440
tttaacgta attttaatag cttaagattt taagagaaaa tatgaagact agaagagta    1500
gcatgaggaa ggaaaagata aaaggtttct aaaacatgac ggaggttgag atgaagcttc   1560
ttcatggagt aaaaaatgta tttaaaagaa aattgagaga aaggactaca gagccccgaa   1620
ttaataccaa tagaagggca atgcttttag attaaaatga aggtgactta aacagcttaa   1680
agtttagttt aaaagttgta ggtgattaaa ataatttgaa ggcgatcttt taaaaagaga   1740
ttaaaccgaa ggtgattaaa agaccttgaa atccatgacg cagggagaat tgcgtcattt   1800
aaagcctagt taacgcattt actaaacgca gacgaaaatg gaaagattaa ttgggagtgg   1860
taggatgaaa caatttggag aagatagaag tttgaagtgg aaaactggaa gacagaagta   1920
cgggaaggcg aagaaaagaa tagagaagat agggaaatta aagataaaa acatactttt    1980
agaagaaaaa agataaattt aaacctgaaa agtaggaagc agaagaaaaa agacaagcta   2040
ggaaacaaaa agctaagggc aaaatgtaca aacttagaag aaaattggaa gatagaaaca   2100
agatagaaaa tgaaaatatt gtcaagagtt tcagatagaa aatgaaaaac aagctaagac   2160
aagtattgga gaagtataga agatagaaaa atataaagcc aaaaattgga taaaatagca   2220
ctgaaaaaat gaggaaatta ttggtaacca atttatttta aaagcccatc aatttaattt   2280
ctggtggtgc agaagttaga aggtaaagct tgagaagatg agggtgttta cgtagaccag   2340
aaccaattta gaagaatact tgaagctaga aggggaagtt ggttaaaaat cacatcaaaa   2400
agctactaaa aggactggtg taatttaaaa aaaactaagg cagaaggctt ttggaagagt   2460
tagaagaatt tggaaggcct taaatatagt agcttagttt gaaaaatgtg aaggactttc   2520
gtaacggaag taattcaaga tcaagagtaa ttaccaactt aatgttttg cattggactt     2580
tgagttaaga ttatttttta aatcctgagg actagcatta attgacagct gacccaggtg   2640
ctacacagaa gtggattcag tgaatctagg aagacagcag cagacaggat tccaggaacc   2700
agtgtttgat gaagctagga ctgaggagca agcgagcaag cagcagttcg tggtgaagat   2760
aggaaaagag tccaggagcc agtgcgattt ggtgaaggaa gctaggaaga aggaaggagc   2820
gctaacgatt tggtggtgaa gctaggaaaa aggattccag gaaggagcga gtgcaatttg   2880
```

```
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgtttttctg gaacttactt atggtaacct    3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt tttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac cccctttaatc agactttaaa    3720 agtgcttaac cccttaaact tgttattttt tacttgaagc attttgggat ggtcttaaca    3780
gggaagagag agggtggggg agaaaatgtt tttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080 gggagggca aatattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt ttccccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt ttttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt ttttagtgta    4680
ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860 ttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaattt taagcaaatg aaagctacca atttaaagtt    5100
acggaatcta ccattttaaa gttaattgct tgtcaagcta taaccacaaa aataatgaat    5160
tgatgagaaa tacaatgaag aggcaatgtc catctcaaaa tactgctttt acaaaagcag    5220
```

```
aataaaagcg aaaagaaatg aaaatgttac actacattaa tcctggaata aaagaagccg   5280
aaataaatga gagatgagtt gggatcaagt ggattgagga ggctgtgctg tgtgccaatg   5340
tttcgtttgc ctcagacagg tatctcttcg ttatcagaag agttgcttca tttcatctgg   5400
gagcagaaaa cagcaggcag ctgttaacag ataagtttaa cttgcatctg cagtattgca   5460
tgttagggat aagtgcttat ttttaagagc tgtggagttc ttaaatatca accatggcac   5520
tttctcctga ccccttccct agggagatttc aggattgaga aattttttcca tcgagccttt   5580 ttaaaattgt aggacttgtt cctgtgggct tcagtgatgg gatagtacac ttcactcaga   5640
ggcatttgca tctttaaata atttcttaaa agcctctaaa gtgatcagtg ccttgatgcc   5700
aactaaggaa atttgtttag cattgaatct ctgaaggctc tatgaaagga atagcatgat   5760
gtgctgttag aatcagatgt tactgctaaa atttacatgt tgtgatgtaa attgtgtaga   5820
aaaccattaa atcattcaaa ataataaact attttttatta gagaatgtat acttttagaa   5880
agctgtctcc ttatttaaat aaaatagtgt tgtctgtag ttcagtgttg gggcaatctt   5940 ggggggggatt cttctctaat ctttcagaaa ctttgtctgc gaacactctt taatggacca   6000
gatcaggatt tgagcggaag aacgaatgta actttaaggc aggaaagaca aatttttattc   6060 ttcataaagt gatgagcata taataattcc aggcacatgg caatagaggc cctctaaata   6120
aggaataaat aacctcttag acaggtggga gattatgatc agagtaaaag gtaattacac   6180
attttatttc cagaaagtca gggtctata aattgacagt gattagagta atactttttc   6240
acatttccaa agtttgcatg ttaactttaa atgcttacaa tcttagagtg gtaggcaatg   6300
ttttacacta ttgaccttat ataggggaagg gaggggggtgc ctgtgggggtt ttaaagaatt   6360 ttcctttgca gaggcatttc atccttcatg aagccattca ggattttgaa ttgcatatga   6420
gtgcttggct cttccttctg ttctagtgag tgtatgagac cttgcagtga gtttatcagc   6480
atactcaaaa tttttttcct ggaatttgga gggatgggag gaggggggtgg ggcttacttg   6540 ttgtagcttt tttttttttt acagacttca cagagaatgc agttgtcttg acttcaggtc   6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840
tgctttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
tgcgaagggc cagagaagcc agacccagta agaaaaaata gcctatttac tttaaataaa   7140
ccaaacattc cattttaaat gtggggattg ggaaccacta gttctttcag atggtattct   7200
tcagactata gaaggagctt ccagttgaat tcaccagtgg acaaaatgag gaaaacaggt   7260
gaacaagctt tttctgtatt tacatacaaa gtcagatcag ttatgggaca atagtattga   7320
atagatttca gctttatgct ggagtaactg gcatgtgagc aaactgtgtt ggcgtggggg   7380 tggagggggtg aggtgggcgc taagcctttt tttaagattt tcaggtacc cctcactaaa   7440 ggcaccgaag gcttaaagta ggacaaccat ggagccttcc tgtggcagga gagacaacaa   7500
agcgctatta tcctaaggtc aagagaagtg tcagcctcac ctgattttta ttagtaatga   7560
ggacttgcct caactccctc tttctggagt gaagcatccg aaggaatgct tgaagtaccc   7620
```

```
ctgggcttct cttaacattt aagcaagctg tttttatagc agctcttaat aataaagccc    7680
aaatctcaag cggtgcttga aggggaggga aaggggggaaa gcgggcaacc acttttccct    7740
agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatcccataa tcggtttcaa ggtaacgatg gtgtcgaggt    7920
cttggtgggg ttgaactatg ttagaaaagg ccattaattt gcctgcaaat tgttaacaga    7980
agggtattaa aaccacagct aagtagctct attataatac ttatccagtg actaaaacca    8040
acttaaacca gtaagtggag aaataacatg ttcaagaact gtaatgctgg gtgggaacat    8100
gtaacttgta gactggagaa gataggcatt tgagtggctg agagggcttt tgggtgggaa    8160
tgcaaaaatt ctctgctaag acttttttcag gtgaacataa cagacttggc caagctagca    8220
tcttagcgga agctgatctc caatgctctt cagtagggtc atgaaggttt ttcttttcct    8280
gagaaaacaa cacgtattgt tttctcaggt tttgcttttt ggccttttttc tagcttaaaa    8340 aaaaaaaaag caaaagatgc tggtggttgg cactcctggt ttccaggacg gggttcaaat    8400
ccctgcggcg tctttgcttt gactactaat ctgtcttcag gactcttttct gtatttctcc    8460 ttttctctgc aggtgctagt tcttggagtt ttggggaggt gggaggtaac agcacaatat    8520
ctttgaacta tatacatcct tgatgtataa tttgtcagga gcttgacttg attgtatatt    8580
catatttaca cgagaaccta ataactgc cttgtcttttt tcaggtaata gcctgcagct    8640
ggtgttttga gaagccctac tgctgaaaac ttaacaattt tgtgtaataa aatggagaa    8700 gctctaaa                                                          8708

<210> SEQ ID NO 21
<211> LENGTH: 3756
<212> TYPE: DNA
<213> ORGANISM: Artificial Sequence
<220> FEATURE:
<223> OTHER INFORMATION: neat 1

<400> SEQUENCE: 21
ggagttagcg acagggaggg atgcgcgcct gggtgtagtt gtggggagg aagtggctag       60 ctcagggctt caggggacag acagggagag atgactgagt tagatgagac gagggggcgg      120
gctgggggtg cgagaaggaa gcttggcaag gagactaggc ctaggggac cacagtgggg       180 caggctgcat ggaaaatatc cgcagggtcc cccaggcaga acagccacgc tccaggccag      240
gctgtcccta ctgcctggtg gaggggggaac ttgacctctg ggagggcgcc gctcttgcat     300
agctgagcga gcccgggtgc gctggtctgt gtggaaggag gaaggcaggg agaggtagaa      360
ggggtggagg agtcaggagg aataggccgc agcagccctg gaaatgatca ggaaggcagg      420
cagtgggtgc agggctgcag gagggccggg agggctaatc ttcaacttgt ccatgccagc     480 agccccttttt tttccagacc aagggctgtg aacccgcctg gggatgaggc ctggtcttgt      540
ggaactgaac ttagctcgac ggggctgacc gctctggccc agggtggtat gtaattttcg      600
ctcggcctgg gacggggccc aggccgggcc cagcctggtg gagcgtccag gtctgggtgc      660
gaagccaggc ccctgggcgg aggtgagggg tggtctgagg agtgatgtgg agttaaggcg     720
ccatcctcac cggtgactgg tgcggcacct agcatgtttg acaggcgggg actgcgaggc     780
acgctgctcg ggtgttgggg acaacattga ccaacgcttt attttccagg tggcagtgct     840
ccttttggac ttttctctag gtttggcgct aaactcttct tgtgagctca ctccacccct    900
```

```
tcttcctccc tttaacttat ccattcactt aaaacattac ctggtcatct ggtaagcccg      960
ggacagtaag ccgagtggct gttggagtcg gtattgttgg taatggtgga ggaagagagg     1020
ccttcccgct gaggctgggg tggggcggat cggtgttgct tgcctgcaga gagggtgggg     1080
agtgaatgtg cacccttggg tgggcctgca gccatccagc tgaaagttac aaaaatgctt     1140
catggaccgt ggtttgttac tatagtgttc ctcatggcga gcagatggaa ccgggagaca     1200
tggagtccct ggccagtgtg agtcctagca ttgcaggagg ggagaccctg gaggagagag     1260
cccgcctcaa ttgatgcctg cagattgaat ttccagaggc ttaggaggag gaagttctcc     1320
aatgttctgt ttccaggcct tgctcaggaa gccctgtatt caggaggcta ccatttaaag     1380
tttgcagatg agcttatggg gggcaatctt aaaaagtcca cagcagatgc atccggctcg     1440
agggggccatc agctttgaat aaatgcttgt tccagagccc atgaatgcca gcaggcaccc    1500
ctccttttcct ggggtaaagg ttttcagatg ctgcatcttc taaattgagc ctccggtcat   1560
actagttttg tgcttggaac cttgcttcaa gaagatccct aagctgtaga acattttaac     1620
gttgatgcca caacgcagat tgatgccttg tagatggagc ttgcagatgg agcccgtga      1680
cctctcacct acccacctgt ttgcctgcct tcttgtgcgt ttctcggaga agttcttagc     1740
ctgatgaaat aacttggggc gttgaagagc tgttttaattt taaatgcctt agactgggga   1800
tatattagag gaagcagatt gtcaaattaa gggtgtcatt gtgttgtgct aaacgctggg     1860
agggtacaag ttggtcattc ctaaatctgt gtgtgagaaa tggcaggtct agtttgggca    1920
ttgtgattgc attgcagatt actaggagaa gggaatggtg ggtacaccgg tagtgctctt    1980
ttgttcttgc ttcgtttttt taaacttgaa ctttacttcg ttagatttca taatactttc    2040
ttggcattct agtaagagga ccctgaggtg ggagttgtgg gggacgggga gaagggggaca   2100
gcttggcacc ggtcccgtgg gcgttgcagt gtgggggatg ggggtatgca gcttggcact   2160
ggtactggga gggatgaggg tgaagaaggg gagagggttg gttagagata cagtgtgggt    2220
ggtgggggtg gtaggaaatg caggttgaag ggaattctct ggggctttgg ggaatttagt    2280
gcgtgggtga gccaagaaaa tactaattaa taatagtaag ttgttagtgt tggttaagtt    2340
gttgcttgga agtgagaagt tgcttagaaa ctttccaaag tgcttagaac tttaagtgca    2400
aacagacaaa ctaacaaaca aaaattgttt tgctttgcta caaggtgggg aagactgaag    2460
aagtgttaac tgaaaacagg tgacacagag tcaccagttt tccgagaacc aaagggaggg    2520
gtgtgtgatg ccatctcaca ggcaggggaa atgtctttac cagcttcctc ctggtggcca    2580
agacagcctg tttcagaggg ttgttttgtt tggggtgtgg gtgttatcaa gtgaattagt    2640
cacttgaaag atgggcgtca gacttgcata cgcagcagat cagcatcctt cgctgcccct    2700
tagcaactta ggtggttgat ttgaaactgt gaaggtgtga ttttttcagg agctggaagt    2760
cttagaaaag ccttgtaaat gcctatattg tgggctttta acgtatttaa gggaccactt    2820
aagacgagat tagatgggct cttctggatt tgttcctcat ttgtcacagg tgtcttgtga    2880
ttgaaaatca tgagcgaagt gaaattgcat tgaatttcaa gggaatttag tatgtaaatc    2940
gtgccttaga aacacatctg ttgtctttc tgtgtttggt cgatattaat aatggcaaaa     3000
ttttgccta tctagtatct tcaaattgta gtctttgtaa caaccaaata accttttgtg     3060
gtcactgtaa aattaatatt tggtagacag aatccatgta cctttgctaa ggttagaatg    3120
aataatttat tgtattttta atttgaatgt ttgtgctttt taaatgagcc aagactagag    3180
gggaaactat cacctaaaat cagtttggaa aacaagacct aaaaagggaa ggggatgggg   3240
attgtgggga gagagtgggc gaggtgcctt tactacatgt gtgatctgaa aaccctgctt    3300
```

```
ggttctgagc tgcgtctatt gaattggtaa agtaatacca atggctttt atcatttcct      3360 tcttcccttt aagtttcact tgaaattta aaaatcatgg ttattttat cgttgggatc       3420 tttctgtctt ctgggttcca tttttaaat gtttaaaaat atgttgacat ggtagttcag      3480
ttcttaacca atgacttggg gatgatgcaa acaattactg tcgttgggat ttagagtgta     3540
ttagtcacgc atgtatgggg aagtagtctc gggtatgctg ttgtgaaatt gaaactgtaa     3600
aagtagatgg ttgaaagtac tggtatgttg ctctgtatgg taagaactaa ttctgttacg     3660
tcatgtacat aattactaat cactttctt ccccttaca gcacaaataa agtttgagtt      3720
ctaaactcat tagaaaaaaa aaaaaaaaaa aaaaaa                               3756
```

<210> SEQ ID NO 22
<211> LENGTH: 2942
<212> TYPE: DNA
<213> ORGANISM: Artificial Sequence
<220> FEATURE:
<223> OTHER INFORMATION: rncr3

<400> SEQUENCE: 22

```
cgccctccgc agacctccgc gcagcggccg cgggcgcgag gggagggggtc tggagctccc     60 tccggctgcc tgtcccgcac cggagcccgt ggggtgggga ggtgtgcagc ctgtgacaga     120 cagggggctta gagatgcaaa cagactcagg gagagaaaca gaagctgatt ctgtgacaga    180
agcagatctg tgcagcacag atgcggtgtg cgtggggagg gggtcgcctg ggagcgcatt     240
gcggagtgct tgtgtgtgca gattttctc tgggctcagg actcattgta tgtgggtcaa     300
caccttcctc cgtgactgtg tttttgttct gagctgagtt ttttggtttg cccttaaaaa    360
aataataatt tggcatccag agactggcag actgcctcag ggcctggact gcggatatat     420
tgtgttctgc ttgaggtttg gggaggaggg caggcggtag aagggagag ggggagctgt      480 ttgtcacact ttgctgtaga gctgagagca cctgacaagc ttaaggaagt cgttgggcta     540
tgtggacaag aaggagccag ctcccagcgg gttcacaagc tctatcggag ttgaaagcgt     600
ggtcatggct ctaaggagca cctcacgccc tccctgtagc tgttattgca gtttcaggca    660
gagatccagg agctgcagag gaagggagag gcacaataac ctacatggac ccaagggaga    720
catgtgttcc tttaaaaatg tgaacagaag gaaaaacaga atgtgtgcaa ctggggggtct    780 gaggaaagac tgttttgaaa gaggctgtca gggaatggaa agggttaagc ttttcatcct    840
gaagaacctg cttcccaaat caggccttcc tcccatcact agaccctgag cagcagctgg    900
tcctagagac ccccctcgta ctgcgctgcc acagtctcat cccatttcca gctctgtatt    960
aaccaccaag ctgcagcgga tggggcaaga cctaagctca ttaatttcca ggtggaggaa   1020
atggaggagg ggcaggtccc tgcagtagag ggaggagcag agaaaggagg ccaagagctg    1080
gatccttctg cccaggaagc ctgctgcatc ccttcccccg agcatggcag aggcctggct    1140
ttgcaaggcc aaggccataa gggatgctta ggagattaat ttgattcctg acacaataat    1200
caagccctaa gagtctccac tgaagcttac tgaggacttc tttcctctcc aaagcctcag    1260
tctagcctgc taaataaatt agtattcagt gatgccttgg atcagggccc ctccccggcc    1320
tcagtttccc caaatatta ttaagtacct actgtgtgca atccttgtgt aattattacc    1380
tcttaggctc ttcatttgcc ctcctaaagc agtgtttaga gtcaggcaga ggttaagtgt    1440
gttgcacctc acctagatac ttccagaacc ttctctgggt ctgcagaatg tggcacaacc    1500
tgcttgcccc cgcagagaga aagctgcagt gcacatcctg cagactgcag gtgctgggct    1560
```

```
gcctctggag tcccagaagg caagcttggc tgcaggacag aaagggagaa cagcttctct      1620 caccccctgag ccttcacaag cccttgtcta tttgccgttg ccttcaaaat atacctcccc     1680
cgaaaccagt agctttctga gtcctggtgt ccccctccgcc ctttctggac aggtttggga    1740
agaagaaagc agtcagtgct gggccttatt ggggtgtgaa gcgccttgct ctgccccttc    1800
tgctcactgt gaaggccgct ggatgcttct cttaggcatg gtttaagcct ccgattacta    1860
aaccccttgc cccacaaacg tccacattga cgagcctctt tttagtaact gcttccccgt    1920
aattccttca gaggttgctg tacccttcgc tgatgtgctg ccctcctgta aaacctccag    1980
atgccttccc acgtaatgcc cctttcagat gctttaagct gagagcttaa accacaggta    2040
ccatggctga cgcctgccag gtttctgctg cagataatct atgatgggag gggcatattt    2100
tttacttcat tacttatgta aactcttgtt ccagaaagct ttaatgtgtg tgggagtgtt    2160
ctgggtctat taggtctgtg cgcatgggtg tgggcatttg cctgtgtcca ccgggtgggt    2220
ctcattatga aatgtatgtt tatgtagggc tttaatggct gaaaatggca aagagatgaa    2280
tagaccactt ggccccatgt gtaattgcca ggccccttct gtgctcaaat gaggtgtccg    2340
agtgaaggtc agcccttccc ttctgtattt ggggcctatt tatgccacca gtaatttta    2400 aagaaatctg aatagttctc cccttttgagt gcatttaact ctttagtatc ttctctctta   2460
cctatttgag cccctctagc tacagtctgg cttaaatgaa aggggaatta tatgcttaag    2520
aaaaagtagg acacggttga ggcagtttgc tgactaata cgcgaagaag gacctgatgg    2580
gctcatatgc accactgcca tcacagtccc catcgtgatg caagcttata tgattcttga    2640
gaaacagccc agatcctc ttaagcggaa aagagattga ccttctagca gaggcaaaga     2700
atggagtctt ctgggggcag ctgcaaagcg ttctccctag acagatgga gcctcccttt    2760 cctcatctac tctgtgggtg gtttcagggc ccacgagtca acatgaggag ttgtgctggt    2820
ggtatgtgtg ttggaggctg ggctggctga ttcacagtga cgaggatgtc aataataaca    2880
agaatgagaa tgatggtacc taataaagac ttttttttccc aaaaaaaaaa aaaaaaaaa    2940 aa                                                                   2942
```

<210> SEQ ID NO 23
<211> LENGTH: 2591
<212> TYPE: DNA
<213> ORGANISM: Artificial Sequence
<220> FEATURE:
<223> OTHER INFORMATION: lincrna-ror

<400> SEQUENCE: 23

```
ggtgaaataa acagccatgt tgctcacaca aagcctgttt ggtggtctct tcacacggac      60
gctcatgaaa tttggtgatg tgactcggat aggggggaccct cccttgggag atcagtaccc   120
tgtcctcctg ctctttgctc cgtgagaaag atccacctac aacctcaggt ccttagacca    180
accagcccaa gaaacatctc accaatttca aatccagacc ccactggaaa tcggactgtc    240
caactcacct gacagccact cccacagccg ctggaactct ggcccaaggc tctctgactc    300
cttcccagat cttcttggct tagcggctga agactgacgc tgcccgatcg cctcggaagc    360
cccctagacc atcacggacg ccgagcttcg ggtaactctc acagtggaag aaacacaact    420
acagatttct acctggtgca tggccatcgc tcatgaagac tacaacttcc agcttccttt    480
gaagaaaaag aggacttgat ggcattgtcg ctaagtaaga aataatgtgt gtgacttcag    540
ggttgccccc ttaaagggag gggacatttt ccatcctgct gttcagagta tggatgtgat    600
gagagacatc ttggatgatg cagaggaggt gaacacccca ggacaatgaa accacaggag    660
```

```
agaaagagcc tgcgctggcc catctagcac agccactgga cacagggacc acctgcctct    720
gcactcttat ggaaggagga aatctaactt tcccagttta aggcactgtt actttgggct    780
cctgttacat aactgtggca gaatgaaggt tcaacatgga aactggcaat gttgaagaaa    840
cataaagttc attgcttgaa tatctgaagt tgtggactca atctcatacc tgctccactt    900
atgagttata gttcttccag gtctcaggaa tgggatcagc aggtctcagg gttgtactct    960
cctggatctc tcaccagcca cctcaaacca gctgccatag cctgtccact tccactccaa   1020
tcttctcttc cttcatcacc tcccttgcac accctgataa cctcgaaaga gaactcttcc   1080
caaggctctg ttccaaacac atcgccactc tgcttagaac cttcaatgac tcctcatggc   1140
ctaggaggtt tctctcccat ctggatccag ctgacgttcc cagcaccttc tcctgactcc   1200
tgtcttttct tgaaccagtt ctgcccaaca aggaggaaag ggctgacaga gtgaaagtcc   1260
cagggcatgt gggaatgtga ctcttttcac tttaaattct atgactggaa agttttgggc   1320
agagttggac atgtgcactt agcttccaga agacagaatc ctttttaaaag agtcagagaa   1380 aacactggct tcctgccatg acatgagata cagacaggag agttgggaag cttttttaaag   1440 atggcactat gactacaatc acagaaactc tccatgagga agtaaaagaa agcacctgca   1500
acactccagc tatgcagacc actctgtaat gggctcagat ctggacaggt gtgtggaaag   1560
gtgggtcaac aggtcaggcg tcacagactt ggaacattca tggtggaaaa gaaaaagccc   1620
caaagaagag acttcaggat aaatgagaaa atactcaaga cagcaaaagt ctctttttaga   1680 aatgttggag aaagaacact taatgtcagg agttactgtt gattgatggc cttactgtgt   1740
agcaggtgag aaacccattg ttcagttccc taaagtcacc ctattctccc aatcatccta   1800
tggaggggga accatgatgg ttatccccat cttataaata aagcaacaga ggcttagaag   1860
gacgaactct tttctcaag gttacccaga tcattttgca gaagtcccta gatttgaatc   1920
atgctcttgc tttgaggtta aagacacagg ggaagtcgaa ctccttatct cctatatcct   1980
gaatagggaa aaccaaacat tgtcaagagg agaggaagcc tgagagttgg catgaatcag   2040
agtgctgggc agtctggagt cttccccact gagttgatga tggaacagta gagtggggcc   2100
tgagccccgt tagggcatga gctgctgaat gattcatgtg aacaccatgc acatgggagt   2160
gaggttttga gcagtgtgcc acaggagcct accctcaggc cccaccataa aatgtagggc   2220
cagtcctaca ttttatcaat gacttgcgtg aacacagaaa atgtggatac aaccaaaagg   2280
taacaatcca attaaaaaat ggacaaaaaa cttgaataaa catttctcaa aagaagatat   2340
acaaatgatc aaaaagcata tgaaaaaatg ctcaacatcg ctaattgtaa gagaaatgca   2400
aatcaaaact ataatgagat accaccttat attgattagg aagactgcta taaaaatagt   2460
aaacaaacaa acaaacaaag taagtcttgg ggaggatgca gagaaattaa aatttttgtg   2520
cactgttagt gggaatgtaa aatggtgcag ctgttacggg aaacggtatg acagttcctc   2580
aaaaaataaa a                                                       2591
```

<210> SEQ ID NO 24
<211> LENGTH: 3121
<212> TYPE: DNA
<213> ORGANISM: Artificial Sequence
<220> FEATURE:
<223> OTHER INFORMATION: lincrna-p21

<400> SEQUENCE: 24

```
gcagtctgac ccacactccc cacgcccagg accaagtcgc ctgagcccca tagccacaac    60
```

-continued

```
tctctgccgg ccttgcccgg gcttgccttc ggttgcatca tctcccagct ttgccagggg      120
tgcagaagtg aaccacccac tcagcgctgg aaaaaccagc taattatatc tccaaagacc      180
cagggcaaga acttgtggac aacctcagct ggcctggcct gtcccactcg ctttccattt      240
ccccccaccc tgagacagga tgccactgtg tagcccagtg tagtgaacac ttggaataca      300
aaataaagat ggtggaatga acattccgt ctccagttcc taacatcaga agtgagcacc      360
tgtgtgtcac cagcaacata ttggaggcca gctgcctaca ccaatcagaa cagggacca      420 caaagtctgc aggggtgaga taggccttt cagtgtctac gatttcatca tggacattac      480
tgtcgatttc tcttcctgcc cctgtatgtg cgggtctatc gccatctcgc catctccggc      540
tcctgtgtta tgaagacagt ctcatgcagc ccagaccaat ctcaaattga ctaggtaaac      600
tgaggctggc cttgaaccag tccctcctgc ctctatctcc tgagagctgg gtaacagctt      660
ctggagcctc acccagcttc gctttcacca ccccagccaa tcctgtgact cctcttcata      720
gcgagagcat tgacacttat gttctgagtg tgaaaaaaaa aaaaaaatca catagtactt      780
cctactagaa ccttgcccgg gtcaactgaa gtgtgtgtgt ttgcttacca gtctgcaggt      840
ttgcttaagt ttgtttattt tagagaccag gtcttgctct gttgcctaag ccaacttgaa      900
actcttgggc tccaacagtt ctcctgctcc atctttctag agcagctggg actctaggca      960
tgctccacta cagctgactg aagcttgaat gaatgaatga atgaatgaat gagttactac     1020
ctctgaggga ccctcctcat ggccttctca actctgtact ttaattagtt gcttagaggt     1080
gtctccatgc ctcagtttcc ccatctgtaa tagtaaacga gttcacaggc gtggtctgtg     1140
cttggagcaa gaacaaaacc atcctggcct atactctcta gggactctac agagcccatc     1200
cctttggcta tcagactgtt gagataaagg ttcccccagg aatcggaatc ccctccgaca     1260
ggagtctcat gctcagagaa gaaaaaaagc tgaagcctgc tgacagccag agagggtact     1320
tgtctgtcag ggaaaaattc tacacaggac agactggagc ccagactggt ctgggtcagt     1380
gacacacggc acagcacacg gtgggacaac ctggctgtgc atctctctca aacctcaacc     1440
tcagtctgaa gatggattgg ggggggggt ccctggacct cattacttgt cacccttctc     1500
actgtggcca cagcgaagcg aatacatctc tctgcttttc actacgtagc tccatcattg     1560
ccttgggggg gggtagcgag gaaggtcact ggggccctgc ctctgataag aagaacgagc     1620
aattatgatt ccaggaacc gagggtgctc ttgctgttca gtgtctccag cacccccgga     1680
gaccccaggg ctgccgtcaa gggtgttcaa taaacacgta tcgattgagc caacaatgcc     1740
agaattggac ctgcagagga gaaaatggac aaacaagaca gtgagcctgc aggtgagacc     1800
agaactggag ccaacaatct acctctctct cccaacccta gcaacgccag cagctctctg     1860
ggcgaggggc acagttgctt ccagttggca gaaccagtct cccagcttcc cttcagaacc     1920
cagcacctgc tgagccaccg acccacggac tgtctctctc tggaaggcag ccaccgaccc     1980
acggactgtc tctctctgga aggcagttca cctctgggtt tcaacactgc cctttcccct     2040
ttccttcttt agcccttagg aatccctgaa agcttcctgt gcttgtggct tctgtgactt     2100
ctcaacatct cttgtgcaca cacacacaca cacacacaca cacacaccag cctgtgtcta     2160
agcagttcat cctgtacaat gtctctctga taaaataact gattccattt ctgtcacctg     2220
ctgaggctcc agcagctctg ccctcagacc tcttaaagct gaggctcaga agcacaggga     2280
ggcacgggaa cctggtccca ggccctggct tgctggagcg aaggaatcta ttgcttcggc     2340
cactcggtca gaatccctcg gagattgatg tgatatgcac agtgacaccc aatcgggctt     2400
ggaaaactgg gccaacagtt aagccacaca aaggaactaa ccacagctcc actggcaact     2460
```

```
ggctccttgg caagtgccaa acaaacagc tgtggtgcag gccttccccg ggctgccggc    2520
ttcctggaca ctggcagagg ccgctcaaga agggagtacc tgagtagggt gttgttcagt    2580
tggtagaacg tttgcttgcc ttccatgaag cccagggttc tgtctgcacc tcatacctgt    2640
gatcctagca gttgggaaaa gacagcaagc acccggatca gaagttcaag accaccctcc    2700
cctttataaa gggatctgag gcagcctggg acatctgaat gacaaatgaa aagagccgtg    2760
agctatctgg tgttttcttc atggaagtcc aagtctcccc ctcattcctc ccaggattct    2820
ccgaatctgg ctgttgtctt tgcgatatt ttagaatatt ctagccagag cgcagagtat    2880
aaaatacaag tcaaaggcaa tgagcatatg ttagatggat ggaggagggc ctaaaaatgc    2940
tggtgctggg gaggaaaaat ggctcagcag ttaagagcac cggctgcttt tacagaggac    3000
ctgccttcag ttcacagcaa ccgcatgacg gcaactctgg ttccaggaaa tccaatgccc    3060
tcttctgacc tctataggca cccggcaagc acacagtgca cagacaatca tacacacgtg    3120
t                                                                    3121

<210> SEQ ID NO 25
<211> LENGTH: 1554
<212> TYPE: DNA
<213> ORGANISM: Artificial Sequence
<220> FEATURE:
<223> OTHER INFORMATION: Saf

<400> SEQUENCE: 25
ttccaagtaa ttagcacttt gcatctattt tatttattgc tactactaag aaaacataac      60
cgtgaaggca taaagcaaa cattttctgt agacacatga ggtgacacaa gagtgttgaa     120
acttctttaa ggataaaggc ctgatgttag gcatgtcgtg agcgcaaaac caatttctgt     180
gtaactaaat ttaaaagagt catattagag gggagaaatg aagataaac tgcaaaacgt     240 aaacaatgat tacttaggtg atagagttat gtctgatctt tgtatttgac tcatctgcat     300
ttataaattt tatttaataa gccttaattt cctaggccat atatcatata caaatataag     360
ttatacctaa cttataggta ttataatatg tatatataca taaatgtatg aatatttaca     420
tatgcgtgtg tgtgtgtatt cttttcagaaa agcaaagttt tcttcgggct ttaaacacgc     480
agcctctggt aaaggtgcta ttggtacaaa agttcaacaa gcatagctcc aagctttgac     540
aattttctta cactttacta atactgctgt ccaaaaacta tgagattttc aaagcagcca     600
acattgcagt ggtgcaatgg ttaataacaa gagagagaag agtgtggcct gaggttgtat     660
aaatgttttc tcaatcttga atcattaatt ttctccaagg aagttctaa agaatcccaa     720 atagtgcaca ctatttctga aaggaacagg atttttttt ctaatcataa aatggaccca     780
gacatctcag cctcttggtg taatctggat atcagatgca atcagcgaac agcctgagtt     840
ttggaattag atctgagttc aatcccatat ctcccattta ctagctgtgt gatcttggct     900
gaattactga agctctctga acctcatttc gccatctgta aaatggggat gtggttatct     960
tccccactac atggctctcg tgagaatccg cggagatcac atttgtaaac acttctctcg    1020
ctatgcctgg cactttgttg gggcccaata aaataaaaat ccatggactc tcagaggctc    1080
cggtactcaa atgagcctcc tggatccacg tctctttgat tagccatctg caagctggca    1140
tttctgagcg agggactttt caaaacaggc tgctcaagtt tcttggccaa taataggcgc    1200
cgggttctgt gcggtgggaa cgagtaccac caaccccagc aggagaccaa gcagaaatca    1260
ccatgggagt gcaagctaag aaagggcaaa agaagaaaga gaagggcaga aaaacaaaac    1320
```

```
aaaatgaaac cactcaggca gcgacttaca gtcttaaaga gagaattccc ggaagggaga    1380
caaggcagtt tcttttctg tgtgacaata aaaaacggta aacaagcctc cagaagctca     1440
ttcagccccc atataacttt tcgagaaag aaaaggtgcc gttcttccga gccctccggc     1500
ttaaccactg cttcggtgct gacttatttc ctacgtctga gaactgccag aaaa          1554

<210> SEQ ID NO 26
<211> LENGTH: 472
<212> TYPE: DNA
<213> ORGANISM: Artificial Sequence
<220> FEATURE:
<223> OTHER INFORMATION: snhg6

<400> SEQUENCE: 26
cctttcccgc gcgaccggcg agggaggaag aagcgcgaag agccgttagt catgccggtg     60
tggtggcggc ggcggagact gcgggcccgt agctgggctc tgcgaggtgc aagaaagcct    120
ttgaggtgaa ggtgtatgaa agtcatcata acagatgttt tccaaaaact tgtagaaggt    180
tgtgaaaaaa ctactaggat cacgcggcat gtattgagca tataggttgc tgtagatgaa    240
tgttcttagc tgtcatgttt aaaaatactt ctgcttcgtt acctcaagtg tggcatgcag    300
cattttggaa ggaaaattga agacgtgttc aagaaaacat gaacagaagc aaatgatgaa    360
aatgagcatt ttacttgatg ttgataacat cacaataaat tatggagaaa aatacatatt    420
tggctaactt ttaattgctg aacaataaag tgttttcttt taaatcaact ct            472

<210> SEQ ID NO 27
<211> LENGTH: 2998
<212> TYPE: DNA
<213> ORGANISM: Artificial Sequence
<220> FEATURE:
<223> OTHER INFORMATION: sox2ot

<400> SEQUENCE: 27
cctgctcagg gctgactgtg gcagggggaca ctctcctgct ggctctctct gtccacactt    60
agctggctcc tgtcctcagg tgcacggcca caccctcgca cccaaccttg atcctctgat    120
ggggaaggtc ccaggacttg tctgctggga caggcctcac ccccaagagc tctgggcagt    180
accgagaagc aaacctgaca gatttctcca gaacagtggc catccatggg atgagtgaaa    240
gcctcttcct attccaggga ttgcagaggc aaagctagac taggtcttgg aggctggtgt    300
aaggtggtgc gcggaaggca ggacgctgat gggagagact ggtcgaagaa aagcctaaat    360
ggattctccg tgctttggat ggagaaagag ggggaagtg cgagctcctt caactcgttc     420
tgtccggtga ggagtgatcc agcttgggct gacgagaggc tccggagcct tcacgttcag    480 tgcttttttac ctgccaatca aactgctaca agacaacacc ctgatctggc atggtcgccg    540
cgggtccaag cctgtagtcc caaatcggaa aatctctgca gctggtacac gcaaaagaga    600
agccaggcaa cagacatatt acagaagaaa gctctcaact ccgagatcga acctagaaat    660
tgtactttcc tcaagatccg cttaagagaa tctggttgat ggctttggtc tgagagttca    720
gacatctctt gtgcaactaa gaaagacctc attttccatt tgctggatcc tcctggtttg    780
tcatccctga gtcctgtaag aagctcatca ggaggtcccc tgcgccggaa ggaccatgtg    840
agctcatccc agatgatggg tggcaccatg gttttagcag ctcacacagt ggagaaccac    900
atttgctctg gaaagagctta gcaacatgta tttgataaca caacaaggtc agcttgagct    960
ctatccttct gtggccatac tgaacaaaag gagagacaga cagacagaca gacagacaga   1020
caggcaggca ggcaggcaag cagacagagg cagacagacagg cagacagaga cagagaaaca   1080
```

```
gagaaatgat tcctgaatta ttttaaaaa ttaattttaa aattcagatc aattaatcag   1140
taatacatgc ctgtagtctc agccctagaa cagatcaaac aggagagtct caagactaag   1200
gtcagcctgg accactggtg actgtttcaa agaaaacaaa ttaccatttg gcataatgg    1260 cacacgcctt ttaattccag tccttgggag gcagaggcaa gtgggtctct gagttcggga   1320
ccagcctagt ctacagagtg agttccaggt cagccagggc tatacagaga aaccttatct   1380
caaaccagcc aacaaaaccc acagcaaacc gaaaacaggt tatcctttaa aaagacgatt   1440
tagctgggca gtggtggcac atgcctttaa tcccagcact gggaggcag agggaggtgg    1500 gtttctgagt tcgaggccag cctggtctac aaggtgagtg ccaggacagc cgggactata   1560
cagagaaacc ctgtctcaaa aaaaaacaa caacaacaac aacaacaaaa aagacaattt    1620
agccagatat gatggctcat gcctttaatc ccagcacttg caaggtagac acaggcagcg   1680
agttcaaatc tatccaggtc tatatattga attccaggac acccaggggt acagattaga   1740
gagacttcat gtttaacaac acacacacac acacacacac acacacacac acacccca    1800 ctatgtgaat acacaggttt atgtgcatcc tatcccagag agcctgtggt gattataaaa    1860
cagtaaaaat agggcacagt agacagcacc ttcgagatca gcttagaaca cttacctgtc   1920
acttctgtgt cactttggt gtggcagtta ttatatttct ataattcatc ttttgaggga    1980
ggctcagaat cggtatgaaa tgatatatgt ttacctcttt actctgtgaa tcaggctctc   2040
atatagtcta agctggcctt gaactcctgg tatagcagag ggtggccttg atctgggagc   2100
aaaggtgctg tcatttccag cagagaaatg atatctagac caaagacaca gtttttatta   2160
tatagccaat gcttctttaa atgcctggca accctccctt ctgcagtgct tgatggtgtg   2220
ttactgaagg agttttccta aacaccagca caaatgaacg ggcacacatc aagcatacaa   2280
gacctggagg agggaggggg ccctgccgat tcctcagatg cagtgatgga tgagaaaagt   2340
aagggtggac cagagcagcc acagcattga aagtctgtgg tttcatttca cagaagtagt   2400
tgttcagctc tgtacttggt ttgccattgg cagtgttgta taggggggctg aggctcaaac   2460 ccaggcccctt accactaggg actgtcattc ttagccttcc aacctttaaaa acaaacaaaa   2520 caacaacaac aaaaacttat tttgattttc atttaatttc atattgcacc caggaactat    2580
tttaagaaat cttgtgtcat aacctgtgac caaaagttaa gtagcagttt tcctaatgtg   2640
tctgcgtttg ctataaagaa ttgaaactga gccaggcagt gttggtgcat gcctttagtc   2700
tcagcacttg ggaggcagta gcagatggat ttctgagttc gaggccagcc tggtctacag   2760
agtgaggaca ggacagccag ggctatacag agaaaccctat ctccaaagc cggaacaaaa   2820 aaaggtttga aactgtgtga gtatttttcat tgtctggcac tttataacag gtcttatttg   2880
gtattgacat tggtatttgg aatgagcatt tgaaggtttt aaaagcttca gtatttattt   2940
tgttctaaaa taaagtacct tttccctctg aaaaaaaaaa aaaaaaaaaa aaaaaaaa     2998
```

<210> SEQ ID NO 28
<211> LENGTH: 7528
<212> TYPE: DNA
<213> ORGANISM: Artificial Sequence
<220> FEATURE:
<223> OTHER INFORMATION: tug1

<400> SEQUENCE: 28

```
tcctgctttc ctgaccctct ccgccattta aagaaacagt accggggggcg ggccgagcga    60 cgcagccggg acggtagctg cggtgcggac cggaggagcc atcttgtctc gtcgccgggg   120
```

| | |
|---|---|
| agtcaggccc ctaaatcgaa gaagccctgg cgcgccctcc cccctcccg ggtctggtag | 180 |
| ggcgaaggaa cgggcgtgcg gtcgatcgag cgatcggttg gcggctcttt ctcctgctct | 240 |
| ggcatccagc tcttggggcg caggcccggc cgccgcggcg cgcgcccggt ggccgttggc | 300 |
| gctcgcgccg cgtctttctt ctcgtacgca gaactcgggc ggcggcctat gcgtttgcga | 360 |
| ttcgacgagg agtcgtccgg gtggtcggcg gcggcgggca gctgctccgc cccgctccgg | 420 |
| gggaggcggc ggcggcagcg gccgcgggat tggagcggc cggggaggcg ggggtggccg | 480 |
| gggccggctt ggaggcctgg cgccaccctt cggggcctgc aaggacccag ttgggggggc | 540 |
| aggaggggc cggaggatgg ttggttgtgg gatttctact ttgccttttc ctccttatgc | 600 |
| cgccttagtg aggggcggga gctctggcgg cagccccggg gtggggagac gagctccgga | 660 |
| gtcggaagag ctgggttttc ttccgggcct agccaccagt tggcggagtg accttaggcg | 720 |
| agtcactctg taatttgtct gcgcctcagt ttcctcctct gcctatcaat gtgtgtgggg | 780 |
| ttgaaatcgc tttgtaaact ataaagcgtg ggtgtacgta aaggatggtt attgtttata | 840 |
| atttttttg agttgtaaga aaacttagca gttccccaat ccttgggttt tgaacctggg | 900 |
| aaccttggat tggagttggg gatccccaaa cttcctgaaa ttgtgggaat gtgcggtttg | 960 |
| ggggaatgat gggaatttgt gggaatgtgc gttttagggg aatgatgatc catcgctagc | 1020 |
| aagttttcca aggggctgt gacccagaag agttaagaat cacaatttct tcatgctaca | 1080 |
| gagaggaaac tgaggcctag atgtcatttg ggacccttca caaccatttt gaagccctgt | 1140 |
| ttgagtccct gggatatgtg agctgtttct atgcataatg gatattcggg gttaacaaca | 1200 |
| gtcccctgct tggcttctat tctgaatcct tttctttcac catggggtgc ctgaagggtg | 1260 |
| gctgatgcat atggtacaat ggcacccagt gtaaagcagc tacaattagg agtggatgtg | 1320 |
| ttctgtagca tccatttaa ataagcctat tttatccttt ggcccgtcaa ctctgttatc | 1380 |
| tgctgcttgt actggtgcct gtacttttct gactctcatt gaccatattc cacgaccatg | 1440 |
| gttgtcatcc attacttgat cctactttac atgtctaggc tgtgtggttg gtggtgaata | 1500 |
| ggcttctttt tacatggtgc tgccagccca gctaattaat ggtgcacgtg gacttttagc | 1560 |
| aagcgggctc actggaagag actgaacctg gcatggaatt cctgaagatg tttgggggttt | 1620 |
| ttttctttct taatcgaaag ttaacattgt ctgaaaagtt ttgttagaac tactgcggaa | 1680 |
| cctcaaaatc agtagatttg gaagtgattc aaagctaaac ttttttccttg gccctccttg | 1740 |
| tgttctaatt gcttgcaagt gtaatactag gatgtccaag atgccagttt tgcttctttt | 1800 |
| gttagttgtc agctgctttt atcaaatttc aggccattat ccaacaaaca ctataaaaat | 1860 |
| gtttgaacaa ttggatttca aacatttttcg ttttgtggag tggtgctcac caagtggtac | 1920 |
| agccctaagc aagtgaacac aaacacattt aagtgtattt tgtctgatta gatgttagcc | 1980 |
| agttatgcta tttcattcaa atgtctgaaa aaatcaattg actattccct tttcctaaag | 2040 |
| ggcagagaca gataatctca cttccagaga aatgacttgg agaaaaaaaa gtgttggtct | 2100 |
| ttttgctctt ttgtaattaa atccggatgt acctcaaaag acttaagact gtggtgataa | 2160 |
| gatgctttcc tcagcagaaa ggagggaaaa aaaacaactg gaactcaaag cttgaaattc | 2220 |
| tgtggcaaaa catgagatgt ccaggattgg aggttgaaaa gatttcacta cagtgttctg | 2280 |
| caatagttgg agcagataac tttcagtgta gccacagcca tggactccag atttccagat | 2340 |
| tttcaagacc tggacctgga acccgaaaga gcttgtcacg atgcggcagg aacactggag | 2400 |
| gtagattttt ttttatttt gaattttggg actgttgacc ttgctgtgag aaaagagaca | 2460 |
| acgactgagc aagcactacc accagcactg ttactgggaa ttagaagacc tgagtttctg | 2520 |

```
tccagaccct cagtgcaaac tgaggatgct ccatccaaag tgaattatgt cctgtgcctc    2580
ctgattgctg agtgttcacc tggaccttct gactaccttc cctgtgctat tccatcagcc    2640
tacagacctg gtacctggat ttttgcccga gatgattcct accaccttac tactgacgaa    2700
gacacccatt ccagtggacc actgtgaccc aggaggcatt cagccatcat gatgtggcct    2760
ttacctccac tcctgtcttg ttctacccag attcagcaca gccctttata gtgaagtcag    2820
agtcctcaag ccaaatagct aaagctgttt tatcacaaca aaggcctagt ttgttccatg    2880
agtgtgcatt tcatttcttc agttaaagcc ttcagagaca cacaataaat ttggaccagg    2940 ggattttta gttattaatg ctctctgaag aaaggcaaca tcttttgag agcagcattg    3000 gaccacaccc cacaatctca aatgattgaa attcatgaac atctaggatc ccgtgaaggt    3060
cactggaccc tgttttttct acttcaaatc ctgtagtagc ctactgaatg agaaaacata    3120
ttctgaccca ttgggatcaa atcaaaggca cagtgaactc ctcatagcat cttctttgga    3180
attactcagg aaccagaact ttttacacaa atgtaagaaa ttctaccaag gagtcccctt    3240
acctaacagc atctcacaag gctgcaccag attccagaaa aggcttctct tgatacatca    3300
agcattttgt gaccgactta ttcttagatc attggttttc caaaggcttt gtggccatga    3360 agcccttga gtgaaaactg tgcagaagcc cagagtaaaa gtgaagctgc tctggatgaa    3420
gtagtgaagc aagagtaggg gcctgaatcc tgctacaact atcttccttt accaccgtgg    3480
tgacacctaa ggggacttcc ttacaacacc ttgaactctt ccgaacacag tttgaaaacc    3540
actgccccag acagcaatat gtttgacctg aatggcattc caatcttttc tgtacctcca    3600
ctcagcacag ttcatgttca gtagatgctg aacattctta gaaatactgt gtgtgaactt    3660
agaaaagtgc aagaagacag gcatgtcttt gaccccagga atgatcattt gctgaagatg    3720
gtgtcaagtg aacctagatt aacagccctc cactccagat ggatatccag tgattcctag    3780
aatgggatat agccagagaa caattctatg caccctacac tgacagactc ccttaagcaa    3840
caccagatgc tctactggta cttgaagtac atgactttga agtcttgacc ctccatgaat    3900
acctgaatta tcagcaagcg ggttttgaag ctggtgcctc attgaggcca tattagagca    3960
acttgtacat ttgacctctt gttatcagcc atggtactct acttcgtgtg caagagataa    4020
ctatgaaagc caaattcaaa tactggcaac atttcctaaa ggggctcaat atctatcatt    4080
cgtcttcttt tccaaactac acatcactgt atgactcaac cagtagcagt tatattgccc    4140
cttggttttt attcagttta actactgttt ccaagataaa tgagctaata agctttaaaa    4200 aaaaaaaaa aaaggctga attctttttt cttcatcact ggcatatctg cctattctcc    4260
agaattatta tgactattca gctcacttta acagttgaac ttcaagcgac aatctttgaa    4320
caccccttct catgtgattt aaaatgaaac catttggaaa agtttcttct agccagtaat    4380 agatttttt tttaattgct ctgccttgtg ccgagagatg ttctttaag atgaatcttt    4440 tgatgtctga taccaccaaa tataggtggt agggagagtt ggaggctggc cctttgagca    4500
ggccattagc ttacttgctg gcatttccg atagcttatt gcctaccttt tgctggaaa    4560 caaactgatt tgaaaacaa aatctatgaa gactgcagct aaggatttta tcggtagact    4620
taagagcttt tgtccttgtg gatattttag tggaaccaca tcagtctcaa tactgtcatt    4680
ttacactgac tcagagcagc tgacttcatt ccttgccatg atatatattt aaggcaggca    4740
ttgtaacaga cataaagaca acttatctgt ttcagcagga aggattcagt ttatgaactc    4800
tcagaccaga tcatgttgaa caaggagact ttgatgtgtg tcatgagaaa actcattctt    4860
```

```
tacttcccag tcaatttaaa ggccagctat cctgagctac tcgaatgaat gcactggtta    4920
aacattggaa atagtttgtt tatatccttg tctctctcta ggccaattgt gattacatga    4980
ctcgactcta catctcgtca aacaaggcct aggtctggtt gctgtagact gctcgccctc    5040
aacaaataaa atctggttga ctagcctcct tgtatataca actattattt gttaagaaga    5100
aattatcgtc aattttctac taccttccaa ttgtcagctc ttttttttcct ctctggtttt    5160 tcctatactt tacagaaaaa gacattgatc tatactgcca ttccctctaa tcctgccata    5220
ctcagtcaaa aggaatgact taagatgaag atgatcatct gctcgagtct aaaatataca    5280
ttgtatataa gaattggtga ttagaaaagc aaaaaaccta aaacttaaat ctaggagtct    5340
gtatactgtc tccatgtctc catgcctcag atctcatcta aatctttgaa cagcaccatt    5400
caaccaatct gaggccttga cttgcttgta agatgattct cagagatcgg ctgagttaaa    5460
aaagatgacg acttgattac caaagaaagt agggccaact ttgacaaatc tggctctgct    5520
gaccctgtca ctcccagatg tagcatagac tcctaaacag aacctcaagt ctgattgagg    5580
ataaggcctt ctcctgagct gaaagttctt tggcagatga gcaagaaact gaaagctgat    5640
gtacctgact ggctctgtaa gatcagaaaa ctgtatccag aataagccct atggattaac    5700
ccctgagtac ccagagtaaa aactaattta cagaacttcc ttattgatct gctggttctt    5760
ccagatcata ttctggctat tggtatggct ggccttctg aaggtacccct gcttgtctat    5820 tttcctgact cagctcttgc ctgccttttt cacatgttgc tgcaattaga ctcaccgtga    5880
ggactacagt caatttcagt ctatcttgtg cccaatacaa caaggatttt taatagtaac    5940
aacccacacc tcacccacta ggactcaatg ttcacaacag aaggaccat tgctgcatac    6000 tccttgacca gcaactttt tgaagatatt tttaagtgca gagtaggcct ctattcctgt    6060
atgtaattgt tcattttcag cacctggaac ctcatctatc gggtctggaa ggaatacagc    6120
agttcgaaag ccgcgtccat ttctctcctt cagtagtgca gaaatgagtc cgattcacca    6180
gtacacacag aactgtacca gttcaaccta gcaaagaag aaaagtttcc actgtactta    6240
aaatttacag ctgactcaaa ttgcctcaca gaattatttg atgtagaagg ctagttgtct    6300
tacttcagat cagcaggaca gttgggctct cagactcatg accactgagt ttgcttgtgt    6360
tgaaactgtg gtttcatcca acatatgcta ttggacatga ttattattcc attcaaatgg    6420
attacagact tcttgaggac aggacaaact tatctctcat ggtgtttttt tagaatactt    6480
ttataaccaa ggaagaaacc atgccagctg ttaccattca acttcttaag cagagattaa    6540 gcttttcat atctgttctt atcctggaca tcagtagttt ttaattgccc agcatccgtt    6600
ccatcttgta acaactccct gatgtttctt aaaaccacct cttcctattt tcagtctgtg    6660
gtttggacag tctgacccaa ccttgagctt tgtgggtgaa catgtaattc agacctcatc    6720
aatcagcaaa tccatctgaa ctgtggagga gaagctctct ttactgaggg tgctttagct    6780
ttgtaggatg aaaaccctcaa actaacaggg cctaccatgt agagaatgaa gccagtgcag    6840
gggaaagcag agccaaaata tggagagact tgaatcctga tgacagcgtt tgtgcccctg    6900
gatccaaccg tgcctgaagc tagaatatcc cctggacttt tcagttatgt gaaccaataa    6960 atacccttt ttgcttaagt tactttgagt tgggtttctg ttacttgaaa ttgaatccac    7020
actaatatat ctaccaacat tgagacttga cagatccaag tatttattaa gctagaggtc    7080
atggtcactg aaattacttt ccaaagtgga agacaaaatg aaacaggaac tgagggaata    7140
tttaagatcc cacagaagcg taaaaatgac atggtagaaa gtaatagaaa acctaaatgt    7200
ctgtcattaa aggataggtt aaggtgtggt tcagccatat aggaatatct cgtatctgtt    7260
```

```
aaaatgaata aagtacattc attgtgtatg gaaaaatggc catgatacat taggtgaaac    7320
aagttattaa tagaaaagtg tacagtgtga actcatttta aaatgtgtgt gcttatgttt    7380
ataaatgcat agaaaggtct attcacagct ttctttgaac agtgtagatc acatgaaact    7440
ttcaacttta tacatttctg tattaatatt ttacactacc cacattattt ttaaacttta    7500
ttttaaataa agaatttta aaattaaa                                        7528
```

<210> SEQ ID NO 29
<211> LENGTH: 332
<212> TYPE: DNA
<213> ORGANISM: Artificial Sequence
<220> FEATURE:
<223> OTHER INFORMATION: 7SK

<400> SEQUENCE: 29

```
ggatgtgagg gcgatctggc tgcgacatct gtcaccccat tgatcgccag ggttgattcg     60
gctgatctgg ctggctaggc gggtgtcccc ttcctccctc accgctccat gtgcgtccct    120
cccgaagctg cgcgctcggt cgaagaggac gaccatcccc gatagaggag gaccggtctt    180
cggtcaaggg tatacgagta gctgcgctcc cctgctagaa cctccaaaca agctctcaag    240
gtccatttgt aggagaacgt agggtagtca agcttccaag actccagaca catccaaatg    300
aggcgctgca tgtggcagtc tgcctttctt tt                                  332
```

<210> SEQ ID NO 30
<211> LENGTH: 200
<212> TYPE: DNA
<213> ORGANISM: Artificial Sequence
<220> FEATURE:
<223> OTHER INFORMATION: BC200

<400> SEQUENCE: 30

```
ggccgggcgc ggtggctcac gcctgtaatc ccagctctca gggaggctaa gaggcgggag     60
gatagcttga gcccaggagt tcgagacctg cctgggcaat atagcgagac cccgttctcc    120
agaaaaagga aaaaaaaaaa caaaagacaa aaaaaaaata agcgtaactt ccctcaaagc    180
aacaaccccc ccccccttt                                                 200
```

<210> SEQ ID NO 31
<211> LENGTH: 1529
<212> TYPE: DNA
<213> ORGANISM: Artificial Sequence
<220> FEATURE:
<223> OTHER INFORMATION: EgoA

<400> SEQUENCE: 31

```
caacttctgg gcaaggcaga ggtgggtttg gcttttaaa aattttttca gcctgtcctc      60
atggaactac atattctttt ctaagaactt ttcatcctaa cctccctact cacatcttct    120
aagtgtctct gctctggtgg gaatgtgatg gacaacacag agccatctca gaagcctctg    180
tggccaccac caggccggcc agggtgcagg gggccactcc ctgggcagcc atagggttct    240
cagcaaggtg cattcgtcgt ccctgctgag aatctgatgg ggcagcattt ttttttttaa    300
ttaaatgcaa gctgagtcat ttcaacctgc aaccttcagg taacaggagt tacccaagct    360
ccaggaatta tgattgtggg gtaaacccat tctcttgttt tcttgcggtt ctattttata    420
acgcactaga gggacagag acgtcattgc ttcacccagg gcaagaggac aaaggaggat    480
gcatggaaat acaaacagcc cttctcctcc aggccatacc gactgtccaa ctagcaacag    540
```

| | |
|---|---|
| acttcacctg gttttggagc aatctgaatt tggaatatgc cagagaaaac ttctatcagg | 600 |
| caagatggaa gactcctagg ataggtctct ctcatggagg gattggcacg atggtaagag | 660 |
| tccagtggat ggaaaaggcc tcctccttaa agatggtgat ggaaacgagc actgcacagg | 720 |
| gaaacacaaa tcaggtcccc tgaaatccag cccaacctgg ccagaccctc cagtgcccat | 780 |
| cagggcttat gaacagggtg cttcagtgtc tttgttaggg gtggttaaaa aggagcacgt | 840 |
| gcttataggg gatgctgctg agctccatga ttttgacttc ctgtctaacc tgttgatgct | 900 |
| acaaaactct tttaaaaaca gttaccatgg gaacttttcc ctagcaagca ttcttcaaga | 960 |
| aacgttacag gtgctggtga attcaatgcc cttggtgtca ataagctttt gctgagtctt | 1020 |
| agaatgtgtg gcttgaactg agaggacttt caaacagata atgcgaagtt tccaatgcaa | 1080 |
| atgtcttcgg ggttaagtgt cagtgaagtg cagtggaagg tagggggata aaatgatctc | 1140 |
| agtgtatatg gaggccccac ttaagcattc aaaaaattct atatacagtg ttttcaatgt | 1200 |
| attatgtatc agcaaaacaa ataccccat agggctataa tcagctcagg gggtcacctc | 1260 |
| agcaagagat gctctggcta tcactcctac tacgggattt cctctctcat cagaaccagt | 1320 |
| aggtggtcaa aaccacaata atgcataaat gaaggcaggg aattgggtat ccaatgtgag | 1380 |
| caactgaaaa ggtgccatgt attagctatt tgccattatg gttctgcaag tgctcagatg | 1440 |
| actcataaaa tgaccagaac aaaaaaaaaa aaaaaaaaa aaaaaaaaa aaaaaaaaa | 1500 |
| aaaaaaaaaa aaaaaaaaa aaaaaaaa | 1529 |

<210> SEQ ID NO 32
<211> LENGTH: 1529
<212> TYPE: DNA
<213> ORGANISM: Artificial Sequence
<220> FEATURE:
<223> OTHER INFORMATION: EGOB

<400> SEQUENCE: 32

| | |
|---|---|
| caacttctgg gcaaggcaga ggtgggtttg gcttttaaa aattttttca gcctgtcctc | 60 |
| atggaactac atattctttt ctaagaactt ttcatcctaa cctccctact cacatcttct | 120 |
| aagtgtctct gctctggtgg gaatgtgatg gacaacacag agccatctca gaagcctctg | 180 |
| tggccaccac caggccggcc agggtgcagg gggccactcc ctgggcagcc atagggttct | 240 |
| cagcaaggtg cattcgtcgt ccctgctgag aatctgatgg ggcagcattt tttttttaa | 300 |
| ttaaatgcaa gctgagtcat ttcaacctgc aaccttcagg taacaggagt tacccaagct | 360 |
| ccaggaatta tgattgtggg gtaaacccat tctcttgttt tcttgcggtt ctattttata | 420 |
| acgcactaga ggagacagag acgtcattgc ttcacccagg gcaagaggac aaaggaggat | 480 |
| gcatggaaat acaaacagcc cttctcctcc aggccatacc gactgtccaa ctagcaacag | 540 |
| acttcacctg gttttggagc aatctgaatt tggaatatgc cagagaaaac ttctatcagg | 600 |
| caagatggaa gactcctagg ataggtctct ctcatggagg gattggcacg atggtaagag | 660 |
| tccagtggat ggaaaaggcc tcctccttaa agatggtgat ggaaacgagc actgcacagg | 720 |
| gaaacacaaa tcaggtcccc tgaaatccag cccaacctgg ccagaccctc cagtgcccat | 780 |
| cagggcttat gaacagggtg cttcagtgtc tttgttaggg gtggttaaaa aggagcacgt | 840 |
| gcttataggg gatgctgctg agctccatga ttttgacttc ctgtctaacc tgttgatgct | 900 |
| acaaaactct tttaaaaaca gttaccatgg gaacttttcc ctagcaagca ttcttcaaga | 960 |
| aacgttacag gtgctggtga attcaatgcc cttggtgtca ataagctttt gctgagtctt | 1020 |
| agaatgtgtg gcttgaactg agaggacttt caaacagata atgcgaagtt tccaatgcaa | 1080 |

```
atgtcttcgg ggttaagtgt cagtgaagtg cagtggaagg tagggggata aaatgatctc    1140
agtgtatatg gaggccccac ttaagcattc aaaaaattct atatacagtg ttttcaatgt    1200
attatgtatc agcaaaacaa aatacccat agggctataa tcagctcagg gggtcacctc    1260
agcaagagat gctctggcta tcactcctac tacgggattt cctctctcat cagaaccagt    1320
aggtggtcaa aaccacaata atgcataaat gaaggcaggg aattgggtat ccaatgtgag    1380
caactgaaaa ggtgccatgt attagctatt tgccattatg gttctgcaag tgctcagatg    1440
actcataaaa tgaccagaac aaaaaaaaaa aaaaaaaaa aaaaaaaaaa aaaaaaaaaa    1500
aaaaaaaaaa aaaaaaaaaa aaaaaaaaa                                     1529
```

<210> SEQ ID NO 33
<211> LENGTH: 2322
<212> TYPE: DNA
<213> ORGANISM: Artificial Sequence
<220> FEATURE:
<223> OTHER INFORMATION: H19 upstream conserved 1 & 2

<400> SEQUENCE: 33

```
ggagggggt gggatgggtg gggggtaacg ggggaaactg gggaagtggg gaaccgaggg      60
gcaaccaggg gaagatgggg tgctggagga gagcttgtgg gagccaagga gcaccttgga    120
catctggagt ctggcaggag tgatgacggg tggaggggct agctcgaggc agggctggtg    180
gggcctgagg ccagtgagga gtgtggagta ggcgcccagg catcgtgcag acagggcgac    240
atcagctggg gacgatgggc ctgagctagg gctggaaaga agggggagcc aggcattcat    300
cccggtcact tttggttaca ggacgtggca gctggttgga cgaggggagc tggtgggcag    360
ggtttgatcc cagggcctgg gcaacggagg tgtagctggc agcagcgggc aggtgaggac    420
cccatctgcc gggcaggtga gtcccttccc tccccaggcc tcgcttcccc agccttctga    480
aagaaggagg tttagggat cgagggctgg cggggagaag cagacaccct cccagcagag    540
gggcaggatg ggggcaggag agttagcaaa ggtgacatct tctcgggggg agccgagact    600
gcgcaaggct gggggttat gggcccgttc caggcagaaa gagcaagagg gcagggaggg    660
agcacagggg tggccagcgt agggtccagc acgtggggtg gtaccccagg cctgggtcag    720
acagggacat ggcaggggac acaggacaga ggggtcccca gctgccacct cacccaccgc    780
aattcattta gtagcaggca caggggcagc tccggcacgg cttctctcagg cctatgccgg    840 agcctcgagg gctggagagc gggaagacag gcagtgctcg gggagttgca gcaggacgtc    900
accaggaggg cgaagcggcc acgggagggg ggccccggga cattgcgcag caaggaggct    960 gcagggctc ggcctgcggg cgccggtccc acgaggcact gcggcccagg gtctggtgcg    1020
gagagggccc acagtggact tggtgacgct gtatgccctc accgctcagc ccctgggggct    1080 ggcttggcag acagtacagc atccagggga gtcaagggca tggggcgaga ccagactagg    1140
cgaggcgggc ggggcggagt gaatgagctc tcaggaggga ggatggtgca ggcagggggtg    1200 aggagcgcag cgggcggcga gcgggaggca ctggcctcca gagcccgtgg ccaaggcggg    1260
cctcgcgggc ggcgacggag ccgggatcgg tgcctcagcg ttcgggctgg agacgaggcc    1320
aggtctccag ctggggtgga cgtgcccacc agctgccgaa ggccaagacg ccaggtccgg    1380
tggacgtgac aagcaggaca tgacatggtc cggtgtgacg gcgaggacag aggaggcgcg    1440
tccggccttc ctgaacacct taggctggtg gggctgcggc aagaagcggg tctgtttctt    1500
tacttcctcc acggagtcgg cacactatgg ctgccctctg ggctcccaga acccacaaca    1560
```

| | |
|---|---|
| tgaaagaaat ggtgctaccc agctcaagcc tgggcctttg aatccggaca caaaaccctc | 1620 |
| tagcttggaa atgaatatgc tgcactttac aaccactgca ctacctgact caggaatcgg | 1680 |
| ctctggaagg tgaagctaga ggaaccagac ctcatcagcc caacatcaaa gacaccatcg | 1740 |
| gaacagcagc gcccgcagca cccaccccgc accggcgact ccatcttcat ggccaccccc | 1800 |
| tgcggcggac ggttgaccac cagccaccac atcatcccag agctgagctc ctccagcggg | 1860 |
| atgacgccgt ccccaccacc tccctcttct tcttttcat ccttctgtct ctttgtttct | 1920 |
| gagctttcct gtctttcctt ttttctgaga gattcaaagc ctccacgact ctgtttcccc | 1980 |
| cgtcccttct gaatttaatt tgcactaagt catttgcact ggttggagtt gtggagacgg | 2040 |
| ccttgagtct cagtacgagt gtgcgtgagt gtgagccacc ttggcaagtg cctgtgcagg | 2100 |
| gcccggccgc cctccatctg gccgggtga ctgggcgccg gctgtgtgcc cgaggcctca | 2160 |
| ccctgccctc gcctagtctg gaagctccga ccgacatcac ggagcagcct tcaagcattc | 2220 |
| cattacgccc catctcgctc tgtgccccc cccaccaggg cttcagcagg agccctggac | 2280 |
| tcatcatcaa taaacactgt tacagcaaaa aaaaaaaaa aa | 2322 |

<210> SEQ ID NO 34
<211> LENGTH: 2794
<212> TYPE: DNA
<213> ORGANISM: Artificial Sequence
<220> FEATURE:
<223> OTHER INFORMATION: HAR1A

<400> SEQUENCE: 34

| | |
|---|---|
| gggagtgttg aggggggcctg aagggttccg ctcctcccac ccagggaacc gccatgccac | 60 |
| tagtgggctg tcctggagac tcggggagaa agcacacagg ctgtcgggaa aggtgggtcg | 120 |
| caggcgggca gggcagccct gctgtactga tgggcaggcg ctgggtgggt ggaaggcaaa | 180 |
| gccatcaggt catcccctc tctgtccctg cattgggcca accaggtgtg tcaggaggat | 240 |
| atttgaccat tcctgagagg cacattctct ctctctctct ctctctccct ctctctctct | 300 |
| ccctctctct ctccctctct ccctctctct ccctctctct ccctctctct ccctctccct | 360 |
| ctctctctcc ctctccctct ctcccccctc cctctccctc cctctcccc tctccctctc | 420 |
| cctctctccc cctccctctc tctccctctc tctccctctc tctcccccctc tctctccctc | 480 |
| ctctctctgt cacacacatt tgcacatcct gcagtgtgaa tggagtatga atgtgtgtgg | 540 |
| taggcgacag ctgtgtgtgt acgtccgggt gcgtgtgtgc gtgtgtacat gtgagcgtgt | 600 |
| gtgcacgtga gttagagcct gagtgtcccc tgcgtgggtt agtgtgtgcg cccgcccggt | 660 |
| gccctccgtc ttgggagtct gggctgctgc tccgcgggct ctggagccgg cgctccccac | 720 |
| gagcccggac tctccgccgc gcccgggagc tgcgcaatcg gctgctaaga cgccggcgcc | 780 |
| accggctggg ccctgttctc ccctctcttt tctacagtct tacccgcagc tgacagggtt | 840 |
| cgaaagagca tgaaacggag agacgttac agcaacgtgt cagctgaaat gatgggcgta | 900 |
| gacgcacgtc agcggcggaa atggtttcta tcaaaatgaa agtgtttaga gattttcctc | 960 |
| aagtttcaaa tgaggcgaat cccgttttcc gcgatgctgc agcgcgcggg ttttaaccgc | 1020 |
| agggtcacgc ggaacgccgc gccgcgcgac tgtgcctcgg tctctgcgcc cggctctccc | 1080 |
| tccggtccgc aagaggagga aggcccgcgg cgtgccgagg tcagcggcgc ggagccacca | 1140 |
| ggcgagacgg tcacggacgc ctgaaccgag gtcaccgagg ccacggggcc gggaggccct | 1200 |
| cagcagagcc cggggctcc gcacctcaag gccggccagg aagaaacagc agcaggagcc | 1260 |
| cagggcgccc cggggagccc ccgacacgcg ggccgagcgc ccagagcggc ccaggccctc | 1320 |

```
gcgaggagac cggcctcccc agggcggggc ttccgactcg ggcgcccgtg agccccggag   1380
gcggcgcgaa ggggcagagt ccgcgtttct aaccagcccc cgggtgggcg gtggcccgcg   1440
cggcacggtg ggcgcgagcg ccgtgggctg gggccggcct gggctttcag ggcgagggct   1500
ttccgcgccg gccccagccc accggccccc gctgcgcgcc cctcacgctg cagcctggga   1560
acctgggccg ggagctgcgg gccgctccgg ggaagcgggc ctgacctccc ctccccaccg   1620
ccgcccctgc ggtgagatcc tgcctgccgg ggcgcagggg cccgcggttg ggctccggga   1680
gacggaagag gccccacagc tcgggcccca cgcagtggac gctgccactt aattttggcg   1740
taattgatgt caaggcgggt gcccgggccc ccagtgaaat gcctcatgaa ctcgctgcga   1800
ggaacggcgc tccacgcggt gcacggtggc caatcagagc tgccgcttct gatggaggct   1860
gagccggctg ggaggcgtc ttggccaaga accagcccca gcctcgctca gggccccaac   1920
ccgcagacca tgtaattaag ctgcgttctg cagccagggc aagagtctca gctctgaaca   1980
tcttcccgca cctctgagga gccaggcctg aaaccctct aaaatagatt tttctgcctc   2040
aagacagaag atgggcgttc caggcagaga agagctgccc agtcacgtgc tctgctccac   2100
ctggtcagag acccttgacc tttagaagac tggacctgag ggcgtggctg gtggacctga   2160
gggcgtggat ggtggacctg gccacccagc tgtagctttt tgggttcctg tggtcccatt   2220
tcttgggtca atctcacacc tggcagctcc caggaagaca ccccaggcc ctcacactc   2280 ctggggggcag ctggaattgg cttcagggcg ggaccagggg cccatgggt gtttggaatc   2340 cctgatctgg gtcaggcacc ggcagcagga ttccagcctg gcctggactc tggtgtgtcc   2400
cgtttgaaga acccccgccc tgtgaaagtt caagtttagc atccaatgac ccatttaaga   2460
ggtttgctga gccacgtcac aggagggtct gggtgcaaac ggaggtggca acacacagag   2520
cgagccttga gcacccaggt taccccccagg acctccagtc tggcttgggg gctcctgctg   2580
tcctgtggag cagcccctg ggatcaggga cggggctgag ctggagagtg tgcaggattg   2640
attaatgatg tctgccacgg tcaggccaac tgctgtgttt ctggggccca caagctaaaa   2700
atggttggaa aaaatcaaa acattaatat ttgtgacata tgagaatgct atgaaagtca   2760
actttgctat ccataaataa agttttattg acat                              2794
```

<210> SEQ ID NO 35
<211> LENGTH: 896
<212> TYPE: DNA
<213> ORGANISM: Artificial Sequence
<220> FEATURE:
<223> OTHER INFORMATION: HAR1Bm

<400> SEQUENCE: 35

```
gtgaccctgc ggttaaaacc cgcgcgctgc agcatcgcgg aaaacgggat tcgcctcatt    60
tgaaacttga ggaaaatctc taaacacttt cattttgata gaaaccattt ccgccgctga   120
cgtgcgtcta cgcccatcat ttcagctgac acgttgctgt aacgtctcct ccgtttcatg   180
ctctttcgaa ccctgtcagc tgcgggaagg aacttctaaa ctaaaagctg gcaagactca   240
gcagaaaaaa aatatcgaaa gctgcttctg ctgccccagc ttcactcagg ccctggctgc   300
tccttcactg gtctacactg ctgcctcctg gaacacccca ctctgcaacc aggtctgatg   360
cccggtgtgg acattcaggg atgaggtccc ctggggctaa atgaatgaac agattctgaa   420
aagcagaagc tacgtccggg ggtctctggg ccacaaatca ctttctgacc tgcagccgtg   480
aggcgtgagg ctcactcgga agctcccgga acctggagac tgccctcact caacacttga   540
```

| | | |
|---|---|---|
| acaagcaagg ggccaggttc aatgaaacac ctgcccgccc ggcacaccag gctcaaaagc | 600 |
| aagcaagcaa gcaaacaaac aaacaaaatc aaatcaggcc ttcacaactc cccaaatcat | 660 |
| gtgtgagttt ctacagagca gaagccaaaa atatatgtta tctaactagg tcctatttac | 720 |
| atatatttt atggctgctc taaaaaatta tcacaaacat agcggcttca ccccgtttcc | 780 |
| cctgttgtga ttattacaca ttggatgcct gtatcaaaat atctcatgga ccccataaat | 840 |
| agcaacaccc tgtatgtact catgacaatt ttttaaaaaa gaacacttac actttc | 896 |

```
<210> SEQ ID NO 36
<211> LENGTH: 1628
<212> TYPE: DNA
<213> ORGANISM: Artificial Sequence
<220> FEATURE:
<223> OTHER INFORMATION: Hoxa11as

<400> SEQUENCE: 36
```

| | | |
|---|---|---|
| gccacctcag gggaagcaac agatcgtcac tcggtgttct caccgaaagc acgtaatcgc | 60 |
| cggtgtaact catgttggct gggggggcctc ccggcgcgcg cggagaggct ggggtgcgcc | 120 |
| cccatgcagc atgcttgtgc tcaattgcag ggtcctcgtt ctcgagtgtg cagagggcgg | 180 |
| tgagagctca actctcgtcc ccacctccca cccgcagctc cccgggtggg tgagggatgc | 240 |
| cctggactgg ggatagccag gtgggagtcc gtcgctgtgt ggcctgtggt ctcggagtct | 300 |
| gttctcctgg agtctcgcat ttgcaccccc ttcttcgcag tcccctccc atagacttgc | 360 |
| tctgggaagc gcctctgcct ccgaccctag ccggaacccc ttcggggcca gagtttgaag | 420 |
| ccgtggatgt gcctgcctgg tggcttgtcc gatttgcacg gtgacttgat tacactctct | 480 |
| cattcatggt cacttccgaa gcgctttagt gccttccgtc cctaaaccgc caacagccag | 540 |
| aacggcttct ccccgcggtt tgtcactgat ccgcagggcc cggaagggcc ttcgtcttac | 600 |
| ccgggatcca cctctccct catcttccct gcctacctct tcatcccacc ttctgtcctt | 660 |
| ggagaaactc cctcctcctc gctgcctgcc gggcttcgga gtgactcggc agagacagag | 720 |
| gcacaggggc tgccctgctg ctcaccggtc cacccatctg cctggtcttc tggagctgag | 780 |
| gactcgggaa accatgcaat tgaggcaagc cttgggctgc tttagaggcg ctgacatccg | 840 |
| aggagacttc tcctgggagg tccaacagcc gagcttagcc caccgggctc tgggaaagac | 900 |
| ccgactgagg ctaaagccgc cccggaaggc caagtccgag ttccatttct tgaagaggcc | 960 |
| ggcgcgcgta aggctgtgac attggccctg gcgactggct tcccaggagc tgttctttct | 1020 |
| caggagctcc acagcgcggg ccatctccag aaaactgtct tcagagtgta tttccttta | 1080 |
| tcgtcaaccc agagccccac cgcggctaat gcaagaggcc aaaaaatgtt tggaggaaga | 1140 |
| aaaacaaagg caggaagtgg cggcggcctg acggtgcgtg tgtgtctgca gagaagggag | 1200 |
| ggagccggct cagtctcttc ttgtttttcc aaacttcaag gtccaggcag ccctctgcag | 1260 |
| ggccgggccc cattgctccc cgcgcggcat tggaggtggc cgcccggaga ggagaaggcc | 1320 |
| aacgcctgcg ccaggcttgt caggcggaaa cggctaacaa ggagatttgg tcagcaaaac | 1380 |
| agacccagcc tttccgaggc ttcgtctgac ttggcccgaa aggttgggga ggggggcctt | 1440 |
| gcgcagagcc tcaggaccc tcctctctgg ggactaccat ccctgagcct tacgcttctt | 1500 |
| tccacagcct ttgcaggcgg aatatcggaa taaagtgggt ccaggcgcca aaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaa | 1628 |

<210> SEQ ID NO 37
<211> LENGTH: 3992
<212> TYPE: DNA
<213> ORGANISM: Artificial Sequence
<220> FEATURE:
<223> OTHER INFORMATION: Hox6as

<400> SEQUENCE: 37

| | | | | | |
|---|---|---|---|---|---|
| ttctctttta | agaagccaaa | gaaactttgc | tggttctttc | atcctttctt | tctctctatt | 60 |
| cctctttcta | ctctgtttcc | tccttctttc | tttcttttcc | tgcctccttt | ccctctccc | 120 |
| tccactgtct | tgggatatgt | cttacccgcg | caggagttca | tccgctgcat | ccaagggtaa | 180 |
| accgggctcg | tgtacttccg | gtcggcgcct | tcgtcatgga | gtgctttgcc | ctgcccgctg | 240 |
| ctgctgtcgg | aattccaccc | acgcacctat | tccccctccc | agcgcttcag | acacctctct | 300 |
| catcgaaaaa | ccgggcgaag | ggaagccggc | aacgagcgga | gaactctggc | tgaattaacg | 360 |
| gtggctccca | gaagctcctg | ccctctgac | agctgtcgct | tgggcagccc | gagagaagaa | 420 |
| ttgtcctctt | tcctggtgcc | agaggacgca | ggaaattagc | caggttgcga | gttgcaaagc | 480 |
| tgctgccgcg | gcgccgggaa | cggagcgcgc | ccaatctcca | gcgggagccg | ccaggcctgg | 540 |
| cctggccggg | gcttcccttc | gctcgccatc | tccggacaaa | gcacagccga | gcccggctgg | 600 |
| aaggcagagc | tccgaagcag | gcaggacgga | gcggagcaaa | agaatgcggc | tctattctcg | 660 |
| caagggaaat | tataaaaaag | ttcatgttca | cggttctcat | ccacatgacc | gacagcggcc | 720 |
| aatggaaggg | ccgaacaact | cataaagttg | tattgcaaag | ttgtaaattt | tcataaacaa | 780 |
| caacggattt | atgacccttt | ccccatcact | gagaggaggc | agctcttaca | ccggcgccat | 840 |
| cttaccaccg | aggccgcccc | gacttggggc | ctcaggtttt | acagacccttt | tgggccagg | 900 |
| ttttactaaa | agagccataa | gaagcgggcc | cagcccaggc | aggagactgg | agacgaggtc | 960 |
| ttgcaggcgg | aactcaggat | gctctgagct | gcccgcacaa | ccctggacc | ttcacccctc | 1020 |
| gccccttccc | cgcatccagc | tgccccagcc | cctgcccagg | ctgcgtagcc | tagcggggt | 1080 |
| ctgcggtcct | agcccctccc | cgcgccacct | actgcagtgc | cggaccctgg | ggcccctcg | 1140 |
| cctggtctgc | aggcggggtg | gggaccttaa | atcccatttc | ctagcctggg | gctgggttca | 1200 |
| gggcgcatgc | gaatccggaa | tcagctctgg | gtaatgcccc | tttccaagcc | cactgctcag | 1260 |
| ccttagagga | aagtgtggat | ttgaaatttc | ctcatggaat | tgatggaggt | ttttaggtag | 1320 |
| attcatagaa | tataacgtat | ctaccaaaga | ttccgttttc | aagggatcta | gaagatgtta | 1380 |
| gtgcacacgc | aaaaaccaga | caaacgtctc | tacacggata | aaggcacata | tacaattatg | 1440 |
| cacacaggga | agggcataca | ctctattgtg | ggcacagaat | gacatgcaat | tatggacaca | 1500 |
| caaaaacaca | tgcacccaat | tatggacacc | aaaatatata | caattgtgga | attaggtaaa | 1560 |
| aacacacaca | cagaaataca | tacacagaaa | aataagcaca | tactcataca | aatacacaca | 1620 |
| taaaaataca | ttaaaaagat | acatgacacc | aatacatggg | tacccaacac | ttggaccatc | 1680 |
| acaaggacag | ccaccccact | tttgcttccc | cactgccccc | tgccctccag | ccatactcac | 1740 |
| ctcccctttc | ccagtcccct | ctggataagg | cagtccacat | ttttctttgt | caccacgcat | 1800 |
| ctttatttc | ggttacataa | aacacagctg | ggctgggaag | tgtgccttcc | ctgaacccca | 1860 |
| ggatggagct | gagcagggta | caggacaaca | caggagatga | agggcattgc | ggagggcatt | 1920 |
| ggacctcccc | acccactaca | gttaactcaa | gacaacatac | catgctacaa | agtcacccca | 1980 |
| ttaacacatc | ctttccaagt | caagacactg | ccttacaaat | gaactccaag | actatagaaa | 2040 |
| tgataaaaaa | aaatcttgtt | caaatataca | gtatctgcta | ttataggaaa | catcagggcg | 2100 |

```
tacatattta acacagctga acagtaagat acaggagcca gaggaaagga cagcgaagct    2160
ggaagcatct ccacagtcct gctaagcaga agctaaccca cagatctgca gccagctcag    2220
gaacattccc ctccagaagt gggggttgat gggcctgagc tgtgggtgcc aagccagaga    2280
aggagggatt gattctaggg tgcaagcact taggatgctt tttggaataa atatattatt    2340
tttcgattta aatagatgcc aatacccctga tcctggacct cagcacattc tcagggcagc   2400
ctcagggacc ccaaaagctg cgggctgtaa gcagcagggg acttgcctgg gagcagtcgg    2460
cactaggtag caggcaagcc agccagcaca aataggtag ttttagggga gtaggtagta     2520
gtgagattca ctttcttgcg ggtctggag ggtggtgctg ggtgtctgcc agtgttggga      2580
tacataggga cttcctggga atggaggccc tctgggctg gatacatagg tagttttgggg    2640 gtgcctcgag cagaggcctg tgctaggtag tattttggac gcgccagagc agggccggct    2700
ggcctggggt tggggtgtc ttttgggtc ctcggaggca gagggaatcc aaggcgaccc      2760
agtctctgcg gccgctcagt ccacaaagt gggagctgg agtaggtgat gggggtgggt      2820
agagtgcagg ttggggactg ggttgctttt ttgtttttgt ttttgttttt tacattttct    2880 tttattttc ccattttgt aagtaaaacc agtgagtctc ttaaagacgc ttttccgact     2940
gtccggtgca gagagggccc cggatcggcc cctcattcct cctcgtcttc ctcttcttca    3000
tcatcgtcct cctcgtcggc cttgtccgcg gcagcagtgg cggcggcaga gggcacggcg    3060
ccctcgggag ctgcgcggc agtcggacct tcgtccttat gctctttctt ccacttcatg     3120
cggcggttct ggaaccagat cttaatctgg cgctcggtga ggcagagcgc gtgggcgatt    3180
tcaatgcggc ggcgccgcgt caggtagcgg ttgaagtgga actccttctc cagctccagc    3240
gtctggtagc gcgtgtaggt ctggcggccc cgcttcctgt caggtcctga aacagacat     3300 gcagacacat gaacacaagg acagacaagt agacagggca ctcgttaggc tgctgtccca    3360
gagcccgcac cttcctcctg gcctagtccc cagcgagcat cccctctgc cccaggcccc     3420 gaactgagct aggggaggag ggggagtgtt agggaaagac cccaactgca gtgccagacg    3480
cgcaggcagc tctgtaatga gcaaaggcac agaatctcaa ctttacaacc gacctttcca    3540
gccggctaag cttccacaat gtcctgcttc tctgacaaa ggaaaactgt aaatatagag     3600
tgtgagcaag tgggaaacgc tgcacttttg ccattcaaag atgagcccgg ccattcccct    3660
gccttgctag gcaagtgggc gactcttccc agcagcctga gccctcatcc ccaggacctt    3720
cctagggcac cccgaccctc tgtcctcatt ccctcgcccc catcttgaaa tggaccctgg    3780
cacagggtcg ggtgagaggc cctggagggc ttggctctcc tagcttttga gaaagaaatg    3840
tcaggcagca aggaaaatga ggagagagag aagaagaaag ggagggaggg tgacagagga    3900
gggagaaaga gagacagaat agcgaacaaa cttaatgtta aaattccaag acaaatggag    3960
ttaaataaat ttacgaggat cgaacccatt aa                                  3992
```

```
<210> SEQ ID NO 38
<211> LENGTH: 2881
<212> TYPE: DNA
<213> ORGANISM: Artificial Sequence
<220> FEATURE:
<223> OTHER INFORMATION: IGF2AS

<400> SEQUENCE: 38
tagaggcact ttaccgcccg gcgggagcgc ctctcctccg cgtccctcgc cccagccccc     60
tgcccgcccc actttgggac cctccagccg cttccccac aaatgagatc tttgcaatga    120
gcaaacgaaa gtggcgcgga tttcgggccg cccagcagga gcgagcgcag ccgccagccg    180
```

```
caagtccgca gccgtgtccc gcgccccacg ccggcctccc cggcggcagc cggagacgag    240
cgccagcacc ggcgggacag cagcagatgc gggccgagag ccggtcaggg gcgcagaggc    300 ggagggatc ggcgcggcgg ggagctcacc gcgaagctgg aggctgcgtc cgcgggcgca     360
ccaggagctc aggcagcgag cgatcgaacg ctctgtggca ggcggtggac gctgctgaag    420
ctctggctct gagctcaccg ctccgccgtc cgtgggacca agcccagcat tttacaaacc    480
cagctccttt ctccaagggt cctcagagcg cccctccgtc accccctgca gggcgccgca    540
gacgaggcgc tgaccttgcg ctcactcccc tcgctgggga aggacacact cgctggcgtc    600
agcccggccg gcctgggaag taggactaag gacccgaact gcaaccctcc acaccagaca    660
gcacagacca ccccaaggct gctcaatctg cccaaagcca aaagtacgtg ggggatatgg    720
gtccaggttg gggtgcttgg gagagggccc tgggagaggg gttcagacgg tgcacactcc    780
aaaggactga ggcggcgcca ctgtgttacc attttattga gtgtctaagg taaagacacc    840
tttgaaagaa cactcccggc ttctatctgg gatgggcaaa tcagcctgaa gagtcacctg    900
ctggatccct ccctgcaggc cctgtcgtgg ggcaggtaca gggactccaa tccatgtgcc    960
tccagctcca cgctccccca agtcctggag cctcccctgt caccccagtg cctgaccagt   1020
gaatgggtgc tgcccccact acagagctcc ctctggctga ggcagaggcc actggctggg   1080
cctttctagc cacctttcac ccctcttgca cacgggaagc cccgcaggct cctgaccaca   1140
atgggatcct gacgccggag cccccttaggc cctttgctca gaaggcctct ggttattacc   1200
tcaattctga acagccagga ggcctgagac tgtcacccac tttgataaat acagaccgac   1260
agaaaggtca ggccattggt gcaagacccc atggccagca gcctggggcg gggagaaccc   1320
gggggtctca cagcccccag cagagcccag ctttccttgg gttttttaggt tcttccccaa   1380 tgatattttc cctttttccc tctctaccca cttttctgccc cccatcttct cccctttggc   1440
tgcccgctct ctccctgccc ctctccccttt ctttgccctc tttcgtctcc caggagctcc   1500
cctgccagga cctcggtgcc gtggagactg cggggaacct gctctgccca cacctgctct   1560 ggccccctaga cggaagcacc tggagccaac cacggaactc cagatcccag ctgtgtgact   1620
gaatccacgc cagcctctct gagccaaagc tgcttgcaga agggggagat cccagttcga   1680
agactcccgc gcagagcctg tggccctctc tgccaggcct cagggtgcct gagacactca   1740
cctctctgcc tcgcagttgg ggctgaggct ggggctggct gccagcctca gttctgggag   1800
cgctggggtc gcctgggcca caggccacag cagctcacct caggactggg ctctctggcc   1860
tgctggggct caggctgtgg ggcaggctgg gcaggggct gagctggcag cgattcagag    1920 ccctgggggct gggggctgga atccacctcc tcccacacaa gctcggtggt gactcttcgg   1980
cccctgggga aaacaaaaa gatattgctg agatgacctc ttttaaagc aaagcccccc     2040 tccccataca ccccaagcct gagccctgtc ccatccccct ccccgggttc cttcaggtca   2100
ccttgtcagg atctgggcag cggcttcccc ctctagcccc tccccctgcct agagctccct   2160 cttttcaaagt ataagggagg gaagaagtgg tgagaagttt gcctagaaag ggcttcccgg   2220
tgctgatgga gaggccgaga cccttctgtt ggacaggctg ccctgttcct gggtgaggat   2280
gggcttctgc ctggcactgg gggtggaggg tgcacacgaa tggcccgcct tgagggtca    2340 tggcacggaa tatgaaagcc tcctccacct ccaaacaccc ccaccttgga aggagataag   2400
gagggggccc cagcaaaagc cactggacac acagctctgc ttgacgaggc cagtgaggga   2460
cggcgtggct gtgcttcctg gggaaatgaa cccccctcccc acagacacca ccctgggtgg   2520
```

```
atcgaggagt ctgggtccag ggtgcaacag agaaaaactt catgcatgaa tgagcattcc    2580
cagggaaact gccttggccc cagggcgcct ctctgtgcca gggaggctgg gagagcagca    2640 aggggggacca ggtgcgccat caggaggaga gaagctaaac ctaggggga catggagggc    2700
```

```
ggttgttgcc tctcccggca tttctcctca gtctcctgtc caatttcttg ctggtggtca    2760
ggaggcatag ggaggcagga gggaaggaag ctttacctgt aaaatggtgt atatatgtat    2820
aaataaaatc tctgcgccag aaaaaaaaaa aaaaaaaaa aaaaaaaaaa aaaaaaaaaa    2880
a                                                                    2881
```

<210> SEQ ID NO 39
<211> LENGTH: 432
<212> TYPE: DNA
<213> ORGANISM: Artificial Sequence
<220> FEATURE:
<223> OTHER INFORMATION: nC-uPARm

<400> SEQUENCE: 39

```
tcttttgaag gagaagaggt aaaaataat cagttcaaaa aattatacta aagaggccgg     60
gcgcggtggc tcacgcctgt aatcccagca cttcgggagg ccatggcggg cggatcatga   120
ggtcaggaga tcgagaccaa cctggctaac acggtgaaac cccgtctcta ctaaaaatac   180
agaaaaatta gccgggcgtg gtggcaggcg cctgtagtcc cagctactca ggaggctgag   240
gcagtagaat ggcgtaaacc caggaggcgg aggttgcagt gagccgagat cgcgccactg   300
cactccagcc tgggcgatac agcgagactc cgtctcaaaa aaaaaaaaaa aaaaaattat   360
gctaaagagt aaactcaaag aaagtagagg aaaagaatga attaaaaatc tgtgtttata   420
aataaaaata aa                                                       432
```

<210> SEQ ID NO 40
<211> LENGTH: 131
<212> TYPE: DNA
<213> ORGANISM: Artificial Sequence
<220> FEATURE:
<223> OTHER INFORMATION: NDM29

<400> SEQUENCE: 40

```
ctaactagac gctattgctt gttgaaggct ttgatcttag gaggattaga aagcattcta    60
ggccaggcac ggtggcttcc tgtgtgtaat cccagcagtt ggagaggctg aggcaggcgg   120
gttgcttgag c                                                        131
```

<210> SEQ ID NO 41
<211> LENGTH: 2248
<212> TYPE: DNA
<213> ORGANISM: Artificial Sequence
<220> FEATURE:
<223> OTHER INFORMATION: Nespas

<400> SEQUENCE: 41

```
aaagaggttg tgcttgctgg gttggttgga agcggttggc gggcgggcgt atggcggcca    60
ggcctagaag gccacggtcg ccgtgagtgc cttgggggcc aagcttttg atgccctaaa   120 tcgccaaggc aagtgggaa ggtcaggac ccccatggac catcccttgg gctcatgatg    180
gcggtaggct aactcactac acagagaggg ctatcgccga ggcaccgcgg agagaggctt   240 ttccaggggcc tggaggtggt gggccaggcc tatggagaaa gagagcttac tgctccgatg   300
cagacgagca gtacaagatg gacagatttc atttcccaga gatgctgaac cctgcacaag   360
gtgaaaggcg cacagtcccg gacctctccg gacaagtcgg atctgcctaa ccagctgcgc   420
```

```
gataccccga tgtgatccta gctgtctgcc aacccaggta gcccagaagg gcacccgtaa      480
agaaccctat accaccactg agtgtcctcc aagcactatc cactatcaag aaactccttt      540
ctgcgcggga aggttggctt taggacgcac gggagaggtg cgcgcgcccc ttttcacgat      600
ctcaggcctc ctcgaacctc cagaggtgct caccgagaag ccgactcacc ctctggctct      660
gcagagagtg gccccactgc gcaaggactg ttggggccga aaaggattaa ccttatgagg      720
agagaagctg gggtctgaag accccaatct cgcctcgggg caaaaagaag ggatgtacct      780
accttcaaac cactgcgaac tttctaaagc tccgcgcctc agcttgtggc tctcacgcta      840
catgagaaaa acaggtacgt cagcaagagc atcatggcta gggggcggcc agagaccact      900
ggatcctgct gttggactcg gaagaacaag gtaaaacgac ctgcttgttc cagagcgcgc      960
ttggaagagc cgatggactc agttaaaaca gttctgccaa catcatatgg agcacaaaga     1020
cattggtcta gccaatttta gggcacacag agagaggaaa acaggactgt gggtgctggt     1080
aaatgcccgt ttgatggaaa ctgatgccag ctgtcagcag tgaggtggat gatggttttt     1140
agtgtgtgtg ggaaagtgcc tcatttttca ggggaaagct ttatgcccgt gatagagatg     1200
gcagcccaca tcctatgcac tagtacgaaa acaccaggac tgcccacatt attaaaaact     1260
atgcattaca taatacatat cttggaccag ggttctgcat tagcactgct ctttcttgca     1320
agatgcgttt gaatcagcta tggacagtta acaaagcata cgcttccgag ccccggtcat     1380
ctgtacagtt acaaattcat ttcagcacgt gctcagcacg gactccagga ggagcagggc     1440
tgcaccaaaa gacagctcca tcttgcactt agtgccgagg ttgagcaaat ggatctgcac     1500
agaaaatgct ctttaaaatg cattatgtgc aggactttaa aaagtgcttg ctgcagagtg     1560
aatttcaaaa ggggccaagt aggtgatgaa cgacctcagt tgttaccagc tggggtacaa     1620
ggggttctct gtgtttgcag gtaaataaag tgtggtcata tattaccttt agactttcag     1680
gaaggaggct tctagaccag ttgggcagga aggcagtttc cagttgctta cagtatcata     1740
tagaagggtt cttatttgga tgtattggga agaagattct tttgagctta gaggactgtc     1800
ctgtggaaat ggcttcacta gttatttgac atagctccag ggggcaaaat gagggcctag     1860
atgggtgctg tgtacaggta ggcttcagcc caaggaggaa tattctagca agtaggactc     1920
tgaaggagaa tggactcggc gtcggcagga gctatgctaa gtcaaaggac agatgactac     1980
atgttagata gaggtttcca tggagcttgt gaaactgcta gagctaagac aaggtttgac     2040
cacggccctc tgtagttgct cccccagggc tgtaggagag ggcttggggt ggggtgggg     2100 gtttcaagcc tcccactctg cctcagtttc gttctcactc ctggagccaa ggtgtcagtc     2160
agggccatct attcattaca ttggcctctg ggcctcccct cctggagctg tcttggaaat     2220
tacaaaataa aattggctat ttagtggt                                        2248
```

<210> SEQ ID NO 42
<211> LENGTH: 17572
<212> TYPE: DNA
<213> ORGANISM: Artificial Sequence
<220> FEATURE:
<223> OTHER INFORMATION: NTT
<220> FEATURE:
<221> NAME/KEY: misc_feature
<222> LOCATION: (2412)..(2412)
<223> OTHER INFORMATION: n is a, c, g, or t
<220> FEATURE:
<221> NAME/KEY: misc_feature
<222> LOCATION: (5496)..(5496)
<223> OTHER INFORMATION: n is a, c, g, or t
<220> FEATURE:

```
<221> NAME/KEY: misc_feature
<222> LOCATION: (5559)..(5559)
<223> OTHER INFORMATION: n is a, c, g, or t
<220> FEATURE:
<221> NAME/KEY: misc_feature
<222> LOCATION: (6201)..(6201)
<223> OTHER INFORMATION: n is a, c, g, or t
<220> FEATURE:
<221> NAME/KEY: misc_feature
<222> LOCATION: (7513)..(7513)
<223> OTHER INFORMATION: n is a, c, g, or t
<220> FEATURE:
<221> NAME/KEY: misc_feature
<222> LOCATION: (8980)..(8980)
<223> OTHER INFORMATION: n is a, c, g, or t
<220> FEATURE:
<221> NAME/KEY: misc_feature
<222> LOCATION: (9011)..(9012)
<223> OTHER INFORMATION: n is a, c, g, or t
<220> FEATURE:
<221> NAME/KEY: misc_feature
<222> LOCATION: (17485)..(17485)
<223> OTHER INFORMATION: n is a, c, g, or t
<220> FEATURE:
<221> NAME/KEY: misc_feature
<222> LOCATION: (17525)..(17525)
<223> OTHER INFORMATION: n is a, c, g, or t

<400> SEQUENCE: 42
atcctgcagt tttctgaaac gtagaccctg tggcttagcc cagttaatct cgtaaactgg        60
gtcatcaccc tgggttgcac agcaagcagg agcctggcag cgaaggctgg ataaacactg       120
gcatcaacag gaaaaagcac tagaaagaaa ctggtttttt tcaagccctg agaacaatca       180
gattccctca ggtattgctt tcaaatctgt taccatcatc aggtaacttt acaaaacagg       240
gcaattaaag agctagttaa aggcgcctca gcaatttccc agacctccag ggaggtgaag       300
acaaggaaga ggaccacctc attgtcattg aaggsccac cacacctgtt cttgctattt        360
ggtgatgagc ttgtctagcc agtgaaccca ggcagsccat gactgttaag gaatgcatgc       420
ttcacaggag ttycaaaaac tcctcctgaa tttgtttatg gmcaagaaag agagcaagac       480
cccagctcct gtgcccatat tcacaccaat gtgcctgttg agtggcacat ataagsmtgc       540
ccttgggcta tgatascaaa gagargttat gcaacctcaa cccatcaayc ctgcccta         600 gaggccctgc aaggaaagta gaaaagctct tccttcacaa cacatgtctg actttttcc        660 gwascaaatg gcaggggagc accctagggt cctggagtta tttccttgta ggactcagaa       720
tgtgaattga tagagcttcc tagcactttg ttttgcctag aagtttagaa catttaggaa       780
acctctgatc cttcatttaa aaatattaac actttcactt taatcacttt aaacataatc       840
actttaaaat acaggtaatg cagaaaatgc atcccagtaa tttgaaaagg tttaatgtct       900
tccaaaacaa cgaaatagga acaaatacta tgatcagact ccatgggtcg ttaatcctca       960
catttgcttc tctgacctga cttggtggca tacattggca tccccatgtt acttatgaag      1020
aaatgaagca tgaagagatt aggtgaaatg ataaatatga cacgaggtga gcagagtagc      1080
tgggaagaaa gctcaagatc taggatctcc attgagaact caatgctctt ttgcacccrr      1140
aatctgtatc caacctcctt cctccatggt ccagcctctt gactcacaaa agcagctttc      1200
tttcttttca tatcactgaa ccaactgtcc atctcctcca cataatgtag gccatcttaa      1260
aaaaaaatgg attgatttga atgtaacagc atcatccttt ctcctctcaa cttgcccctc      1320
tttgtaccag aggatgtcat aatcaggtgt gaagaacatg aattctcaca tccaggaatt      1380 ttttcccccty aaattycttt gtcttatata atgtatagtt acaacaaaga ttgatgggaa      1440
tggaattaac caagttgtga actgtaaaag aaagaggaaa atgagtgaat gtagctcatc      1500
```

```
ttcggtctcc ttaagggcaa aggaaatatg tagtgagaac aagttattga tgaagacagt    1560
ccagtctgct accaaatggc ctctcaagga agacaggtgc agagatgtat tgtacaaagg    1620
gccattttta tattcagagt tgtgaatatg aggacaattc ttatttcaaa atatttgaaa    1680
tgaaggaaaa cattcagaga ataatttaag ggacacacca ttatagaaaa aattgatagc    1740
cccagtgtgc cctccaacat ttcatttctc aacatttctt ccccctaccc taaatttgat    1800
gcttcattat tcattgcatg ttttttgctt tttctataaa ttaatgtatc cataaataat    1860
atgtactatt ttcagatatt ttcaacttca taaaatatgg acaattgttt ttggcttaac    1920
attatacttt tatgttttaa acattatata tgtcttatat gattggcata ttatatattt    1980
tatattattt gaatattcca gatttttaat attatgtatt tcatatatac atattatata    2040
tatatgtttt acagtatatg tagctctaat tcattttaac tgttgtgtag tattccactt    2100
atgaataata cttatttgtc tgttttgtac caagacatta aagttgtata tgaaatttct    2160
ctacttataa atctagaaga caacttgcta tgtcataggg tatgaacatt tcatctttgc    2220
tggattttgc aaataatttt ctaaagcaat tgtatcattt tatattccat cccgcaatgt    2280
gtgagagtat ccatttctct acagtcttga aaacacttgt tattgccaga cttctaaatt    2340
ttgtgaaatt gatgagttga aaataaacct cattttatct ttaatttgct tgcttctgat    2400
cacagctacg gntaaaatatg ttttctatgt ttattgacca ttcagatttt tcctcgtcta    2460
tgaattgctt gctcatgtac tttatccatt tttctattag atttgttatg ttctcactga    2520
tttgaaagat ttatgtatac attcaagtac taacgctttg tcaatatact catcatacaa    2580
ctgtggyctg ttcttaaata actgattgta tctctgcagg aatttgcctt gcacaaaagt    2640
tttaacaagc aagttaaaac taagatatag ataagaaagt tgatatttcc gtaagtctgt    2700
gagttcagga aaagcattag gaatgccagt ttttcattat ttatctactt gttttttcctt    2760 ccaagttcag agagataaag tataggccac ctagctttat gtttgatagt atctgtgctt    2820
tgcagagtgg gtagtgtaga ataatatggg agatgaataa ggaccaattt tgagaataat    2880
tagccgcaga ttattgggcc taatagattg catatcttcc actgaaatag aaactgtttc    2940
aaaccaaatg catctctagt cgtgacttca catgggagca catagaatct gctctatgca    3000
ggggcataag gcatgcagaa acaatctatt ccaacttatc cctcaaatat tttactacca    3060
ggcaagtctc tgctcatgac ataagtccct agactcaggt aaccaatgaa acaaaagta    3120 gaataatgtt atggtaatgt caggtcacat ggatatattg tcttgggaat cttgatatga    3180
aatcttaaaa taaccttggc tatctttcta tttcagaggt gtggcgaaat cttgtttgag    3240
aaccccgatc agaatgccaa atgtgtttgc atgctgggta agaaggcttc tcattttaaa    3300
tatattaagc atgttgatgt catgtggagt tatcattctg ttgccttttt ggctgtctct    3360
cattctgttt tgaagaggct gataggttct tttgtggtta tgcagacagc tataacacat    3420
ttatatgtgt aacacttgat gatgagaaaa ggttctgatt ttcttaattg tcagccagtc    3480
aaggaccatg cttctgagtc tttcawaaat tttcttggat catcagcata acatagaatt    3540
aggtggtttg tattcaggca gctatgatga aaaggtaaga accatgttgt aattcctaaa    3600
ccaaagatgg atgataagat agacaagtaa attattaagt ccttacatca cagtacaaaa    3660
cccttactta gaatttctgg aagaaatgta tatttgaact actgtaatct gaagtcagca    3720
caactattat cgacacagca tttgtaacaa ataacaacaa ttgtaatgaa taatcatttg    3780
ttcttgtagg atgatatatc atcaatgcct ttgacaaact ctttaatat atactgttag    3840
```

```
gtaatgaagt tggtattatt ttcctcattt tataggttag aaacaattat agagaatata    3900
agtgatgcac ttaacctcaa agtgagaaat ggtccaaatc atgatatgaa agtttctaaa    3960
cagtaaaatt ttaggtctag tgtttagatc ttatttaagc cactaaacta tgtccaataa    4020
agttgcaatt cattatagta atagaagtaa acagtagcat ggataaataa aaataatttc    4080
taaattttat tttcaccaaa tttttacctt tgtagattct aaccttgaac tatattaata    4140
agcaaagaaa aaaattattc attttagcat tttctattta ctctgcccac ttcatatatt    4200
gacagtctag attattggtg aaaagcagac agcaagttaa atagaggcag gcaaagatct    4260
tggtaattta taattcaaaa taatcatgta acaaataatc aaaggtggta cacgacttaa    4320
gaaacaaaca aaaaccagac atcatatttt tctagccttc taatctttct taaattcttt    4380
actgattttt aaatctctct ttgcagttct atgtttttat tttaattaag atggtggcta    4440
tatagtaata cattcattga aaaatgaacg ttttactaga agcacatgaa cgaagaatat    4500
agcattgcat ccatacaccc atttcaaata tccaatattc cttccccttg aaagtgtgaa    4560
atgaaaatgt ctccaaagtt ctaatatttc aggtactaga tagatagata gatagataga    4620
tagatagata gatagataga yagayagaca gacagacaga cagacagaca gacagacaaa    4680
acaggtacag atggaagcag aaaaaaaatc ctttgttaag ccatgtgtcc cagttttgga    4740
tttgggaaac tgttttacca tcacatcaaa taatctattc aacaattaac tcatttaatt    4800
ttccacaata acaagatgag gttggtgcta ttgttatctt cattttataa ataaggaaat    4860
tgagggaaat ggttgaatac tgcaggtacc ttactaccac tgaaatatta tttgattgta    4920
gctttcacct ggtctagtaa cttgaatcaa tgtttaactc atgataattt taagcacatg    4980
aatgcatcat ctattttgac tgaatgtttc tgtgtcctgt cttccatgta agttgattga    5040
ttagtttata gctagaacag taagagactt tctactactg cctatagatt tgaattcact    5100
taaagtaaga tcaattatct ttccatctct tctagattat gtggtatggt ttatatagct    5160
gccagaaaac aatcctgacc gccaaatatg tctctaatga atctgccaga ttgcacaaaa    5220
ttctaaaatt agaaatgcat ttatataaat cagttttatg ttgctaccac tgtcataata    5280
attacagtta attgagcact taatatgtgg caggtgaaat ccatcccaaa caccttacat    5340
aattagatca tttattctaa gtaaattaag agaagctcta tcttccaaaa tatagatatc    5400
tctagcaata gaagagtttt aattaagctg atactggtta ttaaccttgt agatttcatt    5460
agtttgttag atttcccttt ttttcgtaat tcaganctaa ataataaaag gacctgtgag    5520
aatggaagtt tttattagtt tcaggacaca taggaatanc aagtatacat tttacccttta    5580 agatagacag taaataatta atgactattc aaagataata ttatgcttag tgagtttgag    5640
ttgctcacat agtgaaaatt gtgcccttga ggagcttata tttaagacrg cttagatttt    5700
ttaagagaat tgctgcaact tttaattcag acacttatga agtcctttga aatcttagat    5760
ggaagaatac caaaataaaa tcattatgga tatcaataca catggatcaa ccccaccatt    5820
aacatgcatc cacctgaagc ccaaggactg ccacttcaca scaaaatgat cctagatgat    5880
aaaagaaaga agtaaagttt aatggtttat tcacttaaaa taaacaagag aaatcaaatt    5940
atgagcacgt aagtccctaa aactgagacc acatcttgta tttcttcaag aaagaatatc    6000
tatattaaca caaaaagcac ctcttcacca ctgtctaagg tattaattag tttgttgcta    6060
tcttcaaaag gaatctcaga taatgttctt atgatttcct aaagcatttt ttgagaaaac    6120
tttacatctc acacaagaaa gtataaggag tctctgatat tgtaaggac tattgtgttt    6180 tataagccct gccaaccata natgtagttt ttattttgt aggtaatttt ataacatttt    6240
```

```
tatgaataaa tcaaaatttc taaatgagaa aaccaaatat atggggccac ctcaatattc    6300
agatccctga tggggaccaa cctgagacat cctcatcttt aactggtcaa gcccttggct    6360
cactcccctg gaaacctccc tctctaccca ctcacactcc aggtttgggt gcctgctgga    6420
tcctagctgt gtactggttt cagcacagtt ggggtggaat ctggagaagg gtcactagcc    6480
agggactcca tttgcatttc cttctcttcc attggcgagt ccccatatca ttctgaaaag    6540
tactgttttt atgctttgtg ttgtctacct cacracttcc atgaatatgc cattcttatg    6600
gaaaattaca cttctgactc attccgttaa atgagacata agtgtaaaat tcacctcgag    6660
ttactctggt gcrccggatt caatgcagct ttaaatggaa ccaaactact gtcatgtatg    6720
agtcttgcag ggaattattt ctggcttcaa gagaatagct catgttggat atgaaggtaa    6780
atacaggtgt actgcagagc tgactacacg gagtgttaac tatttattcc ttacaattgt    6840
tcagagagag caaatgtgga tgatcaagtt aaacaccaaa ttgtaatata tgttgctttc    6900 tttttttcctt caggcttagg gaatgtgtg tagagcttct gcctccctgt cctcccctct    6960
ccaccttcct ttttataaat ttagccataa gatttcactc aagttcaaat tggcctcaga    7020
agtttatata attatatcaa tggatataca actgtatagc aacactttta ccttcttcag    7080
gtctcatgaa cagatactaa aagaaagagg aagtggaaga gacattatct ctcactgtat    7140
aattaatgca tgaagtatgg caagttacaa aacagagttt acttttcaaa agcataatga    7200
aaactgttgg gcaaaaagag cccagaatat ttaaagaaat tatgtaaaat gatcaatgtt    7260
gattcacttc tcagttcatt tgtgaacctt gctctgtgaa acgataaatc atgggaaaag    7320
aaactttcaa gaagaaattg ctgatcagat ttagtgcttc tttgtatctc ctattttctc    7380
tattattaga atgggatttt tcaaattat aagccttaat ttttaattta tgatatttg    7440 ttggctcaat ttctccatcc tctttatcaa ggtttaattt tttaatttg aaattttcat    7500 tggccctgtt ttngtctcat gtatgatttc tttcatgctg atgagtatca tgactattag    7560
aatgtacaat aagcactttc ttacctgcca taacttagaa gggagtattc atattagtca    7620
gtktttctgg ttgaaaatta ttataaatga tttaaatgat tgctaatctt cagaacaaca    7680
gaacaccaga aaatcaatat tttattaaca ctcaacatag gcatagaggg acttgctttg    7740
tagcactagc tctgaaaaaa ttaactgtgt actcacagaa gttgcttcat ctctctagga    7800
ttcaattcat agttttcctg caaagtggaa ataaaaacat ctgtccttcc tagcccaggg    7860 gttttctgg tgagagaatg agatgttcta tgaggagaag cctgttatga tgtctgccct    7920
aaatattatg tatgcatcaa taagttgatg cataaatgat aaataattga aaatgtaaaa    7980
attgataata agcaaatata aataagctaa taaaaattat tactgatgat accaatggtg    8040
tttagaaaag caatcgaaaa gctaaaacat atgaatataa ggacaatttt ttaaatatta    8100
aatacattct tcaaaattgc atggtgcctc cagggtagaa cgagaccttc atctaatttt    8160
aattaatcgg atgtgcatca agcacctaca aggtcgtgtg cttagcattg agaatccaaa    8220
gaccagtggg gcatagagtc tgcccttaga gggtttattg ttcagcaaga gattgaggtc    8280
ctgaagccca atgtatgcaa caccaactcg actgataaag gctacagaag aaataaagat    8340
aaactacact ggacttcmaa acatggatag agtgcatata gcagggatgt gaagactcat    8400
ctatctagat atgaaagttg agaacgtggc agcactctag atggatgcaa gaccactctc    8460
aaaagctcag agataaactg gggagtgttt ctggggcagt gtttcaggcc acgaggtaga    8520
tgaaagaata aattgaaaag aaacttgaga cctgattaca gagagcttta ctgtcatcat    8580
```

```
tggccctaaa aaggacagaa gtaccagata aaagagagtt ctggtctctt ttatttagtt    8640
agagagtctt ttcgatttag ttatagcata tcagagaata ctctataagc tcctaggtac    8700
tgggtagtat taagtacagc cattcatcag ctacttgtga aattaaataa ttttaaacca    8760
atgcatattt aacccaatgc gtatctgacg acctgaattc tggtttgatt tttttttaaaa   8820
acatgttaat tctattttc ctcttcatat caaatattat agtattttat taagcaacaa     8880
gataatattt tcatctgtga cagtagagaa aaatgttttt ttcactttt tggaactttg    8940
tcagctaata aagttgggag ttattttata tctatatttn gctcttatca cttgcttcag    9000
cttttggttt nngcatgtgg acacttatga gacctatata ctgtttctta aaaaaataat    9060
acacaatctg ttttaaggca aaataagatt tggtatcaaa gtaggccact gtggtgttgg    9120
tagaaagaac agggcattga aagacctggt accagctaat aactgtgtga gcagaggcat    9180
gtcatttagg ggttgtagac ctgtttactc ttctctaaaa ctgaataata agcaataata    9240
acaatattat tgtctacctt attagggctg ttgaggatta cgtgacaata aatattaaaa    9300
cattcagtga acttttagaa gtactataaa tataagttat tattttatt aatactcaat    9360
tttttctaag tccttgcact tcattttata ttagtagtat tttatagca aactgacagt    9420
attgtagatt ttaaatatta aatgatctca atttggttca agtgaataga tattttcaag   9480
tgcatgttgg caatttagta atgaacatcc ttataggtta tgaaagaaat attattgtaa    9540
agattatttt gcgtgcactt gacttaacaa gtaaagactg tgttgaaaga cagacgtttt    9600
caagttgctc gattttgatt tattaaggtt agaatgcctc aggaatttga attaattta     9660
acttacactt tcaaagctct tcattgctgt cacttggatt catcaattca ctctctctat    9720
atgcgtgctc agacaacaaa attgctgaat gatattttct tactctgccc aaagagggta    9780
aattgaacct ggatattctc aagggaggat ggtggaagca tcattcccca tcactcaccc    9840
aaggccctgt cttgtttcac ttttcattgc acttatcact aaaggacata ttttctattt    9900
gtccatcgct gttccccagc cttgccctgc aacacaccca tacacrcaga atgtgattat    9960
cacagaagta aggactccgt ttcattcact gttgagtatc cagcatctgg aacatctagc    10020
tgcccagccc ctaagaggaa ctcactattt gctgaatgga tacgtgctga tgtgttttgtg  10080
agaacagcag tcatccggag tgcatctctc gagtgtgtca agatcggtt ggcctagtat    10140
ttaaaactct ctgctaacat agccaaggcc aagggtcagc tcctacatta actaactggt   10200
ggcttcccaa gcacactact ccaggttaca agataagaaa aagtggttcc cttcaaatag    10260
gcaatgagga actatcctaa gaggaagatt aacatgcatt cattgagcac tgctgtatgc    10320
ccaaccctct gctaggagta ctctgaaagt tgatataata atgagcaagg tagaatccct    10380
attgccacag agtatattct tgggcagatg gagcattgtg ctgagaatac aggaagaggc    10440
ccattatttt gtcttctgtt tatgggaata tacagaaaat ttttttcacct tgagggttat   10500
ggtttaaaag gcattccaca ttatcctact gccttttaaa attttggaag tcaatattgc    10560
tttgtgtaag aaaaacaagt ttcctagctt gaaggttgct ttctgtggaa ggttgcagca    10620
tttccacagc aacagaacac ctcattttg aatgcagctg gaagccaggg ctcagatgag    10680
agctacctgc agaataacaa cacaagcgaa gtccaaacta tcagaactga agttgtcaag   10740
cccaaaagtg atagaagtgt cagtcttgta ttgagttagc ttcattttct gtctaaagct    10800
agaaaaaggg aattcaatga gacctatcag ccttacacaa agctacactt cagaaaacat    10860
gttcaatcaa caaacacttc atagatacac attgtgtgcc agagtaggga tgcaaagata    10920
ttgaaattct atcctcagca agctcccaat ctagtgacac agggacgacc acacaaacaa    10980
```

```
tgacaacata gcatgataaa ccacaatcag gagagcccag gtcttacggg aaggggaagg   11040
ggaagggtgg agtggcatca ggaaagacct tgtgcaagac atggtaagga gctgagtgtc   11100
aaagagaagc tccagacagc cctggagctt gcactgagga cagcccattg ggaaaggtgt   11160
tgttggtatt tctaagagca acaggtaccg gcagcttaat gtgaccaatt aaaaactgta   11220
agaaagtctt tatgcctgga aaatagagta agaggaatga gataagacaa tcgaatgtgg   11280
acaggaaggc aggagagatt atgaagagcc ttataatagg acaaataacc attgaaagat   11340
gtttaagcag aggagctaca aggggagata cacactttag acagatcatc tgtttagagt   11400
ggagaatgca caggaggagg atatcgctga agaaagacta gtttagggaa cagtggtatc   11460
tatcaggtga gaaggatga gtcctacctg aattgagaca gtgtcagaga gaacagaagg   11520
tgcaaaatac aggaaacttt tcaagagggt gatagaactc tacaatgggt tgagtgtatg   11580
aagtgttatt aaacagatcg agatactgcc ctgtcccgca aagaagagtc caagagaatt   11640
gaatttgcat ggggtgggga gaagttaaat tttagacaca gtaaatctga gatgcccaag   11700
gaactttcca ctgcagcaca gctcagaagg agggctctgc aagtcagtgg cggtggcgac   11760
ataacagaaa tgagatcacc cagggaaagg tgaggagtga gatgaggttg tgctttggaa   11820
tgcccagaag catccccaaa agggttgggc aggttcaaaa ggagcctatg gaagcctaac   11880
taggtaggag actaaaatag agtgggcaga aagataaagg aaaaggagag gattgtacct   11940
tagccatctt agcctaacta ggtaggagac taaaatagag tgggcagaaa gataaaggaa   12000
aaggagagaa tggtatctta gccaccttag ccaagaggag agagtttcaa aaggtggggc   12060
ataatacaaa tgtaaaatac tgtagaggtc aaatgagata aagcctaaaa agtgttgctt   12120
ggacttagca acctgaaggt aacaacagca agagcatcag cagcagaagg tggggtgagg   12180
tgggtagtgt ggagccaggc cacagggagc tgagggcact cctctgtcaa gaaattggtc   12240
tgagagggct gagtgcagtg gctcatgcct gtaatctcag cactttggga ggccaaggca   12300
ggcagatcac ttgagcccaa gaattcaaaa ccagcctggg aaacatagca agactccatc   12360
tctacaaaaa atacaaaact agccttgag gtgatggcag gtgcctacag tctcagctac   12420
tcaggaggct gaggtgggaa gatccattga gcccaggagg tcaaggctgc agtgaaccat   12480
gatggcacca ctgcacactc cagtctgggt gacagagcaa gaccctctca aaaagaaaa   12540 gaaaagaaag acagaaagag caagagagaa aggaaagaaa gagaaaggaa gaaagaaaga   12600
aagaagaaaa gaaagaaagc aaagaaataa agacggaagg aaggaaggaa aggaaggaag   12660
gaacgaaaag aaaagtcaga aaggctggtg gaggatatga cagtacctct caaagtctgc   12720
cgtcaggaag ggtttcttag gataggaagg atttgagaat gttttgatgg tgagaggaaa   12780
gaggagaaga actggctgaa gttttatgaa gagaaatgga gtagttgtga gccttaaacc   12840
tgcgattgtg agaagatggt ccccgtgggc gaggaagcat ggagatagag acaggtgtgc   12900
ctgggtccgg ccaggcagag ctggaagagt ttccatctga ttgcttccct tctttttaag   12960
aaggaaatat ggtgttctga tgagcttaag gagaggagca ggtgaatgca agcatacaga   13020
actaggttaa ttcaaaacta atgttacaag aaatataaaa aaactgaata gaggtgttta   13080
aaaaaatgtg gagcagtttt gaggacccag ctgagttgga cactgtaaat atccaggcct   13140 attcttttaaa attaaaaaat acagaaaaga caaactatgt gttcttaaca ctcatttcaa   13200
aagagtaact gtcccatgct cataaagacc cttcccttta ttctccttaa ctgcttcccg   13260
gtcctttccc tatggccagc caaggtaatc tgcaagggga tgccttgaac ccaattcaca   13320
```

```
aatccctctc cctggtattg tacatgtgaa gttgcttctc cacttcccca gtgagcctgc    13380
acattccggg taataggtct ctgatttaat tttctagcac cctgtgttgg cctagaattc    13440
caagaaaaca caaaaaataa ttcctgatga aggtagacaa aatgtctaag gttatatatt    13500 caccctaac attctcccac cacccatggt gactctagaa ggttattttt tgacctgtct     13560
tggcctaaaa ggggatgcct ctacatccac ctcccacttt gtgaaggaga ccaaaggtgc    13620
taagccattt gagctctggg agtacaaatg tcccctgagc tgggcccacc cctgtccaat    13680
cacatcaaaa ctgcctcttc cagccagaac agtggttcac gcctataatc ccagcacttt    13740
gggaggccga ggtgggcgga taccctgagc tcaggagttc aagaccagcc tggccaacat    13800
ggcaaaaccc catctctact aaaatacaaa aaactagcca ggtgtggtgg cacgtgcctg    13860
taatcccagc tactcaggag gttgagacac gaaaatcact tgagcccagg agacagaggt    13920
tgcagtgagc ctagatcgcg ccactgcact ccagcctggg tgacagagca agactctgtc    13980
tcaataagag ttaagaaaac tgcctcttcc tcatcctctc taattctggt tcattttccg    14040
cttctataaa ttggattcaa aacttcttgc tttcaagatg agtccatcta ggaatctttg    14100
tatacatcaa actgtacttt ttaaaatgtt ccagagacaa tgtcattttt aattttgacc    14160
ccaaaacaat gttaggcttt ctattggaag gagtatagat tatagttata tttcattgta    14220
aattcatatt ttttaaacaa attattaata taggtttatg agatctcaac ctgccaatct    14280
caaaccacct cataaatata tgaggttttc taatattcat aaattataaa tattcacaaa    14340
atatagaaat tttcagaatg agacaaatta cgtgtattac aaaggatgca caagaacaaa    14400
tgttgaagta ttaaataaat aaatacttgt tctcattata tcaattgcta tctttgaact    14460
gtagcatttc tttttcatat ctaattgcca aaatatattt tgttttctta ccaggagatc    14520
cattctaaag aagtagctag ctgatggtat agaaagctca gttttcataa acccaacatt    14580
ttcccctctc actgaataat gcatgttttt gtgactctag catgaacgct atcaagctta    14640
ctgattattt cttactataa aaaccttaaa ggcaaatcta aggatattta caaatgaaaa    14700
ccaaatgtgt agaatttttt tgcctacttc aaggtaccca accacatagg agcctaattt    14760
gatttgtagt caacattttt tacattttct gacttgtaat ttaaggagat agttaacatg    14820
aaatcttgta cattgccatt ttagctttac ctaaattctg ggattctggg agctctagtt    14880
ctttgtgaca caatagaaaa attgaagaca tcattctaaa caaggacctg acattctgaa    14940
atataagaaa atagtgccag aaatgctaat aggatataga attccatgaa gttggtgaat    15000
agcaccatcc tcattttttc aatgataatc atatactaca aatctgagag tttgggaata    15060
tgaatagtaa atataagaaa agagttacta tgtcaagctg ctttctaaaa tttatgtcga    15120
aatgtaaatt tcagaaaaag gcattttaat attttctctt cttttagaaa atcaagtatt    15180 taaaaagaa attgaacatc ttggaagtat atattgaact caaaaataca ttttccttgt     15240
ttctgaggaa aaaaattagc atcatattcc tgaattactg cattgtttat agaatgggtt    15300
tgttaataat taattacacc aggcagtcta cggaaaggta ccttattttg tctgctattt    15360
cactctttgt gtcaggaaaa atcttccctc atgaatcatg tttacaagat ggttgactaa    15420
tgaaatgcca agaggactct gggtaacagt atatgaatga ctatgatcat gttttgtata    15480
atttaacaga catttggaat atcacagagt cttttcttaa aaaaaaaaag tttacatttt    15540
tggaggcaga gtctcagttt gttacccagg ctgaagtgca gtggtgtgat cagagctcgc    15600
tgcctcctgg aattcctggg cttaagcaat ccttccacct gaccctctca gtacctggg     15660 actacaggtg tgcaccacca cccctggcta atttttaaat tttttgtaca gatggggttt    15720
```

```
caccatcttg cccaggttgg tctttaactc ctgggctcaa gtgattctct caccttgacc    15780
ttcataacag agtcttaagc aaatctctga atatctgaag gggcttagtt ctttcaaata    15840
ttgctttcat gggactttaa ggttgcagtt caagtaagag gtagatgata acttcttctc    15900
ccagactggt ctacttccta ggattctaga attttgacgg acaggtctcc aacatgtgac    15960
catacaaatt tgtgtaaatt tctaggacat aacaataaat aaaggatttt ttcccttgta    16020
gcaactgtac cattgaaaat ggagaagtgt ttgactaata acaaaacatg tgactgccat    16080
gtttattttg tttactttcc tatggaaaag tttcttagaa gatcagtttc aaatgttagc    16140
atctttaaga gagaaaattt tcaattactg tatttaacat tagtaagtat gaaccaacaa    16200
tgtgcataca catgtgtaag cttatattta ccagtagcct gatgtgcctc aacaattgaa    16260
atggtagttt atatacttac tggcacctct aattctcctg ctattcattt atttagctat    16320
tggtttattt tgatttaaag tggggttttt aacttttta ttgaaataca gcttaaattc    16380
tgagaaatgt ctagttttta agtgcagctc aatgaatttt tacaaagtta acgtatctgt    16440
acaaaaccac atggatgaaa acagatagtt tccctcgtac cgcctcctag acattacctc    16500
ccaaagattc cattctgatg cactgaattc tatcaccatt ccctaatttt gaaatttata    16560
tagatgaaat taaagagtat attctttgtc cagtctgcct tctttcactc aacactgtct    16620
atgagattca tgcatgctgt tgcatataga gtgtagttcat tcttatttgt ttcttttgct    16680
atagaacaga agtcagcaag tcacagctct tgggctaaac ctgacctgtc acctgtttga    16740
ttagaacaca gccatgtcca ttcatttaca tattgcctat ggcagttttc atgctacaaa    16800
atggtagagt ttggtcatga tagagaccat ctgatcccca atacctaaca tatttgctat    16860
gtgtcccttc acagaaagag attgccgatt accactatag tgtctaaata ttcttataca    16920
tgtctttttg tgcaaaaaat tacacacatt cttttcaagta tctacctata attgcaaatt    16980
gcaattgttg ggtcatagag tgtatatgtg tgtgtgtgtg tgtgtgtgtg tatgtgtgtg    17040
tgtgtgtgtg tgtgtgtgtg tgtgtagttc agctttattc tgccaaaaag ttttccaaac    17100
tggctatacc aatttatcct cctaccagct gtgtacaaaa gtcccacaaa taatttaaca    17160
ctcaatgatt aacttaagta aaagttagaa tgcataattc atcatttgac tcaataaaaa    17220
cagtttatgt aatagcctgt aatgaagatc atgattatca tttaagtaaa caaatcatca    17280
ggtgttacca tcaggttgat gatggtagta ataaaatgag taaattttat ttgctgatta    17340
tccatgagca ttaaagagtt gatgaagttt gttgcataaa ctgaattaat agttattctt    17400
tgttgaacac ttgaaaataa atgtcccaca aatgatccta gtaagtgctt actcacccac    17460
agggaactat aaacaaaacc ctggntcata aataaaaact gttttctgtc gacctaatta    17520
atttncattt tttctttctc aacaaaatat acaactaact atattttaca ga            17572
```

<210> SEQ ID NO 43
<211> LENGTH: 2346
<212> TYPE: DNA
<213> ORGANISM: Artificial Sequence
<220> FEATURE:
<223> OTHER INFORMATION: SNHG3

<400> SEQUENCE: 43

```
gattctctaa ctgcgcatgc ttctgcgcac gcgcaataga cattccagga cttccgggca      60
cttcgtaagg tttaaaaagg atgcttcgcg ttttctctct ccttttttgga gacagattcg     120 cagtggtcgc ttcttctcct tgacggagtc ggtttgtcac tcaggctgga ctgcagtgct     180
```

```
cgttgcaacc tccgcctgcc gggttcaagc gattctcgtg cctcagcctc tccagcagct      240
gggattacag gatttgttaa ggattccaag taactcttat ttggagagaa gacgatctgc      300
acttcgcatt ttggcattga catttaattt tagggtcctt tatatagaag ggagagtagg      360
taaactgatt ttttttttta acagggaggg tttgacaatc tttggcagac ttggagcaaa      420
agattgaggt gcatttcatg cctccttttg agagtcttgc tctgtcgccc aggctgtagt      480
gcagtggcgc aatcttggct gcaacctcag cctcccaagt agctgggatt acaaacataa      540
gccaccacgc ccagccctca tacctctttt aaaagtcgac ctgttttgca gaaagtctgc      600 tgttttgta ctaaaggctt tggaatttgg catttagcta ggaatgcaca ttctttcacc       660
tcattcatac tttaagaacc acagaagtga ctctgcttgg ccagaaggca cactgtgttg      720
gtggttatat taaagtcct tgagtatttt gcttttcatg atcttgctca ctgcaacttc       780
cgcctcccag gttcaggcga ttctcctgcc tcagcctccc aagtagctgc gactacaggc     840
gtgtagcacc acacctggct aattttttgta tttttagtag agatgaggtt tcaccatatt    900
ggccaggctg ttctcaactc ctgacctcgt gatccgccca cctcagcctc ctaaagtgct     960
gggattacag ctgtgagcca ccctgcccgg ccacttttgt atgattcta atgtatttgt      1020 aatttaccta acaaattgcc taatctgcta tgttaatgta tttatgaatt aaaataaata    1080
cgactgcatg tttgtggttc attttgtgg aggtggctgt ggtgacatca gccaagaatc    1140
tgaatggtac tgttgaagga aactagcatg atagcttcag ttctaaaggc cctgaaacct     1200
agtctcaggt gggtcccct tgggttcact ttatattggc agtttattgg gaaaatggat     1260
attaggtcct gaccaatagg accgtaagtc tgggttgagt gcaagatgag ttagaccgat    1320
tctttagctt cctgcagtgt agtggaggaa aaatcgatgg tagcaacggg aggttgtatc    1380
cctagctgat gagttgtatg agcctctact acctggcgca cctccgcctg aagattgcca    1440
gaattgcttg cctcatgacg tgagtcacaa tggaaacttt gtcaagcccc ctgcactggc    1500
tgccaacata aatgttcagt accctgaagg atgggactga aggggatca tctagaaggt    1560 aaagttacct actggcatag gggaggtggg acagccgtta agccatttgg aacttgatgg   1620
agacaggttt gagggaggtg ggtgagattg gagtttggtg gactgtagag cttgcttgcc    1680
aaggtgttga ggtcagggtt ggtttgagaa tggaagctag ttactagcta tgattgtggg    1740
ggaacacagc ttgattttc ttacaagcta agaggagtga ggcagtgttt aagagggcat     1800
gttaaatgca gccaggcttg gtggctcaca cccgtaatcc cagcacttag gctaaggcag    1860
gcggatcaca acatctagag atcctggcca acgcggtgaa accctgtctg tactaaaaat    1920
acaaaataac tgggcatggt ggtgtgcacc tgtgggaggc tgaggcagaa ttgctggaac   1980
ccgggagatg gaggttgtac tgagctgaga ccttgccact gcgctccagc ctggtgacag    2040
agttaagtct caaaaaaaag gcatcttcct aaagcaattg tatttgtgct tacctgtgcc    2100
aggcactgtt ctaggtaagc actaagtggg ctttaataca gcatattcca atggggaatc   2160
ccaggaacca aaagactaat tgtccaagtc acaactaga agtggcacct ctgcagaaac    2220
aagcatcaaa ttccctgctc aggaagaagc cagatgagtc agcccattc gtctgtatgc    2280 ccagtcccat ccgtgtcctg ctgtaactac atagatctca cctgagtaaa gtgattttt    2340 tctgaa                                                               2346
```

<210> SEQ ID NO 44
<211> LENGTH: 1100
<212> TYPE: DNA
<213> ORGANISM: Artificial Sequence

<220> FEATURE:
<223> OTHER INFORMATION: SNHG4

<400> SEQUENCE: 44

| | | | | | |
|---|---|---|---|---|---|
| gcagcaacgg | aaaggcgcca | cgctcgtgag | cggaaccagc | gttccggggg | cgctcagtgt | 60 |
| gggcaggcag | gaagcctggc | tccactagga | cacacagatt | ctctcctgag | cagctgcgaa | 120 |
| ctatgcgccc | cttctaccct | aagagatgg | gatgggagtc | caacaaaccc | agccattgct | 180 |
| cagacccag | cccttctctc | ctctaagaag | caggttcacc | tctgccaccg | cactcgcatt | 240 |
| tttttttttt | tttaaagccc | ggcctttcct | aggcgggtc | aagggccccg | cccaccgaag | 300 |
| ccacgcccag | tagccgcccc | ggggcggggt | tccctcggc | tcccggctgc | ctttccct | 360 |
| ccggcctctg | ccggtgctgc | tgcgccctgc | ggagctccga | acacgtgcgc | agaggctggc | 420 |
| tgtggcagat | gcaactgcag | gatgacttga | agtagggca | tccttcaccc | atctgaaggg | 480 |
| aggaaatagt | ggcaggtgac | agtctgcatg | tgcagttttc | agatgccttc | acctgaatga | 540 |
| catctacctc | catcaggacc | ccagatgtct | gacagccctg | tgtgacacca | agataagtaa | 600 |
| cgtatgtagt | cttcttgtca | tgtaggtccc | aattaaatta | ctatagctca | gatggggta | 660 |
| ggggacttaa | aattatgatg | tgaaaaatta | tgtagagtat | cagacttttt | tttggggggg | 720 |
| gacggagtct | tgctcagttg | cccaggctag | agtacagtgg | ctcgatctcg | gctcactgca | 780 |
| acctctgcct | cctgggttca | agcgattctc | ctgcctcagc | ctcccgagta | gctgggacta | 840 |
| caggcacctg | ccaccatgcc | aggctaattt | ttttattta | agtagagacg | aggtttcacc | 900 |
| atattggcca | ggctggtctg | aaactcctga | ccttgcgatt | tgcctgcctt | ggcctcccaa | 960 |
| aatgctggga | ttacaggttt | ttttgtttgt | ttttgagac | ggagtctcac | tgtctcccag | 1020 |
| gctggagtgc | aatggcgcaa | tctcggctca | ctacaacctc | tacctcctgg | gttcaagcga | 1080 |
| ttctcctgcc | tcggcctcct | | | | | 1100 |

<210> SEQ ID NO 45
<211> LENGTH: 37027
<212> TYPE: DNA
<213> ORGANISM: Artificial Sequence
<220> FEATURE:
<223> OTHER INFORMATION: Tsix

<400> SEQUENCE: 45

| | | | | | |
|---|---|---|---|---|---|
| taaaaatgta | aaagatcagc | tgggtgtggt | ggctcacacc | tgtaatccca | gcactttggg | 60 |
| aggctgaggt | gggtggatca | cgagatcagg | aattcaagac | cagcgtggcc | aacatggtga | 120 |
| aaccctgtct | ctactaaaaa | tacaaaaatt | agctgagcat | gatggtgcac | actgtaatcc | 180 |
| cagctactca | gcaggctgtg | gcaggagaat | cacttgaacc | caggaggtag | aggttgcagt | 240 |
| gagccgagat | cgcgccagtg | cactccatcc | tgggcaacag | aacaagactc | caactcgaaa | 300 |
| aaaaatcaa | taaaaatgta | aaagatcatt | cttagcttgg | aggctataaa | aaaggatgca | 360 |
| gcatgtcaga | tttggcccat | tagctgcagt | ttcctgacct | ctatctacct | caattggttc | 420 |
| tttacttaca | ttacatggaa | agtgcaaact | tggatggctt | caatgtctgg | cttcttttat | 480 |
| ttatttattt | atttatttat | ttatttattt | atttattttt | tgagacgggg | tctcgctgtg | 540 |
| gcccgggctg | gagtgcagtg | gcacgatctc | tgctcactgc | aagctccacc | tcctgggttc | 600 |
| acaccattct | cctgcctcag | cctcccgaat | agctggaact | acaggtgcac | gccaccacgc | 660 |
| ttggctaatt | tttatattt | ttagtagaga | cggggtttca | ctgtgttagt | tagccaggat | 720 |
| ggtctcgatc | tcctgacctc | atgatccgcc | catctcggcc | tcccaaagtg | ctgggattac | 780 |

```
aggtgtgagc caccgtgccc ggctggctgg cttcttttta cccttcacat ctggctttaa    840
atactacctt ttcacagatt tcttctctaa tcactctttc taaagtaaat atgctgtttt    900
tcattattag tcattgcatc ctatttcttt ccctttaatt ttcttatcac aatgtataat    960
tatatgtttt ttttttttt tggttattgc ctgtctccct caatagatca taagttccat   1020
ttgataaggt acaatgtctg ttggtttatt agccagtgcc taacactacc atttaatatg   1080
tattcaatga atatttgtta aatgtattga ttgaatttaa agtgactact cagcctactt   1140
ctgccccttg gagcttggat tgtttcttca aaggtattga tccttttgac tattttaatt   1200
atgaattcac taaagacatc tggaaggctt attgtgtcaa gcagtgccaa atccatggct   1260
tgatgaacct agatccatcc ccttcccctt tccatatcac agatgacaac ttgatggttg   1320
gcctatgact tgtaaaagtt gtcatatttg aattctgaaa tttctctaat tttcttggga   1380
agcagaaagg aaaaattagt agttggcctc aaagggacag ttgaatttca catataatga   1440
gcaaagtagt gtgaggaaga gaggagggcc ttttctttg aggtcataac taaaagttag   1500
gtgagcaaat gccataagca tgaaaatagc aaaccaagct tcttggtttc tatccaaagg   1560
ctttgttggg aaaagtatca aagtgtgttc atttgttatg taatatataa ggtagagaac   1620
ccaatttgaa ggaggtggaa taactttcca aaatacttat ggctaaattc tcagttgatc   1680
ttggaataag attcaagaat ccaaatgcac ccttctttgt tatcttgcta gaaacatgc    1740
tgggcatggt ggctcatgcc tgtaatccca acacgttgag aggccgaggt gggcagatca   1800
cgagatcagg agttggagac cagcctgatc aacatggtga agccccgtct ctactaaaaa   1860
tacaaaaatt agccagacat agtggcacgc acctataatc cgtgctactc aggaggtagg   1920
caggagaatt gctggaaccc gggaggtgga gtttgcagtg agccaagatc acaccactgc   1980
aatccagcct gggtgacaga gcgagactct gtctcaaaaa aaaagaaaa gaaaaagaa    2040
aagaaagaaa aagggaagg gaaggaaagg ggggagggga gggaagggaa gggaagggaa    2100
ggtaagggaa gggaagggaa gggaagggaa aagggaaaac aatgtgcttt tacccacagc   2160
tgataagctt ttctaattgt ctacctttgg gttaaacttt atcattgagt gttttatcc    2220
cattatgaaa gaattaaggt ttgaaggact gaggtaaggg tggatattta ctcttaattg   2280
agtagcttaa ccaagtcaag ccacagatta gctgaagcca aaaagcactg gcagcatttg   2340
aaataactga gaacatatta tacttaacac tttattatct aagagaggca cttgaagttg   2400
agacctagaa atttgattct gggttctttg tttctaaggg gcagggtgaa cccagctata   2460
gcattcacag atgctataga attatatata ttctatatat aattatatat attacattca   2520
tattaatata tgttaatata ttctatatta ttcatataga attcacagat aatccaagtg   2580
cttttttaat acattgatac caaatctctc ctgctctcaa aaaaaaagc ccaaggcaaa    2640
aatttttgat tagcctgtat ccgcaaattc atagtgcatg gcatgatggg tactctacat   2700
ccctcctcct attgcactca ctgtgcccag atgaacctaa agtcaccagt aatagtgcta   2760
atgtagtaat gggcccaagc ttcaaaagaa ggaaaattag tattcagtat ttaaatgtgg   2820
gaaagaggaa gaatatggaa attatcaatt ttataatacc tatacatatt cttacctgca   2880
ttaatgtgaa tagacatcaa tgataaacag aataatgccc cataaagatg tctcacactgt  2940
aatctccaaa acttataact atactatatc acatggcaag agggaattaa ggttactaat   3000
cagctgacct tgagatggga gattctcctg gtttgtatgg gtgggcccaa tgtaatcaca   3060
gggtccttat aaatgaaaaa ggcagacagg agattcagtg tcagactgat acaatgaggg   3120
aaagactacc agcagttgat ggctttgaag atagaagaag ggggccatga gccaagaaat   3180
```

```
gtgagtagcc tctagaagct gaaaaaggca agaaaacgga ttcttcccta gaatctccag    3240
aaatgcagcc ctgccaacat ggtgatttta actcaatgag atgcatttta gacttctgac    3300
atctagaatt gtgttatttt cagccctcaa gtttgtggta atttgttaca gcagcattaa    3360
gaaaatgtac aatgaccatg tgcagtgcct catgcttgta atcccagcac tttgggaggc    3420
caaggtgggt ggatcgcttg agtccaagag ttcgagacca gcctgggaaa catggtgaaa    3480
ccttgtctct acaaaaacac aaaaattagc ctggtgtggt tgtgtggacc tgtagtccca    3540
gctactctgg aggctgaggt gggaggatgg cttaaaccca taaggtggag attacaatga    3600
gccaagatca tgccactgca ctccagcctg gacagtagag ccagaacttc tctcaaaaaa    3660
ataaaaaaga aagaaactat acaatgctcc tgtgattcta gtgctatgta catatatcct    3720
ttatagggaa ttaaggaggt tatagacaca accagaagag gaggcatgga atagactaat    3780
gtataatgga taggaaagtg tatcttttac aacttctctg taaaaacacc ttcacctact    3840
ttatgagttt gcctcagctg ccataacaaa atatcagacc aagtggctta ataacaatt    3900 tattttctca cagttctgga ggctagaagt ctaagatgaa agtgccagca agtttgattt    3960
ctggtgaagt ctctcttcct tgcttgccaa tggccgcttt ctcactgtgt cttcaaatgt    4020
ccttcctctg agtatgtgag gagagagagg tttgatgcct cttcaccttc ttataaggac    4080
accagtccta ctggattagg gctccaccct tatgacctca tttaacctta attacctcct    4140
taaaggttct atctccaaat acagtcacat ttggagtcag acctacaaca tatgaatttt    4200
gagaggacac aattcagtct ataacaccta gatggaaggc aatttcatat aaagatgata    4260
tgcagtctat gacagcaaag tagctagtgg aaatcacaac ccctaattct attttatgt    4320 cattccctaa gtccaggtcc catgtggata tagcattgtt cagggctatc tctttgctgt    4380
tctttttttt ttttttagact cacacaagca atgtggagaa ggaacatgaa aacatctttg    4440
agatagagct taatacagat gtcaatctct ttgtaaataa gcaattaaaa gtggaaccac    4500
tgtccaccat gtgagaagag tgactggcta tggctggata tttttaaata cacataaaat    4560
gtggtataaa tggtagaatg ccagggatag aaggagtatc ttataagtta cctagtcaac    4620
gttctggctt ctgggcagaa aactatctaa actcagccag ataatcagtt tcaactaaat    4680
caggaaaaca tggaatcatc tttatctagg tagtgttata gttacattgc ctcatttatc    4740
tacacatcaa taaattcttt ctcattgcta atatttatca ttcttatcat agtataagca    4800
aatgttttaa ttctattatg gtaaagataa agcttctgta attaaaacac tttaatctgg    4860
aaagacagca gtaaacccct caagcaaaag cccaagtagg ttcaaaaata atagccagag    4920
aggttaaagg taaccaata gagtgatatg ttacagcaac taagggagag aggcaggagt    4980
tttttaaaag agagaagagg aattataaca acagaaacag gttagccagc tgccagttta    5040
gatgagcata atgagtccct tagatagatc attggtgatt tttatcaaaa cactatcggt    5100
ggagttgtgg gagtggtagg ctgactatag tggattgggg aattaaatag tgatgaaccc    5160
aaaacagaaa gtctgaagaa attcccttg agccaaaaaa aaaaaaggcc gggtgcagtg    5220
gctcacaccc ataatcccag cactttggga ggccgaggtg ggaggatcac ctgaggtcag    5280
gagttcaaga caagcctggc caacatgtg actctactaa acattgtctc tactaaaaga    5340
tacaaaaatt agccggaagt ggtggcaggc aacttaatcc cagctacttg ggaggcagag    5400
gcaggagaat tgtttgaacc cgggaggtgg aggttgcact gagctgagat cgagccattg    5460
cactcaaacc tggggacaa gagggagact tctctaaaaa aaaaaaattc cctttgagca    5520
```

```
tctctactgt agagatgaaa taagagagaa gtggattctt tagtatagag atggaaaggt    5580
atggagctag aacatgtggg ttgtgaacag tggctaacta aaccaggacc agtaacctag    5640
atatcacatt gggcttaatt gctgggttat tcattcattc aggcaacatg tatttgttga    5700
gagcctgaat gtgccaggta atagaaacac aaaggtggtt aaaatagacc ttggcctctg    5760
tcttcaggaa gcttccagtc tgaagaggga tgaagacata tattaatcaa acaatcccac    5820
aaatgcaggt ataatctgca taaactgaca aatatatcta ctttggagtc aagaaattaa    5880
gagaaatcac tgatgtgatc agtgaacaag taagatttat taggaagatg aaggatgac     5940
attacttcaa atatattaca ggaaacccca accatggtaa caacatcagg cctatcttta    6000
catatgttta ataatgctta acttcacttt tgctcctatc ctccccaaag caatcttcaa    6060
gttcttctgt atctttgttt tattttcttt gttctttttt gtctcatttc ctatactgtt    6120
tttattccat actttgacag ttcagtgaac tcctttgata gatcccaagt cctcctttt     6180
caatatttac acttataatc attttgatc actccaaaac tgagaacttt gagtgtagat      6240
tttctaggct tcttatttta ttttagaca ttatatagaa aaattagagg gaagggaaaa      6300
gaaggatggc aacatggtaa ctgggacagt gttcaaaagg tctaagtcct acttctcact    6360
ccatacaaat tatctgcaat tttttatt ttgagacagg ctcttatctc tcacctgggc       6420
tagagtgcag tggcacaatc atagctcact ataaccttga actccagggc tcaagggatc    6480
cttccatttc ggcctcccga gtagttagga ctacaggtgt gtgccactac acacagctag    6540
ttttaatt ttttttattt tcatagacac agggtctcac tatgttgctc aaactggtct      6600
tgaactcctg gccccaagca atcctcctgc cttggcctcc caaagttcta gaattgttac    6660
aggaaagagg tcccaatcca ggcccaaaga gattttattt atgtactagt gtggagccta    6720
gcctaggaca catcaagcag aagtgcagat aaggtctgac tctttccagt acagctaggg    6780
tgcctggctc tccacatgtc cccagacctt atctagaatc taatgtctcc aaggtaggta    6840
cattgaataa ttttcaaaag tcaaggaagc agttatgac cttaaagtag ttagcaaact      6900
taatatctga cctgactaat ttagaccaaa tgtttacatt tttgaagata ttttattt       6960
atcagtaatc tttaaaacta ttttctattt tccaaagatt acttaagtca aatgaactaa    7020
aaggcattat acatttagt tttctgatga atatctgat ttaagcactt attattttg         7080
aaccaattaa agctttttta tatcacacac acaacacata taaatacaca gacaggctgg    7140
gtgcagtggc tcacacttgt aatcccagca ctttgggtgg ccaaggcagg cggatcacgt    7200
gaggtcagga gtttgagagc agcctggtca atgtggtaaa accccatctc cactaaaaat    7260
acaaaaatta gctgggcatg gtggaggatg cctgtaatcc cagctactca ggaggctgag    7320
gcaggaggat agcttgaacc caggaggtag aggttgcagt gagccaagat tgtgccactg    7380
cactccaggc tgggtgacag agggagaccc tgtctcaaaa aattaataaa taaatacaca    7440
gaagaagata aaggacttat cccctaaggc aggaatcaaa ccctgaacac aggccaccat    7500
tgtgaaaaga aaaagcacag ccacatggtt acaaggtcaa gctcccaagg acatacaaaa    7560
caagaaggaa acctcatcca gttttttcag ggacctgcag caaagtttgt acctgataaa    7620
tttactgggc catcttgaac agcaggttta caggtgtcct aagctcatgt tctatcctaa    7680
gataccctc tttatgacag aacaatacag aaagacacac aacagatttg ctacaactta     7740
agactagcct cataaatcca ttttttcact aatcaaaact ttacagagga aatgaacagt    7800
gattttgcc atccattcaa ccagttttat agagagagag agaggaaagc attgcctgag     7860
gcagggtggg gaaggcccgg cactccgagt gccagagaaa gccccaccca ttgcagcaac    7920
```

```
actgaaaagt tcatgcagct gcttgtcagt catgaacgga ttttttccag cagtcccatc   7980
agctctcatt tccctttta ggagggaaaa gctccccatg ttctacaatc ctctacatgc   8040
ctaattctgt caaccatagc catcagcaaa gagtgcaagg cagatcaatc caaagagaat   8100
agcggttaac atcctataat gccaaacctg ttcttagccg aaaggacttt aaggagagg    8160
gactttactg agagggacct ctaaccccct aaatcttaaa agggactcta atcctcctaa   8220
gttgggcctc taacccagtg tcagtcaagc atccttgcct tttattgaga ggaagcttta   8280
accctctctt acgagagact ctaactcccc taagttgagc tataaccaat cccatccttt   8340
gcctgagtac cccaccactt acccaaagtt gtccaattag taatgctgca gtctatttcc   8400
tttgtgctgg gggtctcctc agtatcatcc cttcgagttt caccagaaag atgttatcag   8460
gccccaccac ttacccaaag ttagcctttg gattgggggt ttctgcatta tagtcacttc   8520
agtggttgcc aaaagatgt tataggaccc ccaacactta cccaaaatta acctttgggt   8580
caggtatttc tgcactatag tcccttctgt gataatcaga aagatgttat aggaaaagga   8640
tcctgatcca ggcccccagg agagggttct tggatcttgt gcaagaaaga attcagggcg   8700
agtccgcagt gcaaagcaaa accaagttta ttaggaaagt aaaggagtaa cagaatggct   8760
actccataga cagagtaacc ccaagggctg ctggttgccc attttttgtgt tttttttcttg  8820
atgatatact aaacaagggg tggattgttc atgccttccc attttagacc atataggta    8880
acttcctgac attgccatgg catttgtaaa ctgtcatggt gctgatggga atgtagcagt   8940
gaggatggcc acactaatgt gttttaagcc ttttcctcag ccaaactaca aaaagcaaa    9000
aattactttg tttcaatatt acccctactg gctaacacac tagcaggtca tcagaatatt   9060
tgccattcct acaaaattcc aagattctgt gatgatcctt tgagtataag aatcacagag   9120
atacacacaa ttgttacatg ctctatttaa gttttctatg ttatattttc tctttatacc   9180
ccccaccccca tttcctgact cttctttttt aaagggtctt tgggatcatg aaagcaaaat  9240
gcagcatcct cagtgtcaca cacgtccatg tgaagagacc accaaacagg ctttgtgtga   9300
gcaataaagc ttttttaataa cctgggtgcg ggcaggctga gtctgaaaag agagtcagca  9360
aagggagata ggggtggggc agttttatag gatttgggta ggtagtggaa aattactgtc   9420
aaagggggtt gttctctggc gggcaggggt ggaggacaca aggtgctcag tgggggagct   9480
tctgagccag gagaatgaat ttcacaaatg tcatcagcta aggcaggaac cagccatttt   9540
cacttatttt gtgattcttc agttgcttca ggccatctgg atgtatacat gcaggcttgg   9600
gctcagaggc ctgacattcc tgtcttttta tattaataag aaaaataaaa caaaatagtg   9660
ttgaagtgtt ggggcggtga aaatttttt gggggtggt atggagagtt actgggtgat    9720
gtttcttagg gttgctttga gtgggattag gggtggcgtg ggaacctaga gtgggagaga   9780
taaagctgaa ggaagatttt gtggtaaggg gtgatattgt ggatttgtta gaaggaatat   9840
ttgtcacata gaatgattgg tgatggcctg gatacagttt tgtatgaatt gagaaactaa   9900
acagaagaca caaggtccca ataacagaag gagaaaaaca ggtattaaag gactaagaat   9960
tgggaggact caggacatcc aatcagagtg cctaagggg ttcagcgtga ttattttctt   10020
ggttgatgag ttttttgggct ctatccttga gtttttttat gttgtcatat accaagccag  10080
attgatttag gtaaaaacaa cactttcat ttaaaaatac acacagtccc cttttttttga   10140
gcagtaagtc aaggcctcag tgattttgga ggaaagagaa atgcaaagcc agcaatcatt   10200
ttttaaagaa ggattagaaa cagctaggag agagtgaatg agattgatag tgtggtggag   10260
```

```
atagctgggg agaggtagag ggtcgcataa gaacaggaat gagaataaga gtgaatataa      10320
aggtaaagaa taggacttta ttagggtgaa agtattggag tgtaccttgt cactgaagat      10380
cttctatcca cttcaagaga gacttaagga aggtggtttg aggtaaaacc aggagatatg      10440
agttatgatg gtttggagga aaagtgtaaa ctggcagtgt aaacaagggc agggcattta      10500
cgagtagttg agaatggtga ataggagtat gactagacag aagatagtag ggatgacaag      10560 ttttgggggtt gcagtccaag tagtggggt gactgcataa agccttgttg caataagtag       10620
ggtaataaac ttaatagaat gaaaggatgt tttaggctca taagggttac tactgttctt      10680
cagaaatgtg agtgagttta agggaagtag ggttgagtac ttgcaacttc taggaggaag      10740
aggagagatt aggctggctg tccaatggac acagctttat tctggaatgg tgagcctaat      10800
agggagggtc ttacaggcgg atggcagttg gggtattata gatgactaag tagggtccgg      10860
tctatcaagg ttatagagtt tgaggggtca gattcttaac aagaactgat cgtccatcta      10920
gggtgtcttt atatggctgg gaatatggag taggcaagaa aagattagca gcttggcaaa      10980
tttcctgtct tgcctgctgg aggaccagca gatagattcc tagaggactg gtgtctgaga      11040
cgaggttggg gccaagcaag aaagtgtgtc tatataaaag tttaaatgga ctgtaccctc      11100
tagcatctca aggacaggct ctaattctga gaaaggcaag aggtaaaagt actgtccaat      11160 ctttttttaag ttggaggctg agcttggtga gatgtgtctt taaaagacca ttagtccatt      11220
ctacctctcc tgaagattga gaatggtaag gggtatgaag gttccactga ataccaagag      11280
cctgagaaac tgcttgggtg atttgactaa taaaggccgg tccattatca gactgtatag      11340
aggtgggaag gccaagccta ggaattatgt ctgaaagaag ggaagaaatg actatggtgg      11400
ccttctcaga ccctgtggga aagtcctcta cccatccaat gaaagtgtct acccagacca      11460 agaggtatttt tagtttcctg actcggggca tgtgagtaaa gtcaatttgc cagtcctggg      11520
cagggcaaat tctcgagctt gatgtgtagg aagggaggg ggcctgagga attcctgagt      11580
agtagtagta tagcagatgg gacagagaag tgatttttt aggatagatt tttacaaagg      11640
aaaggaaatg agaggtttta agaggcagga tagcagcttg caacttacat ggaaggggtt      11700
acaaaatgac aacagaatag aataggcctg tgaggctgga aggagatatt ttccttgttc      11760
caagaaccat ttgccttgtg tggaaagaga ttgataggtg gaagtttcag tgggagagta      11820
ggtgggagtg acagatgaga aggagaaaaa ctggccatga gggacagaag ttgggacact      11880
agctgcttct ttagctacct tatcagcata agcactgtcc tgagtgatgg gatctgatgc      11940
cttttgatgg cccttggagt gaatgactcc agcttccttt ggaagtaaag tggccttgag      12000
aagagttttt attaaagagg cattaatgat ggaggacact tgcatagcga ggaaacctct      12060
tttagcctac ataacagcat ggtggtgcag gatatggaag gcatatttag agtcagtata      12120
aatattgatg tgtagtccct ttgcaagagt gagagcctga gttaaggcaa tgagtttggc      12180
ttgctgacag gtagtggagg tggacagagt ggtaacatca aggatagatg tggaagatac      12240
tatagcatag cctgcctttg ctaatgagtg acaattaggc ctgatggaac tgccatcaat      12300
aaaccaagtg tgatcagggt gaggaacagg aaagaatgaa atatgggtaa atggagtgaa      12360
tgtcaggtag atcagaaaga tacagtcatg ggggtcaggt gtggtatcag gaataatgtg      12420
ggagccagcc taaaacagta agatcaagtt gcttggacag aaaggctaca ggtcatggtc      12480
ctggctcttg tgtaagaatt ctgaccgcac agccctgcac ttcagctgtg tgtaatgaaa      12540
aagggttcag atgagttagg gagagctagt gtggagcag cttccagggc tgttttaaga      12600
aatggaaaaa ggagtgggga aaggatttag gatctatggg gtcagctagg ttttcttttg      12660
```

```
tgagtttata taatggttta gtcaggacag taaagctagg tatttaaagg caaaagtact   12720
gaaccatgct caggaaagaa aggagttgtt gctttgtcaa gggggttggg gtttgggaga   12780
ttagccagac acgatcagca gggagagcat gtgtgttttt atgaagaatt atgtcaagat   12840
atataacgga tgaggaagaa atttgggctt tggaggcaga tgtgcaatgt ccttttgaga   12900
atagattgtt ggagcagcag gagggtgtcc tgttgggaag atttgtagga ggggctataa   12960
agtagaaggt catcaaaata tttaataagg tgagatgtag atggatggaa agagagtaaa   13020
tcatgagaaa gggcctgact gaagtaatag gagctgtccc tgaagccttg cagcagtaca   13080
gcccaggtaa gttgctgaga ctgatgggtg tcagggtcag tccaggtaaa agtaaagagg   13140
gccttggagg aagggtgcaa aggaatagta aagaaagcat atttgagatc cagaacataa   13200
taatgggttg tggaggggtt gtgaagggag gtattaagaa taagagagta tatgggtttg   13260
gcaccatggg gtggataggc aaacaatttg gttgataagg tgcagatcct gaactaacct   13320
gtaagacttg tccggttttt ggacaggtaa aatgggagaa ttgtaaggag agtttatagg   13380
cttcagaagc tcatgctgca gcaggcgagt gataacaggc tttaaccttt ttaaagcatg   13440
ttgtgggatg ggatattggc attgagcggg gtaagggtga ttgtgtttta atgggatgct   13500
aaggggtgca tgatcggtcc ccaaggaggg agtaaaggtg tcctatactt gtggattaag   13560
gtggggagat acaaggggag gatgcgaagg aggctttgaa ctggggaaaa ggcggcaatg   13620
aggtgtggct gtagtccagg aatagccagg gaagtagata atttggttaa aatgtcttgg   13680
cctaataaga gaactgggca ggtgggaata actgaaaaag agtgcataaa agaatgttgt   13740
ccaagttggc accagagtgg gagagtttta aggggttttg aagcttggcc gtcaataccc   13800
acaaccgtta tggggcaagg gaaacaggc ccttgaaagg aaggtaatgt ggagtgggta   13860
gcctccatat tgattaagaa ggggatggac ttaccttcca ctgtaagagt tacctaaagt   13920
gtctgtgatg gtccaggagg cttctgaggt gatcaggcag cgtcagtctc cagctgctaa   13980
gccaagcaga tctgggaaag tgtcagtcag agagccttgg accagagctt tagggctgt    14040 aggagtagct gccaggtgag ttggacaatc ctatttccag tggggtcctg catagatggg   14100
acatggctta cgaggaatcc caggctgcag cattccttgg cccagtggcc agatttccag   14160
cgtgtgaagc aagatcctgg gggaggaggt ctggaaggaa tgcctgactg ctgtggctta   14220
ggtgctatga agttcttgtg tgctggagat gtggctgggg tttctctcac agtggaggca   14280
agtaattgca actcttctct attattgtac accttgcagg tgaggttgat taattcctgt   14340 tgtgggttt gagggctgga gtctaatttt tggagctttt tctaatgtca ggagctgact   14400
gggtgataaa atgcatattg agaatgagac ggccttctga cccttctggg tctagctagg   14460
gtggtaaagt gtctaagggt tgttgccaaa tgggccatga actgggctgg gttttatat    14520 atgatgaaaa agagcctaaa cactaactga tttgggagag gtcagctaaa gaaaaggag    14580 cattaaccttt gactatgcct tcagcttcag ccacctctgt aagaggaaac tgttgggtag   14640 atggggagg gctagccaca gaacgcaact gtaagctgga ccaggtgtga ggaggggagg    14700
tgatagaagg attatagggt gggagagcag aggctgagga aaattggga cctggctcag    14760 cctggtgagg agcagcctgg ggaggagggg agaggtcaga tgggtctgta gaaaaggagg   14820
attcaaagga ctcagagctt ggggtggaga ctgaaggaag agacaggaga gaaagaagaa   14880
agatttggga tgagtcacat tgggagcaga gattaggaaa agacttgttg caggaagtca   14940 gggacccccaa atgagggac cggctgaagc catggcagaa gaatgtggat tgtgaagatt   15000
```

-continued

```
ttatggacat ttattagttc cccaaattaa tacttttgta atttcttatg cctgtcttta    15060
ttgcaatctc taaacataaa ttgtaaagat ttcatggaca cttatcactt ccccaatcaa    15120
taccettgtg atttcctatg cctgtcttta atttaatctc aatcttgtca gttgaggagg    15180
atgtatattg tctcaggacc ctgtaataat tgcattaact acacaaattg tacagcatgt    15240
gtgtttgagc aatatgaaat gtgggcaccc tgaaaaatga acaggataac agcaattgtt    15300
cagggaataa gacagataac cttaaactct gactgccggt gagctgggca gaacagagcc    15360
atacttctct tctttcaaaa gcaaatggga gaaatatcgc tgaattcttt ttctcagcat    15420
gggatatccc tgagaaagag aatgcgcacc taggggtagg tctctgaact ggcccccctg    15480
gggcgtacct gtctcttatg gttgagactg cagggtgaa ataaactcca gtctcccata     15540
gcgctcccag gcttattaga aaaggaaat tcccacctaa taaattttgg tcagaccggt     15600
tgatctcaaa accctgtctc ctgataagat attatcaatg acagtggtgc cctaaacttc    15660
gttagcaatt ttaatttcac cttggtcctg tggtcctgtg atctcaccct gcctccactt    15720
gccttgtgat attctattac cctgttaagt acttgatgtc tgtcacccac acctattcgc    15780
acactccctc cccttctgaa aatccctaat aaaaacttgc tggttttgt ggcttgtggg     15840
gcatcacaga tcctaccgat gtgtgatgtc tcccccagat gcccagcttt aaaatttatc    15900
tcttttgtac tctgtccttt tatttctcaa gccagtcaat gcttagggaa atagaaaaga    15960
acctacgtga ttatcagggc aggtcccccg atagggactg atgtgcaaaa gaattcctgg    16020
atatcaggca cctcagacca tttgcccatt ttacgacaag aattatctag atcttgtagg    16080
atggagaaat cgaaagtgct gttttctggc tatttggaac cattgtcaag tttgtattgg    16140
ggtcaagtgg tattgcagaa gaaaataaga tgtttaggtt ttaggtcagg tgtgagttga    16200
agaggtttta agttattgag aacacagtct aagggtgaaa atggaggaat ggagggtgga    16260
agtttgccta tagtgaagga ggcaagccct gagaaaagag agggtagaga cacggagaga    16320
aggggtgggg ggtacttgcc tcccggggag gtggtgcttg ccaccaaggt gaaggatcaa    16380
ggcaggcatc cccatggtga tcagacacct ctgaaatgtg ggtgaataat caggcaggca    16440
tcccegcagt gattaaacac tgagggaaga ctgtcttccc gagaccatga ccatcgtcag    16500
agttttgggt tcacacataa aacatgtctc ctctgtctct accagaaaag gaaaggcact    16560
gaaattaagg gaagggagag attgaagggt agcacagaaa ttgaaaggag aaagaggttg    16620
agggatagtg aaagaagttg gagaagagag caaaaagagg ctgcttacca gatttaaaat    16680
tggtgagatg ttccttgggc tggttggtct gaggaccaga ggtcataggt ggatctttct    16740
cacggagcaa agaacaggag gacagsggat tgatctccca agggaagtcc cctgatctga    16800
gttatgcac caaatgtcac gtgcatccgt gggaagagac caccaaacag gctttgtgtg     16860
agcaataaag ctttttaatc acctgggtgc aggcgggctg agtctgaaaa gaaagtcagc    16920
aaagggagat agggatgggg cagttttata ggatttgggt aggtagtgga aaattacaat    16980
caaagggagt tgttctctgg caggcagggg tagtggtcac aaggtgctca gtgggggagc    17040
ttctgagcca ggagaaggaa tttcacaagg taatgtcatc agttaaggca ggaatcggcc    17100
attttcactt cttttgtgat tcttcagttg cttcaggcca tctggatgta tatgtgcagg    17160
cttgggctca gaggcctgac actcagcagc tactaccacc attggcacca ctggcaccac    17220
tgccaccacc ccactgcacc ccagttgctt cactctccat cacagaagcc ttttcagcaa    17280
cagccaacat ttgtaccctc accaagccct ctgattttcc caatcacaag gccttcacta    17340
caatattttc ttcattcaca agtgtcacct attctccatc cccaaggtaa gtcaattcta    17400
```

```
attttcttgc aagggttgac agaggtaaaa cctgtccaga taccccaaag gtgtttcatc   17460
ttggcaattc ttgactcttt caaggaaata agaatagtca aatataacta agtaaaataa   17520
ataagaatat ataaggtctg taaaccaaaa atgaaattct aagcccccca accaactgaa   17580 tggaccccte ctctcagcca agggcattct aaagttaacc tgaaagacta attcaggcca   17640
tgatggaagt gggtggtcag gcatgcctca ttatatcctc ctcccttttgg aatttagaca   17700 caaatgacca acattaacat taaaacagag accttaagat tgacaaagta gactctttgt   17760
agcaataaga tatgaacaca acagatagca ggccccaaaa tatatttatt caacatattt   17820
ttaaatggcc ctgcaaagct gtctcttgtg gggaaaccta cattctgtag agaatgccct   17880 tcccttttcca gatcttttcg cttatccagg agagaattaa ctaagagtct ggtacctttt   17940
taagtctgat aagaaacatt tacaatctat tctctctgaa gcctcctacc tggaggcttc   18000
atctgcataa gagccttagt ctcagaagcc cctttatgtta atgcagatac tcccttctat   18060
tgatttcaag actttaatca gaaaacctct gagtcttcct atgacctgga agccccccact   18120 tagagttgtc ccacattttc agacccaacc aatgtacatc ttacatgcat tgattgatgt   18180
cttatgtttc cctaaaatgt ataaaaccaa gctgtagcct gactactttg ggtacatgtt   18240
ctcaggtctc ttggagctgt gtcatgagct attggtcact catatttact tggctcagaa   18300
taaatctctt caaatatttt atagagtttg actctctgtt gacaagtcct agttttaaaa   18360 cagttttat ttcatttatt tattttgaga tggggtcttc cctctgtcac ccatgttgga   18420
gtgcagtggc acaatctcag ctcactgtaa cctctgcctc ccaggctcag gtcatcctgc   18480
cacctcagtc tcccaagtag ttagaaccac atacgtgtgc caccatgtcc agctaattttt   18540 ttgtatttttt gatagagatg gggtttctcc attttgccca ggctggtctc aaactctcta   18600
agctcaggca atccacctgc ctcagcctcc caaaatgctg ggactacagg catgacccac   18660
agcgcccaac caaatgact tgttttaga caagaggtta gaaatttttt ttcctcaaag   18720
ggccagacaa taagtagatt aggccagggt ttctcaacct caacagtatt cacattttgg   18780
gccagataat tctttgttgt ggagtgcttt ccttttcact gtagggtatt taactgcatc   18840
cctgacttct actccctagg tgccaataac atcttattct cagttgtgac aataaaaaca   18900
ttttccagac atttctagat gtcccatagg aggtaaaatt gccctgaggt gagaataact   18960
ggtatagact ttgcattcca tatgctatct gtcacaacta ctcagcagtg ccattatagc   19020
acaaaagcag ccatagacaa tatgaaaatg aatggacatg gtactttccc aataagtact   19080
atggaaactg aaatttaaat ttcatataat tttcacatgt aataaaatat tccttaaaa   19140 atttaagcat ttagagatgg aaacccatt gttagcttgt gggacaaaca aaaacaggtg   19200
gtaagccata gctttccaac tcctatttgt tttattttgt aaagtttaat aatatatgta   19260
atttaaacta ctgtatccaa ataatattat tttaacatgt ggtaattata aaaatcaatt   19320
cataaattca gtatgtattt tacatttata atacatctca atttgtacta gccacatttt   19380
aagtactcaa tagtcatata tggctagtag ctaccatatt gggccatgat gccctagagt   19440
atttgctttt aattattagg catacttcct ctcaagaggc cctagtcatt gggaacatga   19500
ggtcactttc tctttgaagg taaaagcctc taagtcctgt tattgatcta aactcacaca   19560
aaaaaaaaaa aaactgaaag taaggtttaa aagaccacca tgacaatatt tatccaattt   19620
gtgactgtat ttctgattgg caattcaaaa ttttgtttgg cttagtaatt tttcttgcta   19680
tcttgaatag aattaatccc agaaggtctg gtagacaatg agtgttttgg tgtaactggg   19740
```

```
tttctttatg tacaaagcta cagaattccc cttgaagaca ctggccttga catccctgaa    19800
atagcaaaat agactttttt gtttactcca cgtgtagtat atgacagtta gtgcattgta    19860
gatagggcca tctattgaaa tctacatgtg attatactct atcgaacatc tactttaaaa    19920
cagcaaacat gagagcctac aattgacatc tcactgttta aaaaaaacaa tttcacatat    19980
atattcacaa acatactaaa gtggtcaata ttcaaagtaa agactcagat attcctcact    20040
ttgcaccatg gtttagttaa ataatacaag taccccaaca acacagttta aatttcagtt    20100
accatggtat attgactgtg atattaaata aagtacaaat ttcactgcta ggttttcagt    20160
atgtaaatta ctatataact aacagatgtg catcatgatc aattatgaat cacatcactt    20220
ctttcacagt ctttggtgac tggtcactta tcagctattc agtacatgtg cagagaacaa    20280
accatgtgtt tgtgttgcct ctttgtctgc cagtgataaa cccaagtgac atttaacaaa    20340
aacatataat gaaagaggga attggccaat aaaaatgaaa gctcaagaaa gaaactaaag    20400
tcacaatgct ggaaatgaaa ttcaaatcaa aggtaaatga agttatagag gaaacagctg    20460
actgtgggaa tgttgacact ttcactggtt ggaaaggcta tatagatatg aagccaaagg    20520
aacttagtta aagcagacat tgacataaat gaggaatttg gttgtgacaa gcaatgccta    20580
ttttagacca atggcttgta tcctcattag ggactgtcag tataccaaaa gaatgggtgt    20640
taagtctagg aaaattataa tcatcattaa gttgactttt agttcccaag atttcctata    20700
attactgttt tcagtattta gatattactg ctaatggtaa aatggcctat gagtagaaaa    20760
tatgaaattt acatttctct ttatccaaat ttcctagtgg aaccctgccc ctaacaatgt    20820
ttaccacttc ttactgtcca ttttcacaga tatgggggac atgattacat gccctcaacc    20880
catatgtttt ctaggtaact ctaccacaga ataaagcggt actcaaatta ctctcagctt    20940
gcttaatatc cactttagga cactgaaaaa caaacacaaa gggactaaac aagatgaaca    21000
gtacgtatcc catttctttt aagtccacta tcttgatatc atgaggcccc ctcactggtt    21060
ttatgtagat gggctactgg aatgcataag ctagtgccaa ttcttatttt ccaaagatgt    21120
taaaagatta acataggatg ggaggagagt gaggatcaaa aaatctacct atcaggtact    21180
atgctcacta ccagtgtaat gaaatcattt gtacatcaaa gcccatgaca cacaattttac   21240 ccatggaaat ttacccattg gcttttgctg caaaagtacc ccttgaacct aaaataaaag    21300
ttggaagaaa aaaacttaac atagcaaatt cttagacatt gttctgactt gtttgcaaga    21360
cctatgcttt cttcctaagc tggtgctgga tagttctttt gacttttttc attattgatc    21420
ttctctctcc ctagcattgc caccaaggga aactatttca tgtaagacat tcttttccat    21480
ccagccatct ggttggccct aatttctctg agcacatctt tcccacctgt attgtgaacc    21540
atagagcagg cctaagggaa ggttataaag aaggtaaggt tggtctgtat tgtctcagtc    21600
tcttttaata tctattccct tctgtatggt actccttctt ctcagagact cctgttctct    21660
agcttcttca taatcggctt tcaaaatagg atctgctgtc agcgatttat cccctttagtg   21720 ctaggatggt aaataaattt tatcttgcat gccaactcta aattattagt agcagccacc    21780
tgaaatgcta cgtgaaggat tctggggatg catccagttg aattagttat gagaagaaaa    21840
attggctact ataggaaaga gaatcaacaa ttcaatggat taaacaaaaa gagtgttaat    21900
tatttcttac atgacagtat caatgtaaaa agttcaaatc agagagggaa ttctgtttct    21960
tagtcattca gggacttgat ttccttccaa gtcattgtac tttcatctca tagggaatca    22020
ctcccatctg tatactgaaa ctgggtagcc attacatctg agttgcagct ggtgggagaa    22080
agtatggaaa ggagagcata ccctatgtct taggacccag gcatggaaat ggcatacatc    22140
```

```
acttctactc acattttatt gatcataaca atcatttggc tgcacagaac tgcaaaagaa    22200
gctgaaaaat gtaccctagc tgggcagcca cacatcaagc aagaatggga gaatgtattt    22260
tggtgggcaa cgagcatttt tgtcccttac taggcttaac aggaatcaat gctatgatta    22320
attaatgaaa ttttccacga gttggaaaaa aactgtggca tccacccata ttatggtatt    22380
agctgatctt gccttaagtg tgaaatggaa gtcttgtttt ctttcctaga gggtcctgaa    22440
gtttaaatat aattccaaaa aatttgacag gcattttcca ctatgagaaa ggtacttttg    22500
ttaggtacaa aaataaactt gtccctgctt tatcacttaa tgtagaatca aagattcgtc    22560
tccagataac agaatttcag acatcagcta ccaaggaggg aaaatatagg cttgggaaag    22620
aaggccttct tgtatgaaat cacaccacac aggcactaga cagctctact tatataaagt    22680
ttagctctat aaaaatgaga ttggggtgtt tcagagattt tattaggaaa tgtacagaga    22740
aaacagttga tggggcaaaa gctataaaca ctaaggtgag aaggaatcag aatataggca    22800
agagttatag aagcatctaa atggcatttg tatctgttta atcagcctat caggtaaatc    22860
tgcccacttt tctccctacc agtgaacatc tgttttgaac ctctaggata tgggacctct    22920
tgcttgatac cagtctttct gtgcctacct attctaaagc ctgatgtcat cttctgtgcc    22980
ttcccttata ggcttacttc cttcaacgct gaccattcct ccagcatttc ttattctaaa    23040
gaggaacagg taagaaactt cgttggaggg aaaattaagc aaggattggc attagagagg    23100
gagctgtgca cagtccctgt ctcaacaaaa atagcttaag atgagacaag tactttactt    23160
agcataatct tgctactgaa ggggctattc taaatgtccc cccgcccaac accattatgt    23220
aaacattctc taatattcgc tacttaattt agattatcca cccttccttc tggccattgc    23280
attccttatc tagcaatgca ggaaaagggc aagaaatcaa agggaaggaa taaagggact    23340
tctgtttcca gactgtattt taaagggaag tcatggttgg ttagcgattt tctttagctt    23400
ttgctttgcg tttgcagaat agctaatatt attgttttac ctatgggaac tggtatccaa    23460
tctagtgccc aatggggctg ttgttactag agctatttc tgtgaacctc atagcagact    23520
ctcttctgct gaaaatgaga tttactattc attctgggtt ctctcaaaag ccagcctgcc    23580
atctacaatt agcggtcaca tccatttggc tatagttcag gtaagtccaa ttcttcatgt    23640
cctgcttctc agctctctgc tgctcagagc caaaaacctt atcttagaac cccaaaatac    23700
atgtctagtt gctgtatcaa agaccaggta gcagccttta cagaaagtcc cttttctcag    23760
aatctagttg agccaatact atgcagtgtc cactatattc ttcttggttc attctctttc    23820
ttttggaggc aacagcttac tatggtgagg acaactggaa tccatctcta cctattcacc    23880 acttttttaag tagtaaaatt ggtagctcaa aagtaacttt attccctgct aagtcttgct    23940 cttccaatt attattcaaa catgagaggt gacagtgaga agattggttt ggcattatag    24000
gatggtacca tgcaaggtac tctaacaacc ggccttctgt ctcatggtct atctccctgc    24060
agattcaggt tgcatcagct gtcctcctat gtccacaatc caaatgctat gggatactat    24120
ggcagacaag ttttccagtt cttcaggaag tagcaactgt gagtattcta gctcacaatg    24180
ggaggagcac aacgactgga ctccagccat gagcaaatac aagtaaaggt ttaactgaga    24240
ctgtctgctc cccagttctc caacccctgc ctaccccaag cccctttttg tcttgattta    24300
tagtagaaaa gtaatagtcg gtcgggcgcg ggggctcaca cctgtaatcc caccactttg    24360
gaaggacgag gcaggtggat cacccgaggt caggaattct agaccagcct ggccaacatg    24420
gtgaaacccc atctctacta aaaatacaag aaaaaaatta gctgggtgtg gtggcaggct    24480
```

```
cctgtattcc cagctactca gggggccaag gcaggagaat catttgaacc caggaggcag   24540
aggttgcagt gagctgagat tgcgccatca cactccagcc tgggcaacaa gggcgagacg   24600
tcatttcaaa aaaaaagaaa aagaaaagta atagtcacaa aatggatata aaagagagg    24660 taacaatggg aaactacagg ggggcaaatt aatacttta tagtttcagc agacctgtag     24720
taacagaaga aaaactgatt ttcacttggt tcagactatc tccctgggct agaaagtata   24780
gggccaaggt agaggaatcg gaggtagatg aattatcttc ctgtgtcttc ctttaagtag    24840
ttcacattgc tcccatttag gtaccagtta atagtcataa ttactataat ccctctcttt    24900
ggatattctc taagacttta tttcctcgtg agcataaaga cataaaatag tacactggag    24960
gttagctatg attaggaaga gccattctaa ctgtaaatta ctcataatcc aagctctttc    25020
ctgatgagca tgtatccgtt ataaaagagg ctatgataat atacagtgag aaaagaattt    25080
gtttagaaat taagtgaatt tggatctagg gtcacctcag ctatttgcg ctgcgacatt      25140 gatcaagtta ttttctctgg gtttcagatg cctcatcttt attttgtgca tttagataca    25200
caattctaat tggcccaatg ggaattacac agctaacacc atcatgcagc aaaacaaaat   25260
aaaatacagt ggaactgaag tgagggagta aaaccaccac actatgcaga tgagactatc   25320
tgcctagtaa caagacattt cttggactct ggtacttcag ccaaatgtcc tctgggagtg    25380
gagaggcggg gagacaatat agtccactgc cagaaagaac ccacatctgt tccaccactc   25440
tcattgtcat tgcgtttcct gggatacttt cagaataatt cattagtaac aacaacaaca    25500
acaacaaaaa aaaaaaacag caaggaaaag gctacaaggg gaagggtttt tctaggtctt    25560
tgggatatat ctaatcattt cttcacggaa tattataaag tagggtccac tcaaagctca    25620
tccctcacaa gccactcaac ctttgacatt cttcttctat ttaatgtgag tcagaattcc    25680
taagattttt tgaaatcctg cctgcaaagt ctgcttatga atttttttcc ttaccacgga     25740
gttcccataa agtgacaggt tctgcctaag tagttagcta cctgcaaggc tgctcgaatc    25800
caactttctt tcccactcta cttttgcattc tgctctccct ttgctctcct ctccttaggc    25860
cctcaagtga tgccagcttt tgttctagca ctctagaaag gagttactat tttgatccag    25920
agtacacaga gaagagaaac tggagtgggt aaaaggaagc tcgtcactga gaatgctggt    25980
actgggagca agactgtggc aaacccagga aatactaaca ataagaaccc ctcaaaagtt   26040
cacctttacc aagccaatgg aaacaatata gctgagtggg gtttgaattt tgagaactaa    26100
tgactcctca gctaccatgt aattgccttg gtgctccatt tgctataatt catgggaaag     26160
gtactaaggt ccttcaactg gttttccttg ctacctccac ctttttcaga agttggacct    26220
atgattagca cacttcctgc ctatccattc acagtgaata gaatggctgg ctaaatttta    26280
aaccccattt aaattattcc acttcgaaat ttgaatgata gatgcttgcc taagtctact    26340
ggcctcagta acattacctt ttctcatgac caagggtaaa agagtaaatt gataggaggc   26400
acaagttttt gtggatgtgg gttgggctgg caccaaatcc aactacaagc atacagtgac   26460
cacttcatac acaccacata aaaaatacaa aaactgaaaa atactatcaa atgctttgac    26520
attttctaaa tatttctgct gcccctataa aattgccttg tctgaccttt cctcactaac    26580
caggagatac ggtgtttttc atttcctctc ccttcaaatt ttacaagaga atcaaggaat   26640
ttgaggacca aagcaccaca aacacaagag taagcacagc aaatatgaca aggggactga  26700
agtaagcccc tatgggaata ggatctgctg aaggaatcaa gagggatgga caaaggaaca   26760
gaagacactc aagaataact tcaggaagtc tccttaccgc ctcacctgct ttccctctgt     26820
cctacacatc cagccttgca aagaaataag agtaaagaga aagtccatg tagcaccatc     26880
```

```
ccagttcaga agcaaccccc aagatatggg tcaactttat cacctcaaac tctactcatt    26940
tataatgaca aaattcaact gttaacacat aggtaagagt tcttcaggca tcggttttaa    27000
aggtccatgt actgggacgg gtgcggcggc tcacacctgt aatcctagca ccttgggagg    27060
ccaaggctgg tggatcacct gaggtcagga gttcaagact agcctggcca acatggtgaa    27120
acccagtctc tactaaaata caaaagttag ccgggcatga tggcgggtgc ctgtaatgcc    27180
agctgttctg gaggctggga cgggagaatc acttgaacct gggagacagt ggctgcagtg    27240
agccgagatc acaccactgc actccagcct gggtggctga gcaagacact gtctaaaaaa    27300
aaaaaaaaaa aagttcatat actgaataac catctgggcc cataacagct taagactttc    27360
tggagaaaaa aaaaaaaacc agtttccagt ttaatttcca acaaagcagt aggaactctt    27420
gcctatagaa tactgtgctg ggggctgggc acggcgactt atgcccgtaa tcccagcact    27480
ttgggaggcc gaggcgggtg gatcatttga ggtcaggagt taagagacta gcctggccaa    27540
aatggtgaaa ccctctctct actaaattaa atacaaaaat tagcctgctg tcgtactaca    27600
cgcctttaat cccagctatt cgggaggctg aggcacaatt gcttgaacct gggtggcaga    27660
ggttgcagtg agccgatcac accaccgcac tccagcctgg agacagagcg agactctgtc    27720
tcaaaaaaaa aaaaaatact gtgctggttc atttgcctat aaagtcacca atctaatgtt    27780
tgggtatttg atcattcaga attctagaaa cactgaagat cccttcacct actcagggtc    27840
tgggcctctt tcatgaatgc ttaattccca cagccttaca gtttataccc ttctcctctc    27900
ccacttttga tcctcaagtt ttttgcttct cacattttt actgggtttg tgcttctcag    27960
tatccttgac caaagcaact gatgctgtaa gaaatgagac ttcaaaccat ttacccacac    28020
tgggtgatta aggtagttta aaaaagaaa tgaggccagg cacggtggct cccgcctgta    28080
atcccagaac tttgggaggc cgaggcaggt gtttcacttt aagtcaggag ttcgtgacca    28140
gcctggccaa catggcaaaa ccccgtctct actaaaaata caaccattag ccaggcatgg    28200
tggctcatga ctgtaatccc agctactggt gaggctgagg caggagaatc gcttgaaccc    28260
aggaggcaga ggttacagtg agccaagatg gcaccactgc actccagcct gggcaacaaa    28320
gcgagactcc atctccaaaa aataaattaa tttattaatt taaaaagaaa aagaaaaaag    28380
aaatgaagaa cttacggtaa ttagtgtggt tagggacagt gagttagaaa ttgtcacatc    28440
aaaatacaaa gttttcaaaa cagtatattt tattttacaa tagcaaccaa ctccccagtt    28500
tgtttcaatt gtgacatcta gatggcttaa gattactttc tggtggtcac ccatgctgaa    28560
caatattttt caatcttcca aacagcaaag actcaaaaga gattctgcat ttcacatcag    28620
ttcacaagtt caagagtctt ccatttatct tagcttttgg aataaattat ctttgaggta    28680
gaaggacaat gacgaagcca cttaattcct tgtgtctgca taaaagcaga tttattcatc    28740
acaacttcat ttatgtgaat aaagcagatg atgataaaat gttctcttat tcttgtttaa    28800
tcagtagtgg tagtgatgcc agaaactgtg aaaggaaggc ttttagttac tttcttcttt    28860 ccatttttcca ataatccatt ccccatcccc agctgaagaa aggggtgtta ctgagtccag    28920
ctgataccac acattgaaag gtaaacatta atatttcaaa tctgatgtct aactaaaaat    28980
gtacagaatg aaaactagaa aatttcaacc ccagattatc ttcaaccttg ctccctccac    29040
caatcatact ttgacattta tctatttcct tctccactta tggatgtaat tggcttgcta    29100
tagaaactac agttcagatg ctttgaatgt atgaactaca atgaacaata aagtcctctt    29160
cttttgaagc atattttggc ttcagcttta agataatctt atgacaagaa gggtcacact    29220
```

```
gattcactta ataaattcca ttcttaccta acacaaggtt tagttgataa gcacttggac   29280
aaaaataata cttttcaaaa atgtaaagca aactagtgag gacaaaggat tttgtcctca   29340
tctcaacaat gatcagctat tggaactgca tgaaactgaa caatttaaac ctggagctgg   29400
taatgttctt aagaccaatt cagaacaaag gcaggttgcc cttaaaacag gtttgacctt   29460
ttccttcact cttcctcctg tcccaccctc tgtgagtgat ttaaaaacgg aaaaggtcaa   29520
agcccagcca ggcctacatt tagagaaatt ttaaaaaaat ttttcctttc aattttggcc   29580
aattatttcc aattttttatt ttattcttaa aacttaagca tggtaaaatg ttaagctgtt   29640
ttcatccact gatattattc tactataaaa agcccttctt gagcagattt gatgataaaa   29700
aggagaacat ttctaaggta taattagaga agctgttgca tgagaaatca tgtctccatc   29760
tccattttgc tatgcgttat ctgaggattg tttctgaaag agatctattt aggcagtgta   29820
tgtatgtgtc agcatgtaaa aagtaaagaa ctgaaaatag acaaaccttg taaatgcact   29880
tcaaaaccaa ttgtggctca agtgtaggtg gttccccaag gctggtacca atgagactgg   29940
ggtttgggaa ttagttggtc atcatccctc ctgctgccca gcagtggtca gtcatttttc   30000
atgagggatg gactaggaaa atgaagtgtc tattataagg agagttcctg taacttaagg   30060
agcaagctca ctacaaaacc cagctacctg cttatcgtag tggccagagt ggtagaagag   30120
atacggagta ggaattaaac cacacaatgt tatttaggga ctaagccatg cccctaacaa   30180
gaaaacaagc caaaggaaa gtattaggca ttctctggga aggcatgcat ttttttccca   30240
tgtctctggg gccaaaaacc ttataccaag tacctattgg cacccgaata tatttgtaga   30300
atgaatgaat acatgaaaaa aaataaacag taaccttttct cctatattct actttccaag   30360
ccaattaata agcaagtgtc ttttcgtcat gattttttt gttttctgtt taggatttaa   30420
caaaatggtt gagataacag tcacttctgt ttgatgaaga gtatcacttc attccatttt   30480
tgtgtttttg ttgcatctcc aagtcagaat aaatgccttt tggagcagat atatttcatt   30540
tagcatttag tatcatcttc atcaatactc gtatgaacga aaaaataaaa agccctctct   30600
tattcccact ctacaacgca tgtcaaaggt gatctgttta gttttccctt agtatcgaac   30660
atatcacagc tactcaatga agtttcttct caactaaaga aacacagtct cttagagaat   30720
ttgttcctgt gttccacca aagataaat gagataaagt gcactttggt ttacgtctttt   30780 caagcactta agaacagcac tttattcagt tttataaaat ttttactaaa ttggtaaatg   30840
caaaagaatc tttttttttat tgctcatatg tcttcctgtc tctaagccag accaatgagc   30900 aaaataccttt aaaactagtt gttacatctt gaaccattta actgtaataa agcagaatg   30960 tttagttaat gaattaaaga acaaaccctg agccctttta tcagtctcct ggctttaaac   31020
taagccaatg aggaagtgat ttgggggatt cctgaaacta ggaaaaatgt ctctttattt   31080
tgaaagaaac ttgcattttt ctttcttttt tttttttttt ttaatctcaa aggcaattga   31140
gtgggtcttc tgggccagac ctatttaatt tacgaaacat agtaccttgc agagaatagg   31200
cattgaaata ttatttaaac aatcaaacca aagatgttct tctatcttca gctgtcagtg   31260
atctaatgcc ctcatctctc ttatcctcag gacccagaat ggtatattcc acataaaaga   31320
tgctttgttt atcaaatgaa tcaaaaagca cgcctgaggc atttatttt actcctttac   31380 ttctgtaggc caggtcaagg tgggtctaat tcacttttat catcagcact taagaaactg   31440
gatggaagac cacaacacct tgttttttgc aaaaatttc catctcctca atcaggccag   31500
gaagcatgta tcttctggac aggactttat ctctctactc agcttagtac actgccttat   31560
attagtccat ttgtcccatg ttttcatcac tgaataaact tgttaaatga cttttggtct   31620
```

```
ggatctcaca cctatattac ttcatttcct tctgtgagca ctctataatg ataacatcat   31680
ttttatatcc tagggcatgt agttccgagc cccacagaaa gtaatcacca ttcagtaagc   31740
caatagttca ttcctatctg tatagaactg taggctttgt aaatctacac atagatctct   31800
gttgtaggtt caataatgat aataaatgtt tgtgccccca gttgttatct ctaaggataa   31860
gagtaatcaa tgatcattca gcagatatag cttatatatg ggtggcagtt tacaaattat   31920
aaattgattt tacacatatt ttcttctgct acccaagaca caataaagat ggtttatctt   31980
tgcatcccca atgcctagca atgagattgg cacacaatag ataactacta tagtggcatt   32040
cttcagacaa ccaatcccct tgcgtatgcgt attcaaaaga taatcattgt tattcaaatt   32100
ttcctacttt atttgcacaa tataataact atcatacaat tttataaacc tagtacccag   32160
caccaagtga gaaaatcaac agttacattt atatggtgcc ttagagttca caaaatgcta   32220
acataggtat tgccttattt ttggctgtgg ctaaatgaaa tatgataaat tttcagtgcc   32280
tttaacagtg agttcacata gtaggcaatc aaaattgatc tatttaacag gtatttaaac   32340
ccttggtttg tataactact tatagaaccc ttctcactgt ggtttaacta tacaatgaga   32400
attttgtaga gacaatacct agcttacaga aagtttttatt catacagaaa gcatcaaatt   32460
tttcatttac aagtgcttta taatttagaa agcacattcg caagctgaat taagtgactt   32520
tcggtctgga tctcacatct attacttcat ttcctcatac tagctctttc ctggttacct   32580
ggaaaaatgt atcagtaata atttaactta acctcaccag taaagtcttg attgtttaaa   32640
attaagcaat atatcattcc ttacatctga atagtataga ggataaactt tcctcttatt   32700
acataggaga attaatcttg tattttacag tacccaaaat agctggtatg taagaggcac   32760
ttaatattca ttcatccatt cattcattca taaatatgta gcccattgac atttgtatca   32820
tgctttagtt tacaaagcac tttaatatgc acctttctga aattttttgt tctatgagaa   32880
tacttttccc cctttggtag ctctagcacc cagcatggta tctggcacat tataggtgac   32940
cacaacaagc ttagtcccctt atgttttcag tatattttaa agtttaaaag cagtttccat   33000
gtgttttcgt ttctgatacc tggaatactg cattttttact caaaattacc agagcagcaa   33060
acacaaattg gcctcaaata tacatataat ttattcattt atcaaacaat tccttgtgtc   33120
tgcatagtac tatatccttt tgaaagagca cttttttatg cttgctcctt tctttgtatc   33180
cacaacgctt atcacagtag aatacaagtg ctttacagtt tacaaagcac attcactatt   33240
ttttttcagg tcacctagat atcaataatc attgcatttt tagtgcctag cacagggaca   33300
ggcacagaaa aggaaactag tagtattcag aaatttctc tgaataacaa ataatacatc   33360
aggggggtggt aagctatgaa cagcaggcca aatccaattg gctcaaaaac taagaatgat   33420
tttgacctta taaaaacgtt gtttaaaaaa caaatatgta acagaaacca tatggcccac   33480
agtctaaagt atttatgatt tgacccctta cagaaaaact gtggacccct gatttacata   33540
atgcttcaca atttacactg cactttcaaa tgttaactgc atgattgcca atacactaat   33600
tggtttttct cttatgtttt acagtgcttt catacacatt atcagtcatt taaatcaact   33660
tcccacataa acaggaagaa aaaaatcaag gaaagtatta aacatgctca acagtcccag   33720
gttctctcat ctttaagcct agagatgggt attaaaccca ggagtagcgt tggcacagtc   33780
caccaaatta tttggccact actatgagca gggagttcag gctgtcccct tgggacctcg   33840
ctttgtccca ggcacagtca ccctttccat aaccatcact agaaatccca aaccccagaa   33900
tcctgctcac ctaagctcaa agaaggaagc tgttgctggc aggtgcttct cagaagtctg   33960
```

```
gcacatctgt gtatttcttg tctaattctt ctcattggcc tggagcatct cttcacattt      34020
ttctctagag agcctggcac ttttttttcc ccaacaacct gaccatttta tcttctcagt      34080
ctagggcttc tggggtcaaa agaaaggact gaaatacagt atcacctata tgaatgtctg      34140
ctcctgaggg aagttaacaa aagccagatt agatactgac tggattttgg tgtctctctc      34200
aagtggagaa gatgtgaata gaaacagaag tttacaaaac actatagcct aacaaatagg      34260
taaaagctgt gatttaaagc tggctcaaga ctggcccagg cataatactg tcaatctaaa      34320
ggtaaccggc aacatcaaaa agtacatctc aaaagaatca ggcttaaaga taaacaggag      34380
aactggaaat atctaagagt aagaagtgta aacaatagaa aagaggtagg gtttagggtt      34440
ctcatcttgg gatttcccca ggtcttcaag cttctatcct tcctgggttc tgggtcatgg      34500
gcctccagat tccggccgtt agtcttgaga tacctttttc gcttgggtcc tctatccatc      34560
taggtaggct ttgtgacagg ggccttccat ccttgggttg taggtcttcc agctacaacc      34620
ctgggctaat cttaggtcgt tggccttgtg tcacaagtct cagttcttag gccttccatg      34680
tgtcctgtcc caggtcttaa gacttctaac tcaagccttg agacttccat ccaactcagg      34740
ccttcggtcc aattcaggcc accctctgtt ttcttggctc ttgaggcttt tgttggtttc      34800
aggcctgagg cttctatcta tcttggaaca tgggcttttcc atcttagtcc tcgggtctca      34860
agtctcaaac catctgtctt atactttggg ccttctatcc atatgagcct tccaccttct      34920
gccctacttg agttctgggt tttactgcag tctagggcct tgttttggtc ttggatcatc      34980
tcacatggca gcctggcata aggaaccgct ccacaatgct tgctctgata gccgacgttc      35040
tgcacctatc aggcaggggt taggaagccc ctctgccaca catgacacac acacgtac        35100 acttgcccac atatgcaaag aaatatttaa ggagagatta catgaaatca aagagaggga      35160
gatagattca tgaagaggct gaaatactca aaggtgagta gaaagggaag aagcagagaa      35220
caaatacaag ccaacagaga ttaatactga aatagaaaat cacaaacagc aagagatgct      35280
gaggcacgca ggggaggaga gagagaatag cccaagagag gcagaaagga aatgcagaaa      35340
tgagaaatgt gagataaaaa gtagaaacag cagaaaggag gccagactca gaaaaaaggt      35400
gaaatttaaa acgaacgaga aggggaaggg gtaacaaata atcacagttc acaaagaaa      35460 aagagaggta ggcagagaaa ggagaggtag acagaacaag aaaaggacaa aaagcacaca      35520
gcatgtgacc caaaaaggag acatgaaata aagcgtgaaa aagagccac atctaggaga      35580 gcaaagagaa atagcaacaa aatgaaaaat gagagatatg tctaagacaa gacacagacc      35640
actcttgtga acaaaaagag aaaatgaggc aaaggcacac acgaaagaaa ttagcaagag      35700
aaacatggaa atgggtaaga cacactttag atagagaaca aagagcaaag acaagaaaga      35760
aagagacaaa gaaatacaca cttgagtgca agagataagc aaaggcagac attcaggaga      35820
agtaagtagt agaagaggca agatacagtg aggggcacaa gaggcatgaa aagcatcaca      35880
gaaagataaa aaaatcaaa aagtgtcatt agtaattata ataaactatt gttactacga      35940
atactactta tagtactaca ataataacaa ccaccaatac caacacagat gctcttctat      36000
ttataaactt ttaccttagg gatttcttac atagaaccaa agcatgccaa ctctgcctgc      36060
tacctgatag tgctagtggt cacttatatt gtgggaaatg aacttatgag tcttcttggg      36120
ttacctttta cttgacatgt gccaggcact gcaataggtg agcactttac atacatgatt      36180
tcatttaacc ctcacaaaca gagaagtcta gagactttaa gttgtcaaag gtcatatacc      36240
taatgagtag cagaggattt aaaacacaca atgtatgcct cttaacatcc tgttacaact      36300
atttactagg atttctggaa gagccaaatg ggatgtcaca gatgactaag tattttcata      36360
```

```
aaaggctctt tgataggact tgctcaatcc cctcctttag catcaccttt ccccaactct    36420
ttagaaaact gacttcattc tcacactttt ataatggcta cttcagagtt tagttttctt    36480
tttacactaa tcttaactga cgacagagtc tctcacaaac ggagatgaga aagggttacc    36540
ctttcagcag aaagcagaaa tggtgtttta agcttctcaa cgtttaaggc tctaagaatg    36600
acagagggcc tatacagtga agacatagaa cacacaagca aaggctaaat tcttctgtga    36660
tacaactggt aagaagacca taatgtcttt gagttgcttc agtgaaccca gtcagtaata    36720
tggaagactg gtcatctttc catctcacat ttagccccac ttcacattag accaacacac    36780
cccatccaac accagctccc aaaaaacagc tgttataaca gttctgaagt gatcctcaca    36840
ggactgcaac atcaacaact tacttcattc agctatcctc aagtgctaga gtgccaggca    36900
tgttgatctt caggtgggaa ggctgacttc cttcagtgtg ttcaaatttc ttggacctgc    36960
tgaagactca gctctctgca ctgcttgtag gaagtataat gatttggcag ataggaacaa    37020
tgaagag                                                              37027

<210> SEQ ID NO 46
<211> LENGTH: 113
<212> TYPE: DNA
<213> ORGANISM: Artificial Sequence
<220> FEATURE:
<223> OTHER INFORMATION: Y RNA-1

<400> SEQUENCE: 46
ggctggtccg aaggtagtga gttatctcaa ttgattgttc acagtcagtt acagatcgaa      60
ctccttgttc tactctttcc cccttctca ctactgcact tgactagtct ttt            113
```

METHODS AND COMPOSITIONS FOR DIAGNOSIS AND MANAGEMENT OF DIABETES AND METABOLIC SYNDROME

CROSS-REFERENCE TO RELATED APPLICATIONS

This application is the 35 U.S.C. § 371 national stage application of PCT Application No. PCT/US2015/062912, filed Nov. 30, 2015, where the PCT claims the benefit of U.S. Provisional Application Ser. No. 62/086,052 filed on Dec. 1, 2014, having the title "Methods and Compositions for Diagnosis and Management of Diabetes and Metabolic Syndrome", both of which are herein incorporated by reference in their entireties.

STATEMENT REGARDING FEDERALLY SPONSORED RESEARCH OR DEVELOPMENT

This invention was made with government support from the Veterans Affairs Merit Review Grant #821-MR-EN-20606. The government has certain rights in the invention.

SEQUENCE LISTING

This application contains a sequence listing filed in electronic form as an ASCII.txt file entitled 02305108.txt, created on Nov. 10, 2015, and having a size of 171 KB. The content of the sequence listing is incorporated herein in its entirety.

BACKGROUND

Diabetes mellitus is a complex and costly disease that is increasing in prevalence worldwide. In 2012, it was estimated that diabetes costs the nation $245 billion, a 41% increase from costs incurred in 2007 (ADA study "Economic Costs of Diabetes in the US in 2012"). According to the American Diabetes Association (ADA), about 9.3% of the United States population is diagnosed with diabetes. Diabetes remains the seventh leading cause of death in the United States and caused about 69,000 deaths in 2010. Diabetes was listed as a contributing factor or underlying cause of an additional 234,000 deaths in 2010.

Despite increased awareness, treatments, and management approaches, diabetes not only remains a significant health issue, but the incidence of diabetes is on the rise. As such, there exists a need for improved diagnostic, treatment, and management methods for diabetes.

SUMMARY

In embodiments, provided herein are assays including the steps of contacting contacting a sample from a subject or component thereof with a capture molecule, where the capture molecule can be configured to specifically bind to a biomarker, where the biomarker can be selected from the group of: 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y RNA-1, and combinations thereof, detecting specific binding of the biomarker to the capture molecule, quantifying an amount of the biomarker that is specifically bound to the capture molecule, and making a diagnosis or prognosis of diabetes, metabolic syndrome, a pre-diabetic state, or early onset of diabetes when the amount of the biomarker that is specifically bound to the capture molecule is greater than or less than a control, a standard, or a predetermined threshold value. In some embodiments, the biomarker can be a cDNA molecule. In embodiments, the sample or component thereof can be a bodily fluid sample or component thereof. In embodiments, the bodily fluid sample or component thereof can be a blood serum sample, whole blood sample, saliva sample, or a urine sample. In embodiments, the sample or component thereof can be obtained from a subject having or suspected of having diabetes or metabolic syndrome. In embodiments, the biomarker can be gas5. In embodiments, the biomarker can have a sequence that is 80-100% identical to SEQ ID NO: 12. In embodiments, the biomarker can have a sequence that is 90-100% identical to SEQ ID NO: 12. In embodiments, the diagnosis of diabetes can be made when the amount of the biomarker is less than the control, the standard, or the predetermined threshold value. In embodiments, the step of detecting specific binding of the biomarker to the capture molecule is performed using a method comprising a technique selected from the group of: array polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing, cell-based RNA detection assays, in situ hybridization, northern blot analysis, and combinations thereof. In embodiments, the sample or component thereof can be obtained from conditioned media of an adipose cell culture, wherein the adipose cells in the adipose cell culture were obtained from the subject. In embodiments, the sample or component thereof can be obtained from an obese subject. In embodiments, the sample or component thereof can be obtained from a non-obese subject. In embodiments, the assay can further contain the step of processing the sample or component thereof prior to contacting the sample or component thereof, wherein the step of processing comprises a chemical method, a physical method, or combinations thereof to release, concentrate, separate and/or isolate the biomarker or other components of the sample. In embodiments, the step of processing can include obtaining an exosome preparation from the sample.

Also provided herein are kits containing a capture molecule, where the capture molecule is configured to specifically bind to a biomarker, where the biomarker is selected from the group consisting of: 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y RNA-1, and combinations thereof and instructions fixed in a tangible medium of expression where the instructions provide for diagnosing or prognosing diabetes, metabolic syndrome, a pre-diabetic state, or early onset of diabetes when an amount of the biomarker that specifically binds to the capture molecule is greater than or less than a control, standard, or predetermined threshold value. In embodiments, the capture molecule can be attached to the surface of an array. In embodiments, the biomarker can be gas5. In embodiments, the biomarker can have a sequence that is 80-100% identical to SEQ ID NO: 12. In embodiments, the biomarker can have a sequence that corresponds to a sequence that is 90-100% identical to SEQ ID NO: 12.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
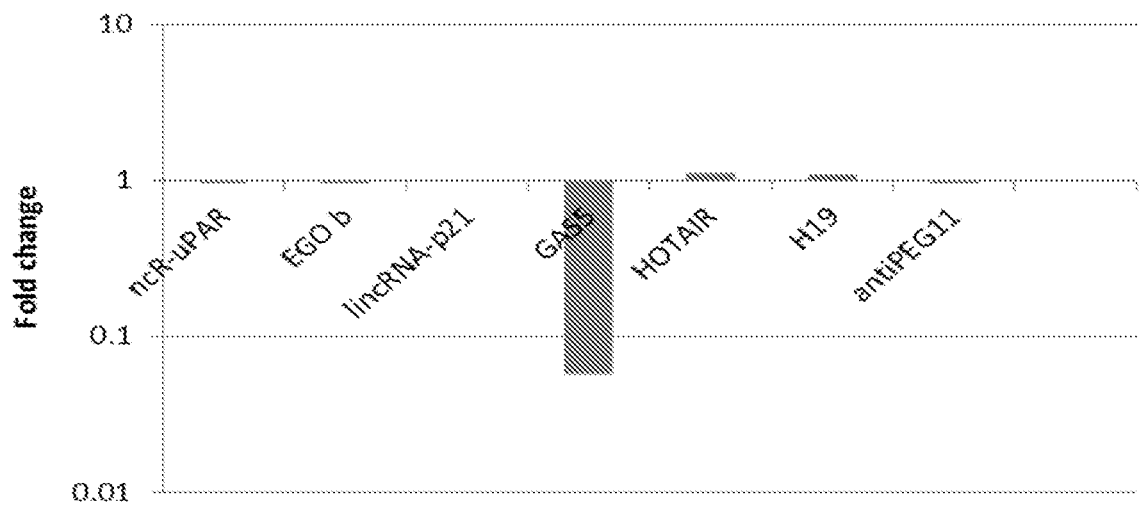
FIG. 1 shows a graph demonstrating the fold change in lncRNA expression of detected lncRNAs in serum from diabetic samples as compared non-diabetic samples.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

The definitions provided here refer to the terms as they are used herein unless otherwise defined herein.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "specific binding," "specifically bound," and the like, refer to binding that occurs between such paired species as nucleotide/nucleotide, polynucleotide/polynucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. "Specific binding" can be characterized by the binding of one member of a pair to a particular species and to no other species within the family of compounds to which the corresponding member of the binding member belongs. "Specific binding" can also occur when enough binding of one member of a pair to a particular species occurs such that the binding of the member and the particular species can be deemed statistically significant as compared to the amount of binding that occurs between the one member and non-specific binding species. In other words, "specific binding" also refers to the binding between one member of a pair to a particular species that occurs at such a rate or an amount so that the signal to noise ratio allows detection of this binding interaction amongst all other binding interactions that occur with the one member of the pair. Thus, for example, an antibody preferably binds to a single epitope and to no other epitope within the family of proteins or a polynucleotide preferably binding its perfect complementary polynucleotide as opposed to binding a partial complementary polynucleotide.

As used herein, "differentially expressed," refers to the differential production of RNA, including but not limited to mRNA, tRNA, miRNA, siRNA, snRNA, lncRNA, and piRNA transcribed from a gene or non-coding region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" refers to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic or non-translated RNA molecule including but not limited to tRNA, siRNA, piRNA, miRNA, lncRNA, and shRNA.

As used herein, "deoxyribonucleic acid (DNA)" and "ribonucleic acid (RNA)" generally refer to any polyribonucleotide or polydeoxyribonucleotide, which can be unmodified RNA or DNA or modified RNA or DNA. RNA can be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), long non-coding RNA (lncRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" refers to a small non-coding RNA molecule containing about 21 to about 23 nucleotides found in organisms, which functions in transcriptional and post-transcriptional regulation of transcription and translation of RNA.

As used herein, "long non-coding RNA" refers to a non-coding RNA molecule containing about 200 or more nucleotides that are not translated to a protein.

As used herein, "purified" is used in reference to a nucleic acid sequence, peptide, or polypeptide or other compound described herein that has increased purity relative to the natural environment.

As used herein, "about," "approximately," and the like, when used in connection with a numerical variable, generally refers to the value of the variable and to all values of the variable that are within the experimental error (e.g., within the 95% confidence interval for the mean) or within .+−.10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or an active derivative thereof, such as a metabolite, as compared to the host response in a normal or control patient.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal, which can be predisposed to the disease, disorder and/or condition but has not yet been diagnosed as having it.

As used herein, "mitigate" refers to reducing a particular characteristic, symptom, or other biological or physiological parameter associated with a disease or disorder.

As used herein, "separated" refers to the state of being physically divided from the original source or population such that the separated compound, agent, particle, chemical compound, or molecule can no longer be considered part of the original source or population.

As used herein, "capture molecule" refers to a molecule that is configured to specifically bind one or more biomarker molecules of interest. A capture molecule can be a polynucleotide, antibody, antigen, apatmer, affibody, polypeptides, peptides, or combinations thereof that can specifically bind one or more biomarkers of interest. For example, the capture molecule can be configured to specifically bind a polynucleotide corresponding to 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm, Hoxa11as, HoxA6as, IGF2AS, nC-uPARm NDM29, Nespas, NTT, SNHG3, SNHG4, Tsix, Y RNA-1 and/or combinations thereof. Representative polynucleotide sequences for the aforementioned biomarkers and any other biomarkers described herein are demonstrated herein.

As used herein "essentially discrete" as applied to features of an array refers to the situation where 90% or more of the features of an array are not in direct contact with other features of the same array.

As used herein "attached" as applied to capture molecules of an array refers to a covalent interaction or bond between a molecule on the surface of the support and the capture molecule so as to immobilize the capture molecule on the surface of the support.

As used herein "operatively-linked" as applied to capture molecules of an array refers to a non-covalent interaction between the surface of the support and the capture molecule so as to immobilize the capture molecule on the surface of the support. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used herein, "biomarker" refers to any measurable molecule, including but not limited to polynucleotides and polypeptides, or compound in a subject whose presence, absolute amount, or relative amount, is indicative of some disease, condition, syndrome, disorder, symptom thereof, or state thereof.

As used herein, "body fluid" refers to any liquid or liquid-like substance that originates in the body of a living organism. "Body fluid" includes, but is not limited to, whole blood, serum, buffy coat of blood or other blood fraction that contains substantially only the white blood cells and platelets, plasma, cerebral spinal fluid, urine, lymph, bile, acites fluid, and saliva.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more modifications (e.g., substitutions, additions, and/or deletions). A substituted or inserted amino acid residue can or cannot be one encoded by the genetic code. A variant of a polypeptide can be naturally occurring such as an allelic variant, or it can be a variant that is not known to occur naturally.

As used herein, "wild-type" refers to the typical form of an organism, variety, strain, gene, protein, or characteristic as it occurs in nature, as distinguished from mutant forms that can result from selective breeding or transformation with a transgene.

As used herein, "diagnosis" refers to the identification or determination of the nature and circumstances of a disease, disorder, condition, syndrome, or symptom thereof in a subject.

As used herein, "prognose," refers to determining a prognosis for a disease, disorder, condition, syndrome, or symptom thereof.

As used herein, "prognosis" refers to a prediction or forecast of a chance of recovery, complete or partial, from a disease, disorder, condition, syndrome, or symptom thereof.

As used herein, "pre-disposed" refers to an individual having at least one factor known to contribute towards the development of a disease that puts the individual at a greater risk of developing the disease compared a normal (non-predisposed) individual or greater than the average risk of a contemporary population.

As used herein, "non-diabetic" refers to a subject having a fasting blood glucose concentration of less than 100 mg/dL and/or a Hb1A1c level of about 4 to about 5.6%.

As used herein "pre-diabetic" refers to a subject having a fasting blood glucose concentration of 100 to 125 mg/dL and/or a HbA1c level of about 5.7 to about 6.4%.

As used herein, "diabetic" refers to a subject having a fasting blood concentration of greater than 125 mg/dL and/or a HbA1c level of greater than about 6.5%.

As used herein with reference to the relationship between DNA, cDNA, cRNA, RNA, and protein/peptides, "corresponding to" and similar terms refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

DISCUSSION

Diabetes Mellitus (DM) is a group of metabolic diseases characterized by impaired fasting glucose levels. Type 1 (T1) DM is juvenile onset diabetes in which body does not produce insulin (insulin-dependent DM). Type 2 (T2) DM is more prevalent with 90% of adult cases being T2DM. T2DM may be insulin-sensitive or insulin-resistant. The pathogenesis of type 2 diabetes is not completely understood but it is known that several genetic and environmental factors interact to contribute towards this epidemic. Risk factors include BMI, smoking, family history, lifestyle and diet. There is overwhelming evidence linking obesity and diabetes. Within the obese population, patients show insulin-resistance though about 20% are insulin-sensitive. This can be attributed to differences in oxidative stress and AMPK as well as inflammatory cytokines and SIRT1 in the adipose tissue of insulin-resistant subjects. It is also known that some diabetic patients are lean. There are several medications and treatment options available today to manage diabetes and its co-morbidities; however little is known on prevention and prediction of diabetes. Specifically, while protein markers exist to determine that an individual has diabetes, no biomarkers are known to indicate where an individual is in the initial stages of developing diabetes, i.e. is in pre-diabetic state.

Long non-coding RNAs (lncRNAs) have varied functions including signaling, molecular decoys, scaffolding and guiding ribonucleoprotein complexes. Cellular RNAs are divided into coding (mRNA, 2%) and noncoding RNA (98%). Noncoding RNAs are subdivided into transcription RNAs (rRNA and tRNA), long noncoding RNAs and short noncoding RNAs (miRNA, siRNA, snoRNA, snRNA). LncRNAs are greater than about 200 nucleotides in length and have distinct structural and spatial features which allow it to bind to DNA, RNA, or protein partners. Genome wide association studies done in suggested that lncRNAs are important orchestrators of essential biological networks. For example, lncRNAs are implicated in regulation of genes in cell growth and apoptosis, epigenetic regulation, transcription and translation, and splicing. LncRNAs are transcribed by all cell types but its target and mode of action is specific for that biological system. Currently, the involvement of lncRNAs in the etiology or pathology of diabetes and/or metabolic syndrome is not known.

With that said, described herein are assays and methods for diagnosing/prognosing diabetes, metabolic syndrome, pre-diabetic state and/or the early-onset of diabetes in a subject. In some embodiments, a lncRNA can be detected and/or quantified in a bodily fluid of a subject having, predisposed to, or suspected of having diabetes and a diagnosis and/or prognosis of diabetes, metabolic syndrome, pre-diabetic state and/or the early-onset of diabetes is made based on the detection and/or quantification of a long non-coding RNA. In some instances, the assays and/or methods can be used to evaluate a response to treatment or management for diabetes, metabolic syndrome, pre-diabetic state, and/or the early-onset of diabetes in a subject receiving said treatment.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays

Described herein are assays for detecting biomarkers of diabetes and/or metabolic syndrome. Also described herein are assays for diagnosing and/or prognosing diabetes or metabolic syndrome. The assays can be used for the diagnosing a pre-diabetic state. The assays described herein can also be used for diagnosing a state of diabetes or metabolic syndrome or determining a response to a treatment. The assays can also be used for diagnosing an early onset of diabetes and/or metabolic syndrome. Alteration in the normal expression and/or secretion of 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2OT, tug 1 can be involved in the etiology and/or pathology of diabetes and/or metabolic syndrome. As alteration of the expression and/or secretion of one or more of the aforementioned lncRNAs can occur prior to the development of diabetes or metabolic syndrome. Therefore, alteration of the expression and/or secretion of one or more of the aforementioned lncRNAs can indicate a pre-diabetic state and/or characterize the early stage of diabetes. In short, the assays described herein can provide earlier, improved, and/or more accurate diagnosis and/or prognosis of diabetes and/or metabolic syndrome compared to conventional methods and assays for the diagnosis and/or prognosis of diabetes and/or metabolic syndrome.

Capture Molecules

Described herein are capture molecules configured to specifically bind a biomarker that can be involved in the pathogenesis of diabetes and/or metabolic syndrome. The capture molecule can be a polynucleotide. The polynucleotide can be configured to specifically bind to a biomarker as described herein. The polynucleotide can be configured to make a non-covalent bond or a covalent bond with the biomarker. The capture molecule can be modified to include a detection molecule, such as, but not limited to, a chromophore, fluorophore, or bioluminescent molecule, that is activated or quenched upon hybridization of the capture molecule to the biomarker. The detection molecule can facilitate measurement and quantification of the biomarker present in a sample.

Biomarkers

The capture molecules described herein can be configured to specifically bind to a biomarker. The biomarker can be involved in the etiology and/or pathology of diabetes and/or metabolic syndrome. The biomarker can be a polynucleotide. In some embodiments, the biomarker is a long non-coding RNA (lncRNA). In other embodiments, the biomarker is a cDNA molecule corresponding to the lncRNA. In some embodiments, the cDNA molecule does not contain intron sequences present in an underlying genomic sequence from which the RNA molecule is transcribed. In some embodiments, the cDNA can span an intron/exon junction of a coding gene. cDNA can be generated via reverse transcription or any other technique and can be generated as a step in an assay described herein.

Biomarkers in the pathogenesis of diabetes and/or metabolic syndrome can be 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, and/or Y RNA-1.

A biomarker as specified herein can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. In some embodiments, a biomarker as specified herein can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

Assays Using the Capture Molecules

The capture molecules described herein can be used in an assay to detect and/or quantify an amount of one or more biomarkers present in a sample obtained from a subject. LncRNAs can be present within the cell as well as secreted within exosomes by the cell from which they are made. The biomarker can be present in a tissue, a cell, an exosome, a cell secretion, and/or a bodily fluid, body secretion or bodily excretion. The sample can be obtained from bodily fluid, body secretion or bodily excretion, tissue, organ, cell, an in vitro cell culture, conditioned media from an in vitro cell culture, cell secretion, and/or exosome preparation. The sample or component thereof can be obtained from subject having, predisposed to having, or suspected of having diabetes, metabolic syndrome, Alzheimer's disease, both Alzheimer's disease and diabetes (a.k.a Type 3 diabetes), or cancer. In other embodiments, the subject can be obese or aging. In some embodiments, the sample or component thereof can be obtained from a non-obese individual.

The assay can contain the steps of contacting a sample with a capture molecule that is configured to specifically bind to a biomarker and detecting the presence of specific binding of the biomarker by the capture molecule as compared to a control. The control can be a positive control, negative control, or an assay control. In some embodiments, the negative control can include a capture molecule that specifically binds to a molecule not involved in the pathogenesis of diabetes and/or metabolic syndrome. In some embodiments, the positive control can contain a capture molecule that specifically binds to a molecule known to be involved in the pathogenesis of diabetes and/or metabolic syndrome. In some embodiments, the negative control can include a sample obtained from a subject not having diabetes and/or metabolic syndrome. In some embodiments, the negative control can include a sample obtained from a subject not predisposed to diabetes and/or metabolic syndrome. In some embodiments, the positive control can include a sample from a subject known to have diabetes and/or metabolic syndrome. In other embodiments, the positive control can include a sample obtained from a subject known to be predisposed to diabetes and/or metabolic syndrome. In some embodiments, the positive control can be adipocytes over-expressing GAS5 (generated using techniques generally known in the art including, but not limited to, transfection of adipocytes with a GAS5 expression plasmid). In some embodiments, the negative control can be adipocytes having depleted GAS5 (generated using techniques generally known in the art including, but not limited to, transfection of GAS5 siRNA/shRNA/anti-sense oligonucleotide). The assay can be configured to aid in the diagnosis, treatment, management, or prognosis of diabetes and/or metabolic syndrome by the specific capture molecule or combination of capture molecules included in the assay.

The assay can also contain the step of processing the sample prior to contacting the sample with the capture molecule. In steps where the sample is further processed, a part of the further processed sample is contacted with the capture molecule as opposed to the entire unprocessed sample. The step of processing the sample can include processing the sample to obtaining a fraction of the sample that contains the biomarker and/or processing the sample (or fraction thereof) to isolate the type of molecules that include the biomarkers or interest.

Where the sample is a blood sample, processing the sample can include separating the blood sample into a plasma, buffy coat, and/or serum fractions by a suitable method. Suitable methods for processing blood samples are generally known in the art.

Where the sample is a tissue, organ, or cell, the tissue, organ, or cell can be further processed prior to contacting the sample with the capture molecule. The tissue, organ, or cell, can be fixed in a suitable fixing solution, embedded in a suitable material, or frozen prior to contacting the capture molecule with the sample. Suitable fixing solutions and embedding material can work preserve the integrity of the RNA and are generally known in the art. The fixed or frozen tissue, organ, or cell can be sectioned and/or attached to a suitable solid support. Suitable solid supports and methods of attachment are generally known in the art.

Following transcription in the nucleus, the lncRNAs are transported in the cytoplasm in small membrane vesicles of about 40-100 nm secreted by most cells in vivo and in vitro. The exosomes are the smallest vesicles with increasing sizes of microvesicles and multivesicular bodies. Exosomes can be found in bodily fluids, including, but not limited to blood, urine, ascite fluid. LncRNAs can be found within the exosomes. In some embodiments, processing the sample can include isolating the exosomes by a suitable method. Exosomes can be isolated directly from the sample or fraction thereof. Suitable methods for obtaining exosomes from a sample are generally known in the art The sample or processed sample can be further processed using any suitable chemical method, physical method, or combinations thereof to release, concentrate, separate and/or isolate the biomarker. In some embodiments, the step of isolating RNA from the sample can include isolating total RNA, mRNA, lncRNA, snRNA, miRNA, or any other particular species or combinations thereof of RNA by a suitable method. Suitable methods for isolating RNA species are generally known in the art.

In some embodiments, the assay also contains the step of making a complementary polynucleotide to one or more RNA molecules and/or one or more DNA molecules within the sample or separated component thereof. cDNA or cRNA can be generated by, for example, reverse-transcription of RNA or in vitro transcription of DNA, respectively.

The assay can also contain the step of quantifying or calculating an amount of a biomarker present in the sample and/or the step of quantifying an amount of biomarker that is specifically bound to a capture molecule. In some embodiments, the amount of biomarker present in the sample is quantified by quantifying the amount of biomarker that is specifically bound to a capture molecule. Specific binding of the biomarker and the capture molecule can result in a measurable, detectable, and/or quantifiable signal. Methods of quantifying the amount of biomarker specifically bound to a capture molecule based on the measurable, detectable, and/or quantifiable signal in a binding assay are generally known in the art.

In some embodiments, the step of detecting the presence of specific binding of the biomarker by the capture molecule and/or the step of detecting, measuring, and/or quantifying the amount of biomarker specifically bound by the capture molecule is performed, at least in part, using a method selected from an array (including microarrays), polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing (including but not limited to transcriptome sequencing and analysis and secretome sequence and analysis, RNASeq), cell-based RNA detection assays, in situ hybridization, northern blot analysis.

The amount of specifically bound biomarker quantified in some of the methods described herein can be an absolute amount of molecules of specifically bound biomarker to a capture molecule or a relative amount of specifically bound biomarker. An absolute amount can be calculated from a standard curve. The relative amount can be determined by normalizing the amount of specifically bound biomarker quantified to an internal standard or reference amount.

The amount of specifically bound biomarker can be about 0% to about 50% less than the control, 50% to 100% less than the control, about 100% to about 500% less than the control, or less than about 500% than the control. The amount of specifically bound biomarker can be about 0% to about 50% greater than the control, about 50% to about 100% greater than the control, about 100% to about 500% greater than the control, or greater than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measurable, detectable, and/or quantifiable signal in a binding assay are generally known in the art.

In further embodiments, the assay can contain the steps of contacting a sample or component thereof as described elsewhere herein with one ore more capture molecules and/or a plurality of capture molecules, where each capture molecule is configured to specifically bind to a biomarker that can be involved in the pathogenesis of diabetes and/or metabolic syndrome, and detecting the presence of specific binding of at least one biomarker by at least one of the capture molecules in the plurality of capture molecules. The biomarker(s) can be 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, and/or Y RNA-1.

A biomarker as specified herein can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. In some embodiments, a biomarker as specified herein can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

In some embodiments, the one or more biomarker(s) and/or plurality of capture molecule(s) can be configured to bind at least two lncRNAs (or corresponding cDNA) selected from 21A, anti-nos2a, hotair, neat1, malat 1, tug1, snhg6 and lincrna-ror. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

In other embodiments, the one or more biomarker(s) and/or plurality of capture molecule(s) can be configured to bind at least two of lncRNAs (or corresponding cDNA) selected from 7sL, dlg2as, gas5, hotairm1, lust, malat1, neat 1 and mar 3. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

In further embodiments, the one or more biomarker(s) and/or plurality of capture molecule(s) can be configured to bind at least two of lncRNAs (or corresponding cDNA) selected from 21A, 7sl, anti-nos2a, dlg2as, gas5, hotair, hotairm1, lust, malat 1, lincrna-ror, lncrna-vldr, lincrna-p21, saf, snhg6, neat 1 and tug 1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

In additional embodiments, the one or more biomarker(s) and/or plurality of capture molecule(s) can be configured to bind at least two lncRNAs (or corresponding cDNA) selected from anti-nos2a, hotair, hotairm1, gas5, and tug 1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

The one or more biomarker(s) and/or plurality of capture molecule(s) can be configured to bind at least two lncRNAs (or corresponding cDNA) selected from 21A, 7sl, anti-nos2a, gas5, hotair, hotairm1, lust, neat1, mcr3, incrna-ror, lincrna-vldr, lincrna-p21, saf, snhg6, and tug 1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

The one or more biomarker(s) and/or plurality of capture molecule(s) can be configured to bind at least two lncRNAs (or corresponding cDNA) selected from 21A, 7sl, anti-nos2a, gas5, lust, lincRNA-ror, and lincrna-vldr. The plurality of capture molecules can be configured to bind the lncRNA (or the cDNA) of hotair and hotairm1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

The one or more biomarker(s) and/or plurality of capture molecule(s) can be configured to bind at least two lncRNAs (or corresponding cDNA) selected from 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, and tug 1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

In other embodiments, the one or more biomarker(s) and/or plurality of capture molecule(s) can be configured to bind at least two biomarkers selected from RNA or cDNA of 21A, 7sl, anti-nos2a, dlg2as, gas5 (SNHG2), hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, and Y RNA-1. These biomarkers can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42. These biomarkers can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NOs: 9-42.

The assay can be configured such that each capture molecule or each capture molecule in the plurality of capture molecules is configured to each specifically bind to a different biomarker. In other embodiments, the assay can be configured such that at least two of the capture molecules specifically bind to a different biomarker. In further embodiments, the assay can be configured such that at least two of the capture molecules specifically bind to the same biomarker. In embodiments where the assay contains the step of contacting a sample or component thereof obtained from a subject with a capture molecule and/or the plurality of capture molecules, the assay can further contain any additional steps as described herein, including, but not limited to, quantifying the specific binding of one or more biomarkers by one or more capture molecules and processing the sample or component thereof.

Arrays and Fixed Capture Molecule Assays

Also described herein are arrays, including microarrays, and fixed capture molecule assays that can be used to detect one or more molecules of interest (e.g. biomarkers) present in a sample. In an array, one or more capture molecules are attached to or operatively linked to a support in essentially discrete locations on the support. The capture molecules can be as described elsewhere herein.

In arrays, discrete locations on the support where the capture molecule(s) can be attached to or operatively linked are individually referred to herein as a feature of the array and collectively as features. The features can be arranged in any desired arrangement on the support. The arrangement can be such that each feature has its own coordinate so as to allow identification of the capture molecule and/or biomarker detected at any given discrete location in the array according to the coordinate of the feature. These arrays can also be referred to as "ordered arrays". The features can be arranged on the support to be 0.01 nm to 1 cm apart from another feature on the support. A single feature can contain a single capture molecule (singleplex) or can contain more than one capture molecules (multiplex).

In other embodiments, the location of the feature on the support is not important and thus they can be random. These embodiments are referred to as fixed capture molecule assays. In these embodiments, detection can be made based on the knowledge of what feature(s), and some instances how many, are present on the support. For example, capture molecule(s) can be attached to substrate beads, that when a biomarker specifically binds to a capture molecule on the bead, a signal can be produced. The intensity of the signal and/or type of signal produced (e.g. wavelength) can indicate the biomarker bound and/or quantity.

The support can be solid or semi-solid. The support can be rigid or be flexible. The support can contain one or more specialized layers that affect the functionality or performance of the array. The support can be two-dimensional or three-dimensional. The support can be made of glass, such as silicon dioxide or borosilicate; plastic, such as polystyrene, nylon, polyvinylidene difluoride; a fibrous material, such as cellulose, carboxy methyl cellulose, or nitrocellulose; a gel, such as agarose, a hydrogel, or polyacrylamide. The support can be formed into any desired shape, including but not limited to a square, a rectangle, a circle, a cube, a rectangular prism, or other regular or irregular polygonal shape or its corresponding three-dimensional shape. The support can have a length, a width, a height, a radius, and/or a diameter. The length of the support can range from about 1 µm to about 10 cm. The height of the support can range from about 1 µm to about 10 cm. The width of the support can range from about 1 µm to about 10 cm. The radius of the support can range from about 1 µm to about 10 cm. The diameter of the support can range from about 1 µm to about 10 cm.

The support can contain a single layer to which the capture molecule is attached or operatively linked. In these embodiments, the support can also be referred to as the surface layer. In other embodiments, the support can contain more than one layer. In embodiments with more than one layer, the layer to which the capture molecule is attached or operatively linked is referred to as the surface layer. The surface layer can be modified to affect the interaction and/or reduce non-specific binding between a capture molecule and the support and/or the capture molecule and the biomarker. In some embodiments, surface layer is modified to enhance the interaction between the capture molecule and the surface layer and/or the interaction between the capture molecule and its corresponding biomarker. The modification of the surface layer can also reduce non-specific binding by the capture molecule and/or the biomarker.

In some embodiments, the surface layer is modified with a chemical modification. Suitable chemical modifications include, but are not limited to, reactive hydroxide groups, reactive primary, secondary, tertiary, and/or quaternary amine groups, a monolayer of a reactive antibody including but not limited to anti-glutathione S-transferase (anti-GST) antibodies, reactive epoxide groups, reactive methacrylate groups, aldehyde reactive groups, reactive NG proteins that bind immunoglobulins, and 3-D film coatings, which are polymeric coatings containing activated covalent binding sites. In some embodiments, 3-D film polymeric coatings include, but are not limited to, polysaccharides and hydrophilic polymers. In some embodiments, the 3-D film activated covalent binding sites include, but are not limited to, N-hydroxy succamide esters. The surface layer can be modified to be positively charged, neutral, or negatively charged. The surface layer can be modified to be hydrophilic, hydrophobic, or to contain a mix of hydrophobic and hydrophilic regions. In some embodiments, the modifications are patterned on the surface layer to form discrete functionalized areas to which the capture molecule is attached or operatively-linked. In some embodiments having mixed hydrophobic and hydrophilic regions, the hydrophilic regions are separated by hydrophobic regions. In other embodiments, having mixed hydrophobic and hydrophilic regions, the hydrophobic regions are separated by hydrophilic regions.

In some embodiments, the surface layer is a gel, including but not limited to agarose, a hydrogel, or polyacrylamide. In some embodiments the support contains multiple discrete gel surface layers. These gel surface layers are also referred to as pads and can be arranged on the support in an ordered arrangement such that each gel pad is a feature of the array. In some embodiments, the same capture molecule(s) are attached to or operatively linked to all the gel pads forming the surface layer of the support. In other embodiments, at least two of the gel pads have at least one different capture molecule attached or operatively linked thereto.

The support can be configured to have one or more three dimensional discrete indentations or depressions in the surface layer. The capture molecule(s) can be attached or operatively linked to the indentation. The three dimensional indentions can be square, rectangular, round, or irregular shaped. The three dimensional indentations can form wells or channels. One or more indentations can be connected to another indentation by a three dimensional connector channel extending between the one or more wells. In some embodiments, the connector channel is a microfluidic channel. In some embodiments, the microfluidic channel contains wicking paper. A dimension of the indentation can range from about 1 µm to about 10 cm. In some embodiments, a length of an indentation ranges from about 1 µm to about 10 cm. In further embodiments, a width of an indentation can range from about 1 µm to about 10 cm. In additional embodiments, a height of an indentation can range from about 1 µm to about 10 cm. In other embodiments, the radius of an indentation can range from about 1 µm to about 10 cm. In further embodiments, the diameter of an indentation can range from about 1 µm to about 10 cm. The indentations can be so dimensioned so as to hold a specific volume. In some embodiments, the specific volume ranges from about 1 nL to about 1,000 mL. In a single array, the indentations can all be about the same dimension. In other embodiments, at least two of the indentations differ in at least one dimension. Any surface of an indentation can be modified as described above with respect to modification of the surface layer.

The support can also contain additional layers beneath the surface layer and within the support. The additional layers can be directly beneath the surface layer or contain other layers, such as the support, between the additional layer and the surface layer. The additional layer can improve the signal to noise ratio, affect signal production produced by the binding of a capture molecule to a biomarker or other substrate, and affect other properties or performance parameters of the array. In some embodiments the additional layer is a dielectric layer. The dielectric layer can improve the reflection of the signal produced upon binding of a capture molecule and a biomarker.

In some embodiments, the array can be a tissue microarray, which refers to a block of paraffin or other tissue embedding material that contains at least two tissue samples, where the tissue samples are positioned at discrete locations and arranged in a known order. The tissue samples can be core biopsies. The block can then be sliced and a slice of this block can be attached to or operatively linked to a suitable solid support. Suitable solid supports are described elsewhere herein. The block or slice thereof can then be contacted with a capture molecule and specific binding of a biomarker and the capture molecule can be detected. In some embodiments, more than one slices of the block are attached or operatively linked to the solid support.

In some embodiments, the support having one or more capture molecules attached or operatively linked can be incorporated and/or disposed upon the surface of a device, including without limitation, within a well, chamber, or piezoelectric element, and/or microfluidic channel of a microfluidic or other device.

Methods of Diagnosing and Prognosing Diabetes and/or Metabolic Syndrome

Also described herein are methods of diagnosing and/or prognosing diabetes, metabolic syndrome, a pre-diabetic state, and/or early onset of diabetes a subject. The methods can also determine the effect of treatment or management on the state of or development of diabetes and/or metabolic syndrome. The methods of diagnosing and/or prognosing diabetes, metabolic syndrome, a pre-diabetic state, and/or early onset of diabetes in a subject can be performed using one or more of the capture molecules, assays, kits, and arrays described herein.

Some methods of diagnosing and/or prognosing diabetes, metabolic syndrome, a pre-diabetic state, and/or early onset of diabetes in a subject can include the steps of contacting a sample with a capture molecule configured to bind a biomarker as described herein, detecting the presence or absence of the specific binding of the biomarker by the capture molecule, and diagnosing diabetes, a pre-diabetic state, and/or early onset of diabetes when the presence or absence of specific binding of the biomarker by the capture molecule is detected as compared to a control. In some embodiments, gas5 RNA (or corresponding cDNA) can be detected in the sample. In other embodiments, the RNA (or corresponding cDNA) of 21A, 7sl, anti-nos2a, dlg2as, hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y, RNA-1, and/or combinations thereof can be detected.

Further methods of diagnosing and/or prognosing diabetes, metabolic syndrome, a pre-diabetic state, and/or early onset of diabetes can include the steps of contacting a sample or component thereof with a capture molecule configured to specifically bind a biomarker as described herein, detecting the presence or absence of specific binding of the biomarker by the capture molecule, quantifying an amount of biomarker specifically bound by the capture molecule, and diagnosing and/or prognosing a subject with diabetes, metabolic syndrome, a pre-diabetic state, and/or early onset of diabetes when the amount of specifically bound biomarker is greater than the amount of specifically bound biomarker in a control. In some embodiments, a diagnosis and/or prognosis of diabetes metabolic syndrome, a pre-diabetic state, and/or early onset of diabetes can be made when the amount of specifically bound gas 5 (snhg2), 21A, anti-nos2a, hotair, neat1, lincrna-ror, 7sl, and/or lincrna-vldr RNA (or corresponding cDNA) is greater than the amount of specifically bound gas 5 (snhg2), 21A, anti-nos2a, hotair, neat1, lincrna-ror, 7sl, and/or lincrna-vldr RNA (or corresponding cDNA) in the control. In further embodiments, a diagnosis and/or prognosis of diabetes metabolic syndrome, a pre-diabetic state, and/or early onset of diabetes can b made when the amount of specifically bound gas 5 (snhg2), 21A, anti-nos2a, hotair, neat1, lincrna-ror, 7sl, and/or lincrna-vldr RNA (or corresponding cDNA) is greater than a standard and/or predetermined threshold.

Additional methods of diagnosing and/or prognosing diabetes, metabolic syndrome, a pre-diabetic state, and/or early onset of diabetes can include the steps of contacting a sample or component thereof with a capture molecule configured to specifically bind a biomarker as described herein, detecting the presence or absence of specific binding of the biomarker by the capture molecule, quantifying an amount of biomarker specifically bound by the capture molecule, and diagnosing and/or prognosing a subject with diabetes, metabolic syndrome, a pre-diabetic state, and/or early onset of diabetes when the amount of specifically bound biomarker is less than the amount of specifically bound biomarker in a control. In some embodiments, a diagnosis and/or prognosis of diabetes metabolic syndrome, a pre-diabetic state, and/or early onset of diabetes can be made when the amount of specifically bound 7sl, dlg2as, gas 5 (SNHG2), hotairm1, lust, malat 1, mcr3, lincrna-vldr, lincrna-p21, saf, snhg6, sox2ot, and/or tug 1 is less than the amount of 7sl, dlg2as, gas 5 (SNHG2), hotairm1, lust, malat 1, mcr3, lincrna-vldr, lincrna-p21, saf, snhg6, sox2ot, and/or tug 1 specifically bound in the control. In some embodiments, a diagnosis and/or prognosis of diabetes metabolic syndrome, a pre-diabetic state, and/or early onset of diabetes is made when the amount of specifically bound 7sl, dlg2as, gas 5 (SNHG2), hotairm1, lust, malat 1, mcr3, lincrna-vldr, lincrna-p21, saf, snhg6, sox2ot, and/or tug 1 is less than a standard and/or predetermined threshold.

Other methods of diagnosing and/or prognosing diabetes, metabolic syndrome, a pre-diabetic state, and/or early onset of diabetes can include the steps contacting a sample obtained from a subject with a plurality of capture molecules, where each capture molecule is configured to specifically bind to one or more biomarkers, detecting the presence or absence of specific binding of at least one biomarker by at least one of the capture molecules in the plurality of capture molecules, and diagnosing and/or prognosing diabetes, metabolic syndrome, a pre-diabetic state, and/or early onset of diabetes when the presence or absence of at least one biomarker specifically bound by a capture molecule of the plurality of capture molecules is detected as compared to a control. In other embodiments, diagnosing and/or prognosing diabetes, metabolic syndrome, a pre-diabetic state, and/or early onset of diabetes can occur when the presence or absence of at least two, three, or four biomarkers specifically bound by at least two, three, four, respectively, of the capture molecules of the plurality of capture molecules is detected as compared to the control. The plurality of capture molecules in the method can be configured such that the presence of absence of specific binding of gas5, 21A, 7sl, anti-nos2a, dlg2as, hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y, RNA-1, and/or combinations thereof to the plurality of capture molecules can be detected.

Further methods of diagnosing and/or prognosing diabetes, metabolic syndrome, a pre-diabetic state, and/or early onset of diabetes can include the steps contacting a sample obtained from a subject with plurality of capture molecules, where each capture molecule is configured to specifically bind to a biomarker, detecting the presence or absence of specific binding of at least one biomarker by at least one of the capture molecules in the plurality of capture molecules, quantifying an amount of a biomarker that is specifically bound by a capture molecule in the plurality of capture molecules, and diagnosing and/or prognosing diabetes, metabolic syndrome, a pre-diabetic state, and/or early onset of diabetes when the amount of at least one biomarker specifically bound by a capture molecule of the plurality of capture molecules is greater than the amount of at least one biomarker specifically bound by the capture molecule in a control, standard, and/or predetermined threshold value. In some embodiments, a diagnosis and/or prognosis of diabetes, metabolic syndrome, a pre-diabetic state, and/or early onset of diabetes can be made when the amount of 21A, anti-nos2a, hotair, neat1, lincrna-ror, 7sl, lincrna-vldr RNA (or corresponding cDNA), or combinations thereof is greater than the amount of specifically bound 21A, anti-nos2a, hotair, neat1, lincrna-ror, 7sl, lincrna-vldr RNA (or corresponding cDNA), or combinations thereof in a control, standard, and/or predetermined threshold value.

Further methods of diagnosing and/or prognosing diabetes, metabolic syndrome, a pre-diabetic state, and/or early onset of diabetes can include the steps contacting a sample obtained from a subject with plurality of capture molecules, where each capture molecule is configured to specifically bind to a biomarker, detecting the presence or absence of specific binding of at least one biomarker by at least one of the capture molecules in the plurality of capture molecules, quantifying an amount of a biomarker that is specifically bound by a capture molecule in the plurality of capture molecules, and diagnosing and/or prognosing diabetes, metabolic syndrome, a pre-diabetic state, and/or early onset of diabetes when the amount of at least one biomarker specifically bound by a capture molecule of the plurality of capture molecules is less than the amount of at least one biomarker specifically bound by the capture molecule in a control, standard, and/or predetermined threshold value. In some embodiments, a diagnosis and/or prognosis of diabetes, metabolic syndrome, a pre-diabetic state, and/or early onset of diabetes is made when the amount of 7sl, dlg2as, gas 5 (SNHG2), hotairm1, lust, malat 1, mcr3, lincrna-vldr, lincrna-p21, saf, snhg6, sox2ot, tug 1 RNA (or corresponding cDNA), or combinations thereof is less than the amount of 7sl, dlg2as, gas 5 (SNHG2), hotairm1, lust, malat 1, mcr3, lincrna-vldr, lincrna-p21, saf, snhg6, sox2ot, and/or tug 1 RNA (or corresponding cDNA), or combinations thereof in a control, standard, and/or predetermined threshold value.

Additional methods of diagnosing and/or prognosing diabetes, metabolic syndrome, a pre-diabetic state, and/or early onset of diabetes can include the steps contacting a sample obtained from a subject with a plurality of capture molecules, where each capture molecule is configured to specifically bind to a biomarker, detecting the presence or absence of specific binding of at least two, three, four, or more biomarkers by at least two, three, four, or more respectively, of the capture molecules in the plurality of capture molecules as compared to a control, and diagnosing and/or prognosing diabetes, metabolic syndrome, a pre-diabetic state, and/or early onset of diabetes when the presence or absence of specific binding of at least two, three, four, or more biomarkers to at least two, three, four, or more of the capture molecules of the plurality of capture molecules is detected as compared to a control. Each capture molecule in the at least two, three, four, or more capture molecules in the plurality of capture molecules can be configured to specifically bind an RNA or cDNA corresponding to any one of the following: gas5, 21A, 7sl, anti-nos2a, dlg2as, hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y, and RNA-1.

Further methods of diagnosing and/or prognosing diabetes, metabolic syndrome, a pre-diabetic state, and/or early onset of diabetes can include the steps contacting a sample obtained from a subject with a plurality of capture molecules, where each capture molecule in the plurality of capture molecules is configured to specifically bind to a biomarker, detecting the presence or absence of specific binding of at least two, three, four, or more biomarkers by at least two, three, four, or more, of the capture molecules in the plurality of capture molecules, quantifying an amount of specifically bound biomarkers to each of the two, three, four, or more capture molecules, and diagnosing and/or prognosing diabetes, metabolic syndrome, a pre-diabetic state, and/or early onset of diabetes if an amount of at least one, two, three, four, or more specifically bound biomarkers is greater than a control, standard, and/or predetermined threshold value. The biomarkers can be selected from 21A, anti-nos2a, hotair, neat1, lincrna-ror, 7sl, lincrna-vldr RNA (or corresponding cDNA). In some embodiments, a diagnosis and/or prognosis of diabetes, metabolic syndrome, a pre-diabetic state, and/or early onset of diabetes can be made when the amount 21A, anti-nos2a, hotair, neat1, lincrna-ror, 7sl, lincrna-vldr RNA (or corresponding cDNA), or combinations thereof is greater than the amount of specifically bound 21A, anti-nos2a, hotair, neat1, lincrna-ror, 7sl, lincrna-vldr RNA (or corresponding cDNA), or combinations thereof in a control, standard, and/or predetermined threshold value.

Further methods of diagnosing and/or prognosing diabetes, metabolic syndrome, a pre-diabetic state, and/or early onset of diabetes can include the steps contacting a sample obtained from a subject with a plurality of capture molecules, where each capture molecule is configured to specifically bind to a biomarker, detecting the presence or absence of specific binding of at least two, three, four, or more biomarkers by at least two, three, four, or more, of the capture molecules in the plurality of capture molecules, quantifying an amount of specifically bound biomarkers to each of the two, three, four, or more capture molecules in the plurality of capture molecules, and diagnosing and/or prognosing diabetes, metabolic syndrome, a pre-diabetic state, and/or early onset of diabetes if an amount of at least one, two, three, four, or more specifically bound biomarkers is less than a control, standard, and/or predetermined threshold value. The biomarkers can be 7sl, dlg2as, gas 5 (SNHG2), hotairm1, lust, malat 1, mcr3, lincrna-vldr, lincrna-p21, saf, snhg6, sox2ot, tug 1. In some embodiments, a diagnosis and/or prognosis of diabetes, metabolic syndrome, a pre-diabetic state, and/or early onset of diabetes can be made when the amount of 7sl, dlg2as, gas 5 (SNHG2), hotairm1, lust, malat 1, mcr3, lincrna-vldr, lincrna-p21, saf, snhg6, sox2ot, tug 1 RNA (or corresponding cDNA), or combinations thereof is less than the amount of 7sl, dlg2as, gas 5 (SNHG2), hotairm1, lust, malat 1, mcr3, lincrna-vldr, lincrna-p21, saf, snhg6, sox2ot, and/or tug 1 RNA (or corresponding cDNA), or combinations thereof in a control, standard, and/or predetermined threshold value.

Further methods of diagnosing and/or prognosing diabetes, metabolic syndrome, a pre-diabetic state, and/or early onset of diabetes can include the steps contacting a sample obtained from a subject with a plurality of capture molecules, where each capture molecule is configured to specifically bind to a biomarker, detecting the presence or absence of specific binding of at least two, three, four, or more biomarkers by at least two, three, four, or more, of the capture molecules in the plurality of capture molecules, quantifying an amount of specifically bound biomarkers to each of the two, three, four, or more capture molecules in the plurality of capture molecules, and diagnosing and/or prognosing diabetes, metabolic syndrome, a pre-diabetic state, and/or early onset of diabetes when an amount of at least one specifically bound biomarkers is greater than a control, standard, and/or predetermined threshold value and/or when an amount of at least one specifically bound biomarker is less than a control, standard, and/or predetermined threshold value. The specifically bound biomarker that is greater than the control can be 21A, anti-nos2a, hotair, neat1, lincrna-ror, 7sl, or lincrna-vldr RNA (or corresponding cDNA). The specifically bound biomarker that is less than the control can be 7sl, dlg2as, gas 5 (SNHG2), hotairm1, lust, malat 1, mcr3, lincrna-vldr, lincrna-p21, saf, snhg6, sox2ot, tug 1 RNA (or corresponding cDNA).

The amount of specifically bound biomarker quantified in some of the methods described herein can be an absolute amount of molecules of specifically bound biomarker to a capture molecule or a relative amount of specifically bound biomarker. An absolute amount can be calculated from a standard curve. The relative amount can be determined by normalizing the amount of specifically bound biomarker quantified to an internal standard, reference amount, and/or amount of another biomarker in the same or different sample.

The amount of specifically bound biomarker can be about 0% to about 50% less than the control, 50% to 100% less than the control, about 100% to about 500% less than the control, or less than about 500% than the control. The amount of specifically bound biomarker can be about 0% to about 50% greater than the control, about 50% to about 100% greater than the control, about 100% to about 500% greater than the control, or greater than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measurable, detectable, and/or quantifiable signal in a binding assay are generally known in the art.

The sample can be obtained from bodily fluid, bodily secretion, bodily excretion, tissue, organ, cell, an in vitro cell culture, conditioned media from an in vitro cell culture, cell secretion, and/or exosome preparation. The sample or component thereof can be obtained from subject having, predisposed to having, or suspected of having diabetes, metabolic syndrome, Alzheimer's disease, both Alzheimer's disease and diabetes (a.k.a Type 3 diabetes), or cancer. In other embodiments, the subject can be obese or aging.

The control can be a positive control, negative control, or an assay control. In some embodiments, the negative control can include a capture molecule that specifically binds to a molecule not involved in the pathogenesis of diabetes and/or metabolic syndrome. In some embodiments, the positive control can contain a capture molecule that specifically binds to a molecule known to be involved in the pathogenesis of diabetes and/or metabolic syndrome. In some embodiments, the negative control can include a sample obtained from a subject not having diabetes and/or metabolic syndrome. In some embodiments, the negative control can include a sample obtained from a subject not predisposed to diabetes and/or metabolic syndrome. In some embodiments, the positive control can include a sample from a subject known to have diabetes and/or metabolic syndrome. In other embodiments, the positive control can include a sample obtained from a subject known to be predisposed to diabetes and/or metabolic syndrome. In some embodiments, the positive control can be adipocytes over-expressing GAS5 (generated using techniques generally known in the art including, but not limited to, transfection of adipocytes with a GAS5 expression plasmid). In some embodiments, the negative control can be adipocytes having depleted GAS5 (generated using techniques generally known in the art including, but not limited to, transfection of GAS5 siRNA/shRNA/anti-sense oligonucleotide).

Kits

Also described herein are kits containing one or more capture molecules described herein. In some embodiments, the kit can contain one or more antibodies or fragments thereof configured to specifically bind a biomarker described herein. The kit can contain one or more capture molecules configured to specifically bind one or more biomarkers described herein. In some embodiments, the kit can contain a capture molecule configured to bind to at least one of the following biomarkers: gas5, 21A, 7sl, anti-nos2a, dlg2as, hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y, RNA-1, and/or combinations thereof. In some embodiments, the one or more capture molecules can be polynucleotides. The kit can contain an array, where one ore more capture molecules are operatively coupled to a surface of the array. The array in the kit can contain one or more capture molecules configured to bind at least one of the following biomarkers: gas5, 21A, 7sl, anti-nos2a, dlg2as, hotair, htairm1, lust, malat 1, neat 1, mcr3, lincrna-ror, lincrna-vldr, lincrna-p21, saf, snhg6, sox2ot, tug 1, 7SK, BC200, EgoA, EGOB, H19 upstream conserved 1 & 2, HAR1A, HAR1Bm Hoxa11as, HoxA6as, IGF2AS, nC-uPARm NDM29, Nespas, NTT, SNHG3, SNHG4, Tsix, Y, RNA-1, and/or combinations thereof.

The kit can also contain a reagent for performing an array (including microarrays), polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing (including but not limited to transcriptome sequencing and analysis and secretome sequence and analysis, RNASeq), cell-based RNA detection assays, in situ hybridization, northern blot analysis, mass spectrometry, or combinations thereof. The kit can contain instructions fixed in a tangible medium of expression where the instructions provide for diagnosing and/or prognosing diabetes, metabolic syndrome, a pre-diabetic state, and/or early onset of diabetes.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Detection of Gas5 lncRNA in Bodily Fluids

Methods

Study population: Informed consent was obtained from veterans receiving care at James A Haley Veterans Hospital, Tampa, Fla. under IRB approved study (# Pro00012108). Serum samples are stored in the research bio-specimen repository (RBR). The de-identified and coded samples were provided to the PI along with research parameters such as age, gender, BMI (calculated as weight in kilograms/height in meter), diabetic (determined as glucose levels >125 mg/dL; HbA1c>6.5%) or non-diabetic (determined as glucose levels <125 mg/dL; HbA1c<6.4%). To achieve statistical significance, serum samples from Caucasian male volunteers were used as they formed the predominant population volunteering their serum samples at the JAHVH at the time of initiation of this study. In addition, patients diagnosed with any form of cancer were not part of the study group. For this study, 96 serum samples were analyzed (see Table 1).

Quantitative Real-Time RT-PCR:

Total RNA was isolated from serum samples from diabetic or non-diabetic subjects using Trizol LS according to the manufacturers protocol (Ambion). For the array, cDNA was prepared from 1.5 µg total RNA using LncRNA Profiler array kit (System Biosciences, cat # RA900A-1) according to manufacturers instructions. Amplification was performed with 2× Maxima SYBR Green Master with ROX (Thermo Scientific) and data were analyzed using System Biosciences software to generate ΔΔCt values and calculate fold change. U6 snRNA was used as control to normalize calculations.

For GAS5 real time qPCR, 2 µg RNA was reverse-transcribed using Qiagen's RT kit. 2 µL of cDNA was amplified by real-time quantitative PCR using Syber (SYBR) Green on the ViiaA 7 system (Applied Biosystems) to quantify the absolute levels of the transcripts in the samples.

GAPDH was used as the endogenous control. The primers used are: GAS5 sense primer 5'-AGCTGGAAGTT-GAAATGG-3' (SEQ ID NO: 1) and anti-sense 5' CAAGC-CGACTCTCCATACC-3' (SEQ ID NO: 2); GAPDH sense primer 5'-TGACGTGCCGCCTGGAGAAAC-3' (SEQ ID NO: 3) and anti-sense 5'-CCGGCATCGAAGGTG-GAAGAG-3' (SEQ ID NO: 4). These primers were initially tested using cDNA and conditioned media from human preadipocytes in a RT-PCR reaction using Taq polymerase to give distinct products corresponding to the respective transcripts. Next, the optimal primer concentration was determined from a range of 50-900 nM for forward and reverse primers. The final concentration of 600/600 nM was selected to ensure efficiency and specificity for its target based on the dissociation curve that showed a single, sharp peak, indicating that the primers amplify one specific target. For absolute quantification, a standard curve was generated for each gene in every assay. To do so, 100-0.4 ng of GAS5 plasmid was used to obtain a standard curve correlating the amounts with the threshold cycle number (Ct values). A linear relationship ($r^2>0.96$) was obtained for GAS5 and GAPDH. Real-time PCR was then performed on samples and standards in triplicate. The plate setup also included a standard series, no template control, no RNA control, no reverse transcriptase control, and no amplification control. The dissociation curve was analyzed for each sample. Absolute quantification of GAS5 expression levels for individual samples was calculated by normalizing the values to GAPDH. The results were analyzed as described below. A level of $P<0.05$ was considered statistically significant. Significance was determined after three or more experiments.

Statistical Analysis:

Statistical analyses including sensitivity, specificity, positive predictive value, negative predictive value, likelihood ratios and area under the receiver operating curve analysis were performed using Stata, version 13.1 {*Stata Statistical Software: Release* 13. College Station, Tex.: StataCorp LP). The optimal cutoff point was calculated using the Cutoff Finder (Budczies J, et al., PloS one. 2012; 7(12):e51862. doi: 10.1371/journal.pone.0051862. PubMed PMID: 23251644; PubMed Central PMCID: PMC3522617).

Results

Expression of GAS5 lncRNA in Serum:

For phase I of the study serum from five diabetic and non-diabetic subjects was screened for their long noncoding RNA (lncRNA) profiles. Total RNA was isolated and profiles of long non-coding RNAs were evaluated. To do so, human LncProfiler (S ABiosciences) array containing 84 lncRNAs with rigorous controls was used. We observed H19, HOTAIR, GAS5, ncR-uPAR, EGOb, antiPEGII and lincRNA-21 expression in serum from these patients. Other lncRNAs on the array were undetected for Ct analysis. Amongst the detected lncRNAs in the array, a marked decrease in GAS 5 expression in diabetic samples compared to non-diabetic was observed (FIG. 1). These results showed that lncRNA GAS5 was present in circulation in serum and its levels were significantly lower ($P<0.0001$ using unpaired t-test, PRISM™ software) in diabetic patients compared to non-diabetic samples.

Analysis of Serum Samples:

Next, circulating GAS5 levels in serum from non-diabetic and diabetic patients was evaluated. Ninety six serum samples were obtained from Research Bio-specimen Repository (RBR) at the James A. Haley Veterans' Hospital. Male Caucasian patients were selected from the volunteer serum sample pool. Table 1 shows demographics of the patients (IRB approved protocol # Pro00012108). The prevalence of DM was 49% (95% CI: 39%, 59.4%).

Figure 2A:
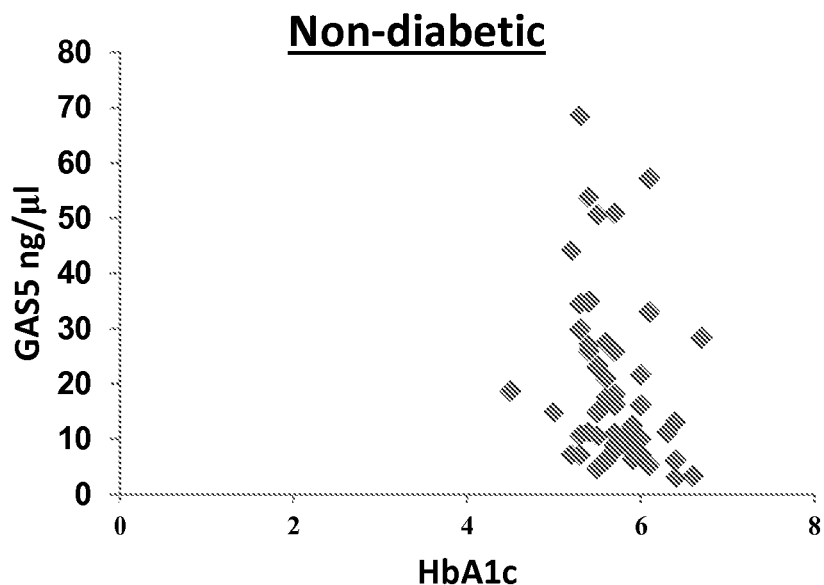
FIGS. 2A-2B shows graphs demonstrating serum GAS5 levels (ng/µL) versus HbA1c levels in non-diabetic (FIG. 2A) and diabetic (FIG. 2B) patients.
Figure 2B:
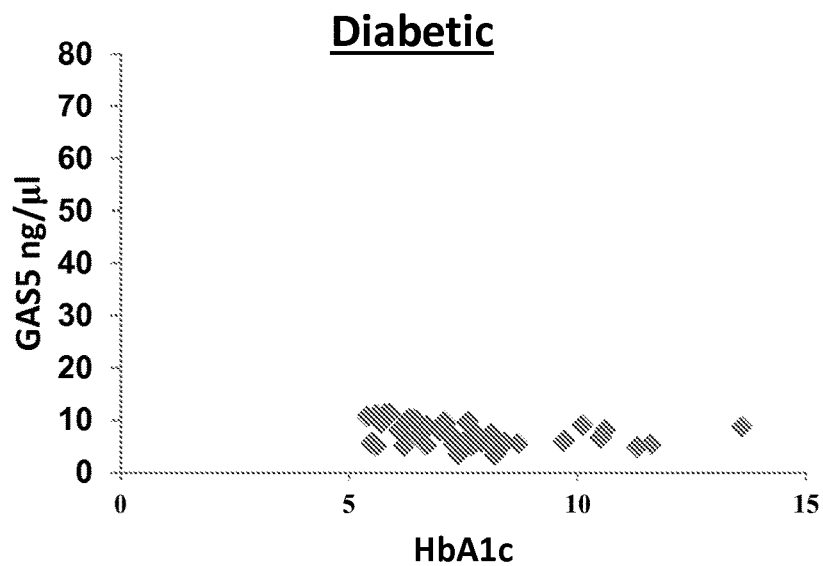

RNA was isolated and SYBR Green quantitative PCR in triplicate was used to obtain absolute GAS5 levels. GAS5 levels were observed to be significantly decreased in diabetic samples. GAS5 levels were decreased in patients with HbA1c>5.9 though these patients were not diagnosed as diabetic (cutoff HbA1c>6.5) in the clinic (FIGS. 2A-2B).

TABLE 1

|  | Non Diabetic (n = 49) | Diabetic (n = 47) | P-value |
|---|---|---|---|
| BMI | 29.4 ± 6.6 | 34.8 ± 7.0 | <0.001 |
| Age | 66.9 ± 9.7 | 70.3 ± 9.1 | 0.09 |
| Blood Glucose | 102.8 ± 16.3 | 163.6 ± 61.3 | <0.001 |

Figure 3:
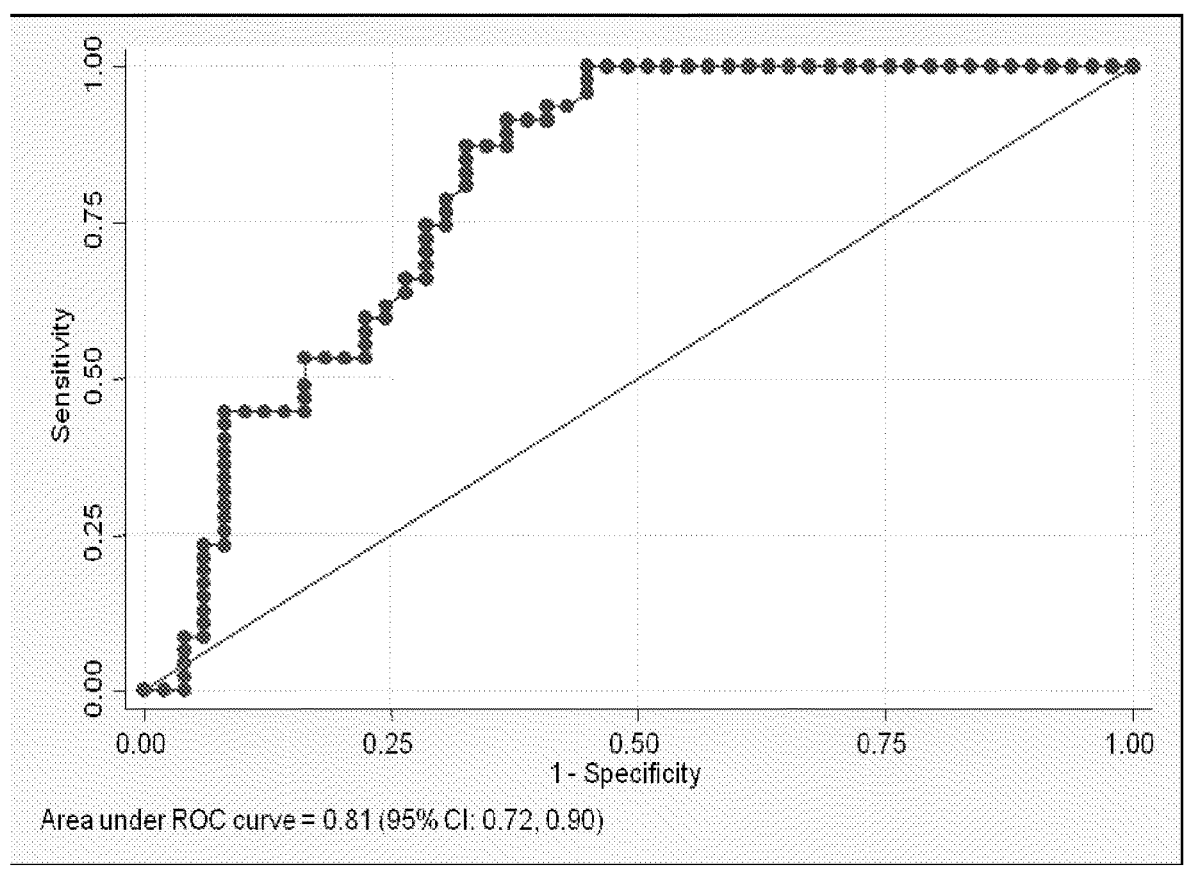
FIG. 3 shows a graph demonstrating the receiver operating characteristic (ROC) curve (demonstrating sensitivity and specificity of GAS5) for GAS 5 in the serum samples from subjects.

A receiver operating characteristic (ROC) curve was generated for statistical analysis of GAS5 levels in these 96 samples. ROC is widely used to investigate a reasonable cutoff level of the target. The ROC curve displays the relationship of sensitivity and specificity for GAS5. ROC analysis of GAS5 revealed the area under curve (AUC) of 0.81 (95% Confidence Interval (CI): 0.72, 0.90) (FIG. 3). The optimal cutoff GAS5 was less than or equal to 10 ng/ul measured as absolute quantification by qPCR, and this value had the sensitivity of 85.1% (95% CI: 72.3%, 92.6%), specificity of 67.3% (95% CI: 53.4%, 78.8%), positive predictive value (PPV) of 71.4% (95% CI: 57.8%, 82.7%), negative predictive value of 82.5% (95% CI: 67.2%, 92.7%), positive likelihood ratio test 2.61 (95% CI: 1.71, 3.96) and negative likelihood ratio test 0.22 (95% CI: 0.11, 0.45).

Figure 4:
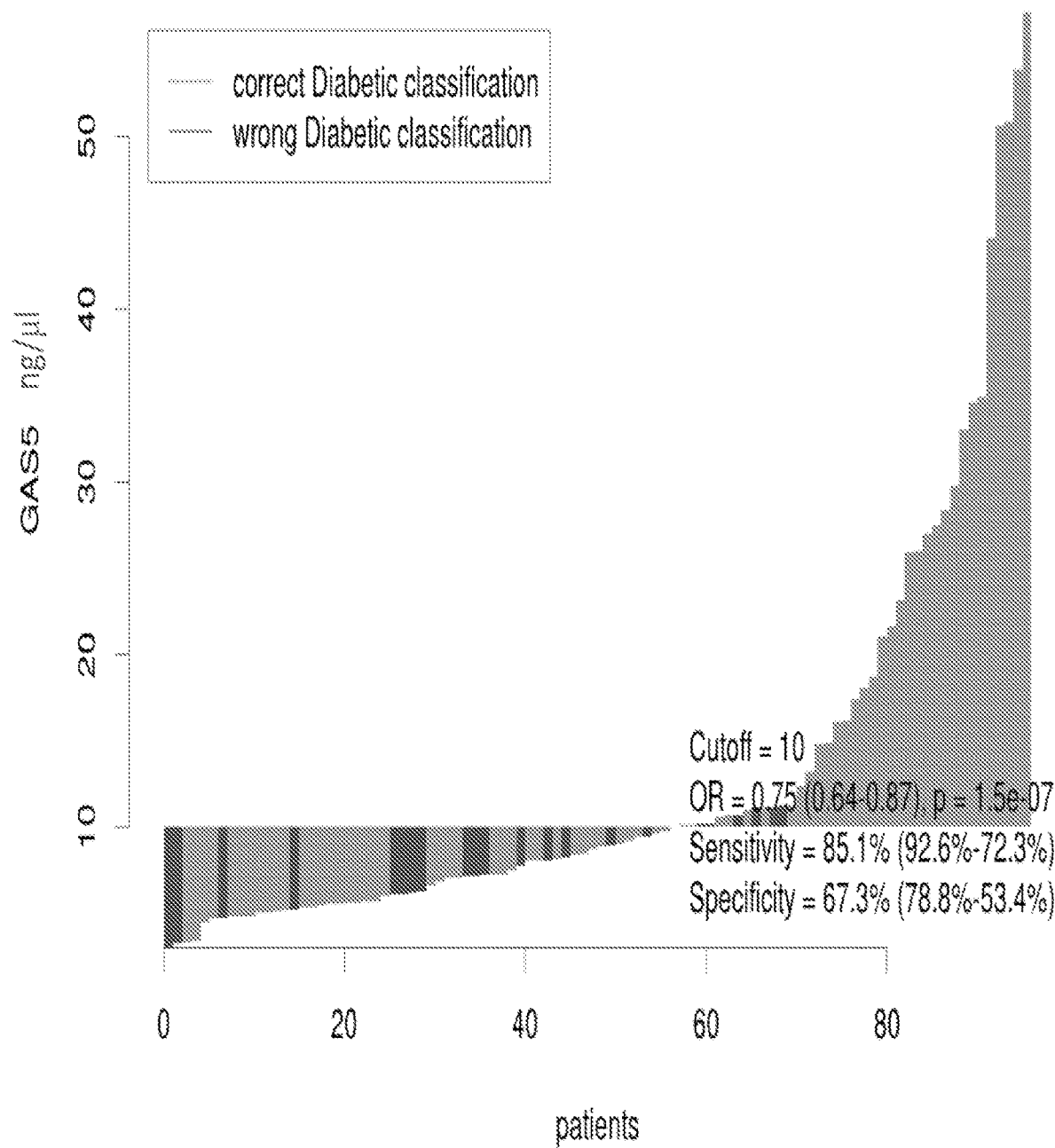
FIG. 4 shows a waterfall plot demonstrating classification accuracy of a cutoff point of about 10 ng/µL and the overall odds ratio for GAS5 as a predictor for diabetes.

These results suggest that individuals with absolute GAS5<10 have nearly twelve times the odds of having diabetes (Odds Ratio [OR]=11.79 (95% CI: 3.97, 37.26), p<0.001). In the clinic, individuals were classified as diabetic or non-diabetic based on their fasting glucose or HbA1c levels. The waterfall plot (FIG. 4) demonstrates the classification accuracy of the optimal cutoff point for all 96 patients, as well as the overall odds ratio for GAS5 as a predictor of diabetes (OR=0.75 (95% CI: 0.64, 0.87), p<0.001). When adjusted for patient BMI, age and blood glucose, the OR for GAS5 remained significant (OR=0.80 (95% CI: 0.65-0.97; p=0.025)). The results suggest that GAS5 levels are indicative and/or are a predictor of diabetes. Further these results suggest that GAS5 levels are indicative and/or are a predictor of diabetes regardless of the age, fasting blood glucose level, and/or BMI, of a subject.

Example 2: Gene Expression Profile of Adipocytes in NDM Lean and NDM Obese Individuals Methods:

The gene expression profiles of adipocytes obtained from non-diabetic lean and non-diabetic obese Pima Indian subjects were examined to identify differentially expressed adipocyte genes correlated with obesity. Gene expression profiles were obtained from the GEO database. Gene expression profiles in the GEO database were obtained using microarray analysis. Briefly, RNA samples of isolated abdominal subcutaneous adipocytes from 20 lean (10 Males/10 Females, aged 31±6 year, Body Mass Index 25±3 kg/m$^2$) and 19 obese (9M/10F, 29±5y, 55±8 kg/m$^2$) subjects were hybridized individually to Affymetrix oligonucleotide arrays HG-U95A, B, C, D, and E. Lee et al., Diabetologia 2005 September; 48(9):177-83.

To identify differentially expressed adipocyte genes correlated with obesity, LncProfiler (SABiosciences) was used to evaluate the expression of lncRNAs in subcutaneous adipose tissue from lean and obese patients (IRB #108360; obese BMI 43.7 to 44.3; lean BMI 22.1 to 22.8, nonsmokers, other criteria matched). Gas5 microarray results were validated by qPCR, as previously described in Example 1.

Figure 5:
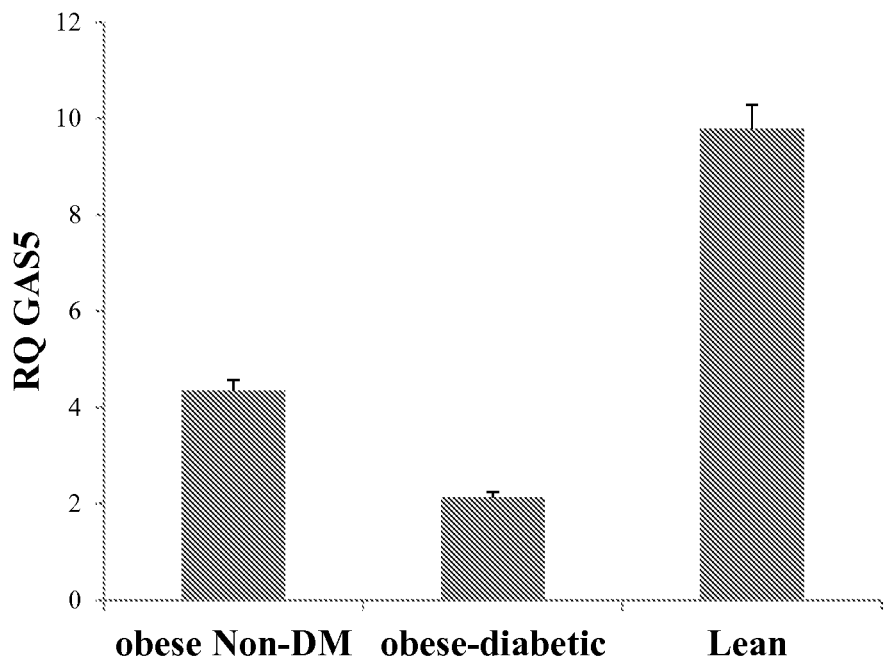
FIG. 5 shows a graph demonstrating the expression of Gas5, as measured by RT-qPCR, in subcutaneous adipocytes obtained from obese non-diabetic, obese diabetic, and lean patients.

Results:

As shown in FIG. 5, the data demonstrated a decrease in Gas5 expression in diabetic (both lean and obese) patients. Data also demonstrated that diabetic obese patients had a larger decrease in Gas5 expression as compared to non-diabetic obese patients. This indicates that obesity may also cause a decline in GAS5 levels and obese patients with a decrease in GAS5 levels have greater susceptibility towards diabetes and metabolic syndrome.

Example 3: Gas5 lncRNA Levels are Decreased in the Adipose Tissue and Adipose Secretome of Diabetics Methods:

LncRNAs are secreted by cells and can be detected in serum. In vitro, the secretome was measured in the conditioned media of adipocytes. Expression of Gas5 was examined in subcutaneous adipose tissue from normal lean and lean diabetic patients. Lean patients had a Body Mass Index (BMI) of 22.1±2. Non-diabetic patients had an HbA1c of less than about 5. Diabetic patients had an HbA1c of greater than about 6.5. All samples were obtained from non-smokers. Other criteria between lean normal and lean diabetics were matched.

Subcutaneous adipose tissue was obtained from the patients and digested with collagenase and purified to obtain adipocytes (free from other cells and macrophages). Adipocytes were maintained in culture for about 48 hours and conditioned media was collected. Real-time qPCR for Gas5 was performed and data was analyzed similarly to the procedure discussed in Example 1.

Figure 6:
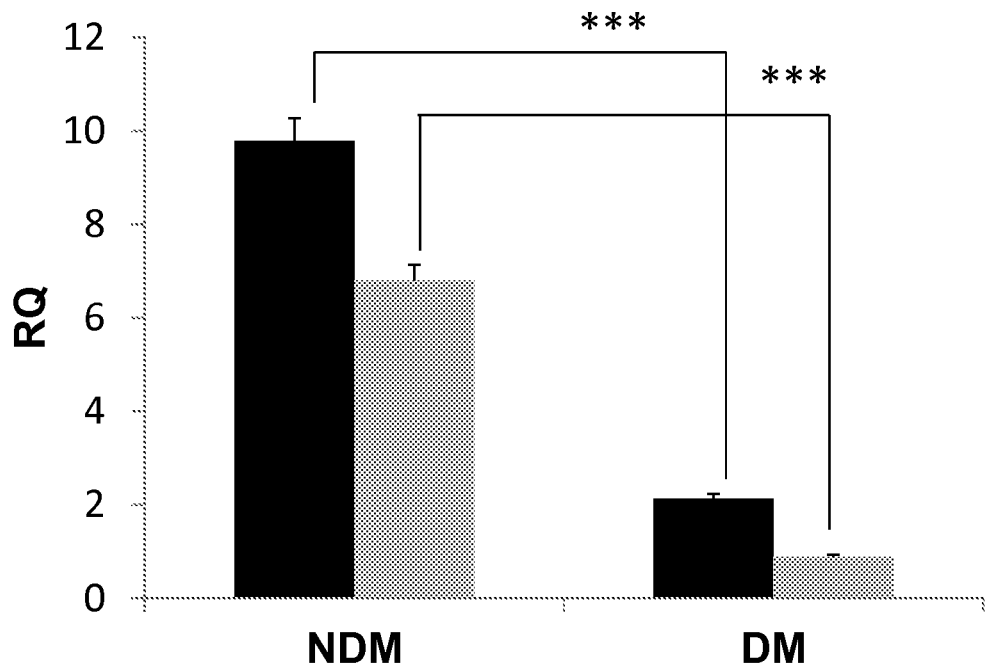
FIG. 6 shows a graph demonstrating the absolute transcript levels of Gas 5 lncRNA secreted by adipocytes derived from normal (non-diabetic), lean (lean-NDM), or lean diabetic (Lean-DM) patients. n=3.

Results:

Real-Time qPCR results for Gas5 expression are demonstrated in FIG. 6. Gas5 lncRNA expression was decreased in adipose tissue obtained from lean diabetic patients as compared to lean non-diabetic patients. Secretion of Gas5 lncRNA by adipocytes was decreased (as measured by presence in conditioned media) in adipocytes obtained from lean diabetics as compared to adipocytes obtained from lean non-diabetics.

Example 4: Effect of Gas5 Depletion in Lean Adipocytes

As diabetic subjects showed a decrease in Gas5 levels, the effect of depleting Gas5 from normal (non-diabetic) adipocytes was evaluated.

Methods:

Gas5 siRNA (10 nM, Ambion #332778; scrambled siRNA as a control) was transfected in lean adipocytes (Nucleofactor, Amaxa program A-033) for about 24 h. After 24 h, Gas5 levels were analyzed using the real-time qPCR assay as described in Example 1. Glut4 PPARγ, adiponectin, and leptin mRNA expression was also analyzed using real-time qPCR. The adiponectin forward primer is 5' AGATCTTGGTAAAGCGAATG 3' (SEQ ID NO: 5). The adiponectin reverse primer is 5' TGGTGAGAAGGGTGAGAA 3' (SEQ ID NO: 6). The leptin forward primer is 5' CCTTCCAGAAACGTGATCCAA 3' (SEQ ID NO: 7). The leptin reverse primer is 5' GGCCAGCACGTGAAGAAGAT 3' (SEQ ID NO: 8). Further, the leptin to adiponectin (leptin:adiponectin) ratio (LAR) was measured in conditioned media collected from the adipocytes transfected with Gas5 siRNA or control siRNA.

Figure 7:
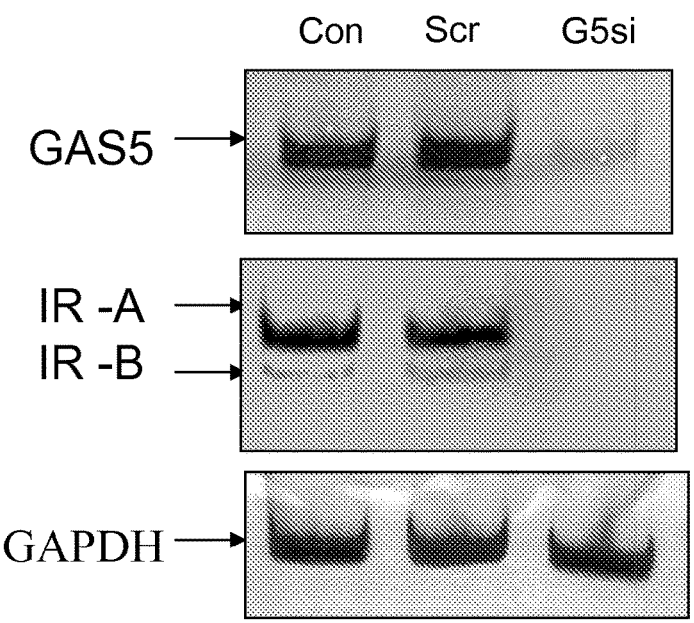
FIG. 7 shows gel images of PCR products demonstrating the effect of Gas5 siRNA treatment on Gas5, insulin receptor A, and insulin receptor B gene expression in non-diabetic (NDM) adipocytes.
Figure 8:
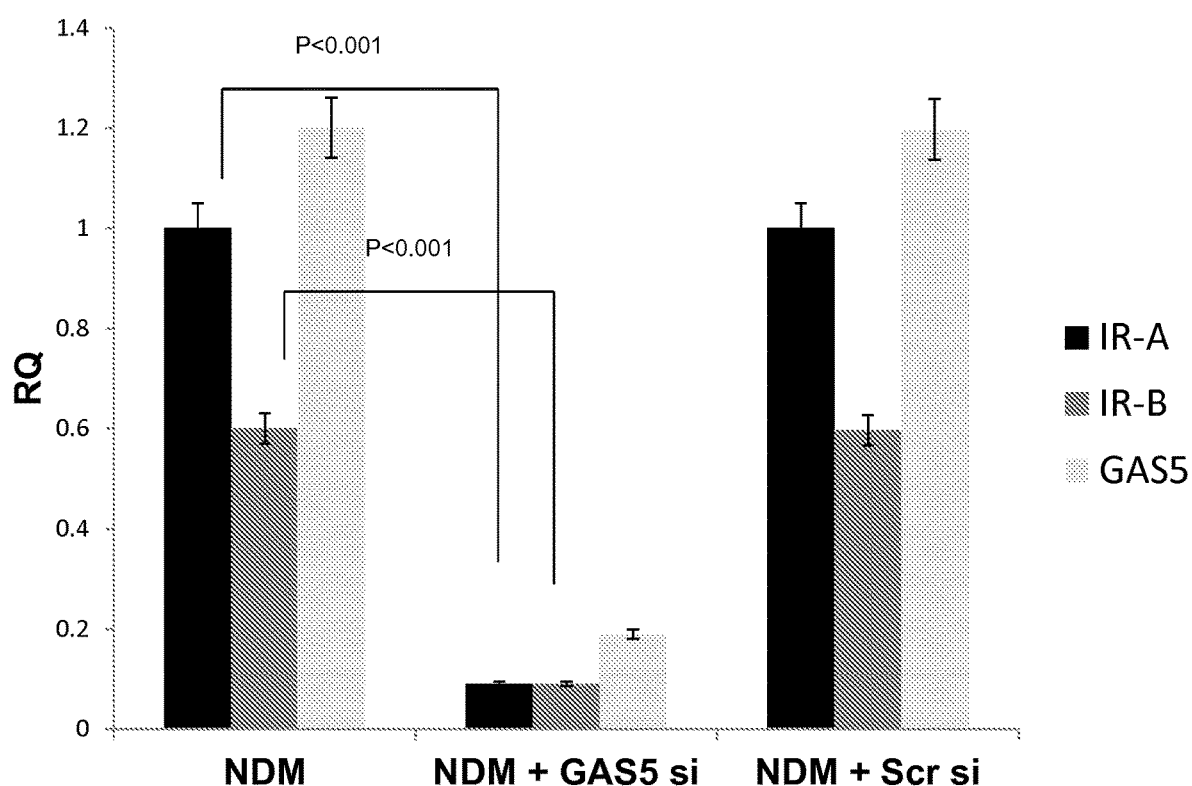
FIG. 8 shows a graph demonstrating the effect of Gas5 siRNA treatment on Gas5, insulin receptor A, and insulin receptor B gene expression as determined by Real-Time qPCR in adipocytes from non-diabetics.
Figure 9:
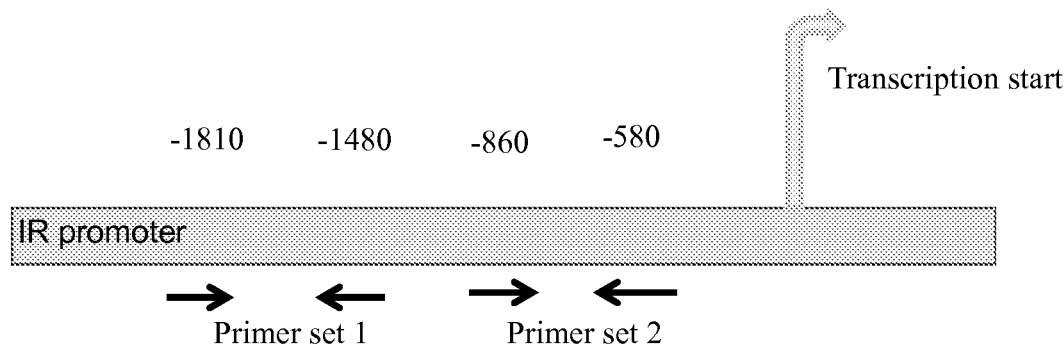
FIG. 9 shows a map of the insulin receptor promoter region demonstrating approximate location of two primer sets.
Figure 10A:
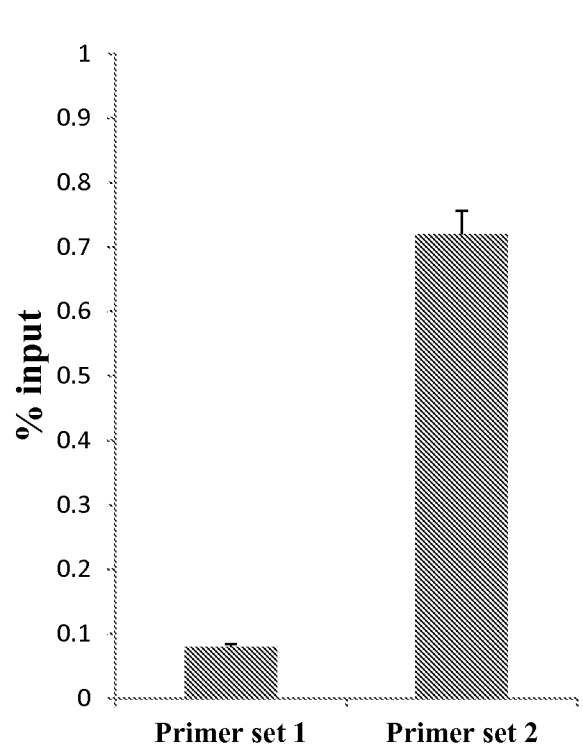
FIGS. 10A-10B show graphs showing data from an RNA immunoprecipitation assay demonstrating Gas5 complex formation with the c-terminal domain of RNA polymerase II and insulin receptor promoter between region −580 and −860 simultaneously.
Figure 10B:
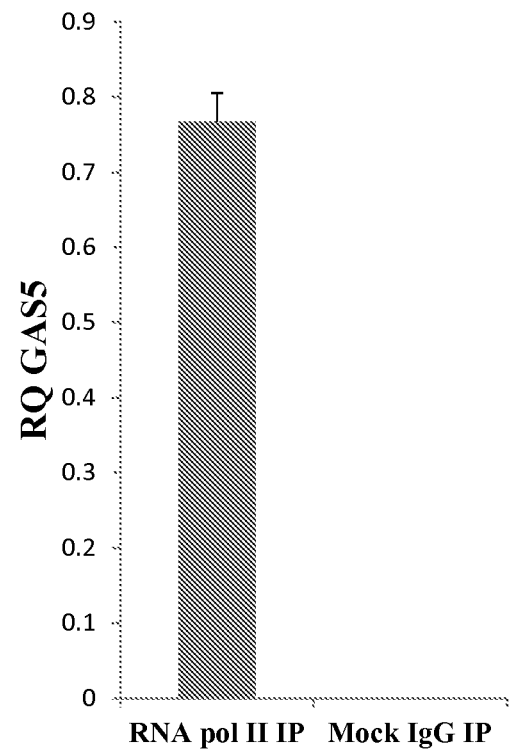
Figure 11:
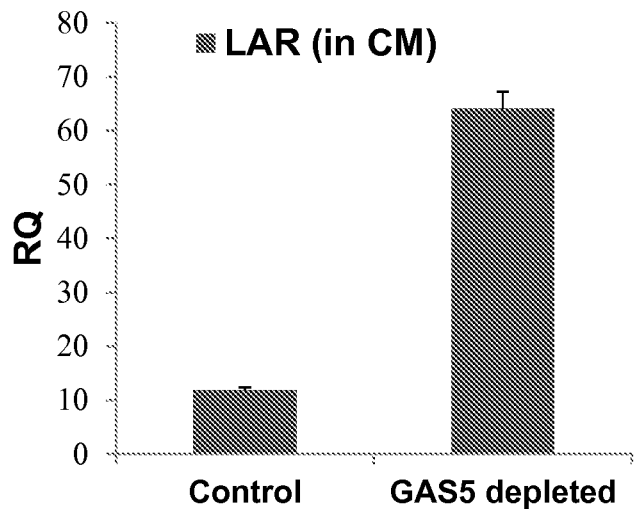
FIG. 11 shows a graph demonstrating the leptin to adiponectin RNA transcript ratio (LAR) in conditioned media (CM) from non-diabetic adipocytes transfected with Gas5 siRNA.

Results:

Depletion of Gas5 levels dramatically inhibited expression of the insulin receptors A and B as shown in FIGS. 7-8. A computational analysis (LaserGene) showed that the sequence "aacgttttat" on Gas5 DNA binding domain is 100% complementary to a sequence on promoter region (at −826 bp) of insulin receptor (IR). This suggests that Gas5 binds to IR by Watson-Crick base-pairing. Data from RNA-immunoprecipitation demonstrated that Gas5 forms a complex with the C-terminal domain (CTD) of RNA polymerase II as shown in FIGS. 9 and 10A-10B. The combined data suggests that Gas5 acts as a rioboactivator and promotes transcription of insulin receptor by sequestering RNA polymerase II to promote IR transcription. The graph represents four experiments. FIG. 11 shows the effect of Gas5 depletion (as induced by Gas5 siRNA) on the leptin:adiponectin ratio (LAR) in the secretome. FIG. 11 shows the results from experiments repeated three times. Depletion of Gas5 resulted in a reduction of IR transcript levels and a high LAR (a marker of metabolic syndrome). These results suggest that Gas5 expression levels have direct effects on targets contributing to diabetes and metabolic syndrome (e.g. Insulin Receptors A and B).

Example 5: Effect of Gas5 Depletion on Glucose Uptake by Lean Adipocytes

Methods:

To determine the effect of Gas5 depletion on glucose uptake by lean adipocytes, Gas5 siRNA was transfected in adipocytes as described in Example 4. After transfection, cells were serum starved and insulin (100 nM) was added to cells. Cells were incubated in the insulin for about 30 min. After incubation [3-H]-deoxy-2D-glucose up-take in Gas5 depleted adipocytes was measured. [3-H]-deoxy-2D-glucose uptake was measured in cpm (counts per million). The experiment was preformed three times.

Figure 12:
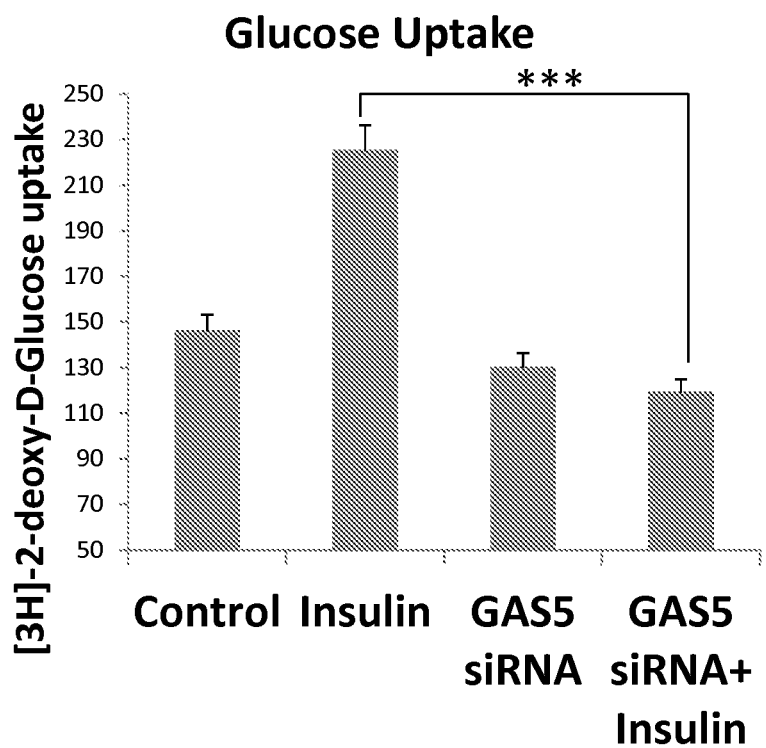
FIG. 12 shows a graph demonstrating [3-H]-deoxy-2-D-Glucose uptake in Gas5-depleted non-diabetic adipocytes. ** $P<0.01$.

Results:

GLUT1 and GLUT4 are insulin-responsive glucose transporter expressed in adipocytes. Insulin upon binding to its receptors can induce translocation of glucose transporters to the plasma membrane thereby increasing glucose uptake. Results from the glucose uptake study in Gas5-depleted lean adipocytes are demonstrated in FIG. 12. As demonstrated in FIG. 5, Gas5 depletion in lean adipocytes resulted in a decrease in insulin mediated glucose uptake in lean adipocytes. Insofar as Gas5 depletion was observed to affect multiple insulin-responsive genes related to glucose metabolism (Example 4) and insulin-mediated glucose uptake (possibly by GLUT4), Gas5 may play a role in glucose metabolism and homeostasis. Thus, altered Gas5 expression may play a role in the pathology of diabetes and metabolic syndrome.

Example 6: Gas5 is Expressed in Adipocytes and Secreted in Exosomes in Conditioned Media (CM)

Methods: Adipose Samples:

White adipose tissue was obtained as discarded tissue from bariatric surgeries. The subcutaneous and omental depots were collected from the same subject. The lean samples were obtained from a female donor with BMI of 21.3 and the obese samples were from a female donor with BMI of 54.6. Both subjects were non-diabetic, non-smokers. The de-identified samples were obtained under an Institutional Review Board approved protocol and was transported to the laboratory and processed within 24 h of receipt.

Adipose-Derived Stem Cells:

ADSC were isolated as previously described (Watson J E, Patel N A, et al. Adv Wound Care (New Rochelle). 2014; 3(3):219-28). Briefly, adipose tissue was cut up into small pieces and digested with 0.075% collagenase Type 1 (Worthington) in modified PBS for 2 h at 37° C. The digestion was stopped by adding a-MEM+20% heat-inactivated FBS. The suspension was filtered and centrifuged at 400 g at room temperature. The pellet contains the stromal vascular fraction (SVF). The pellet was resuspended in 1 mL of the erythrocyte lysis buffer (Stem Cell Technologies) for 10 min and washed in 20 mL of PBS with 2% P/S/A before centrifugation, 300-500 g, 5 min. The supernatant was aspirated and the cell pellet resuspended in a 3 mL stromal medium (α-MEM; Mediatech) with 20% FBS, 1% 1-glutamine (Mediatech), 1% P/S/A. Following three rinses in the stromal medium, SVF cells were plated for initial cell culture at 37° C. with 5% C02 in ADSC medium from ZenBio™ (Cat # PM-1). Subconfluent cells were passaged by trypsinization. Experiments were conducted within passages 2-3. In addition, ADSC were also obtained from ZenBio™ to validate reproducibility (commercially available exempt cell lines). ZenBio ADSCs from lean donor was female with BMI of 21.1 and obese donor was female with BMI of 49.8.

Figure 14:
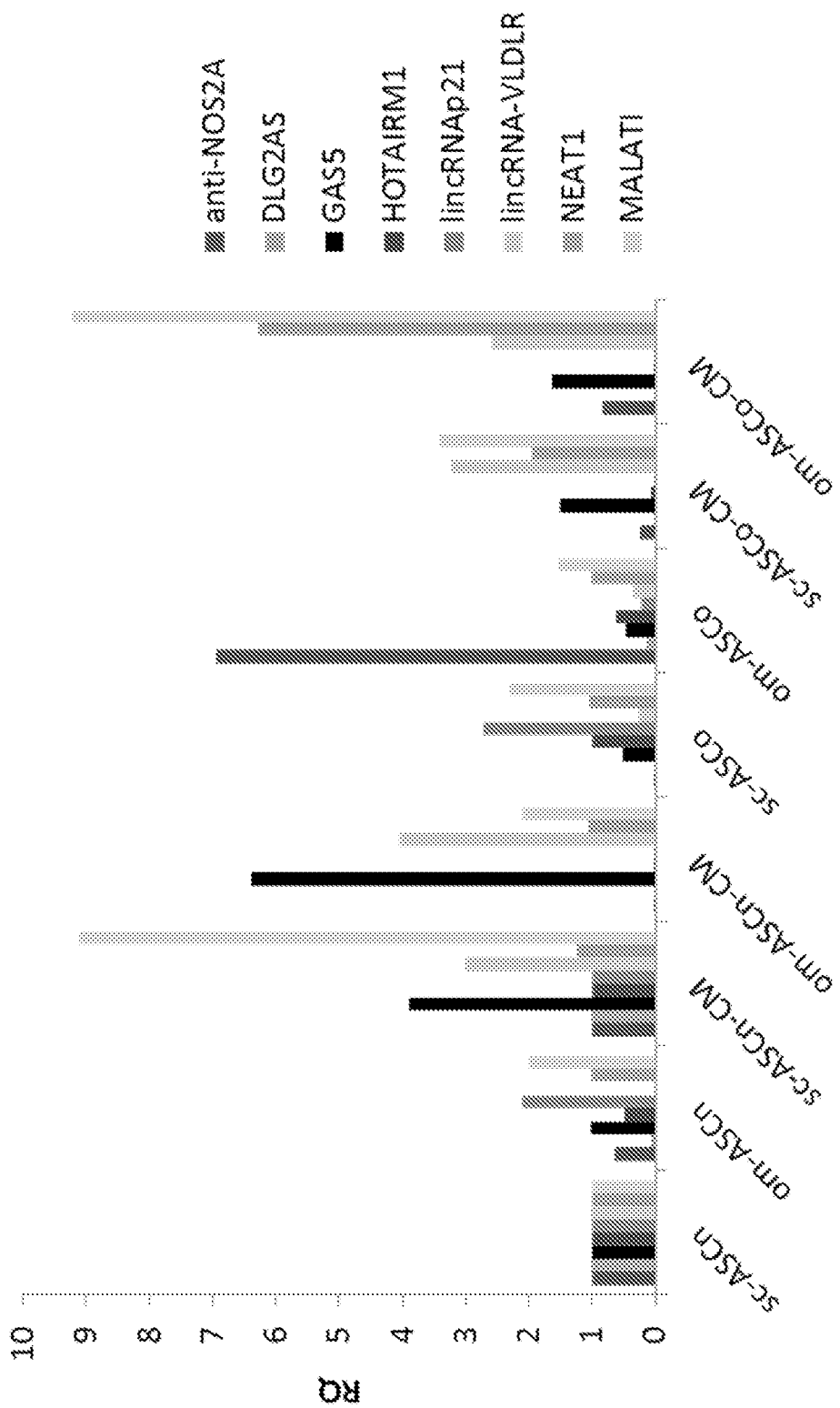
FIG. 14 shows a graph demonstrating the expression (relative quantification (RQ)) of anti-NOS2A, DLG2AS, GAS5, HOTAIRM1, lincRNAp21, lincRNA-VLDLR, NEAT1 and MALAT1, detected in the secretome of various adipose stem cells and its secretome (collected as conditioned media—CM) (x-axis). Expression of the various lncRNAs were measured using real-time qPCR on total RNA isolated from sc-ASCn, om-ASCn, sc-ASCo and om-ASCo and its respective conditioned media. The experiment was independently repeated five times with similar results.

Exosome Isolation:

The four adipose stem cells subcutaneous normal ADSC (sc-ADSCn), omental normal ADSC (om-ADSCn), subcutaneous obese ADSC (sc-ADSCo) and omental obese ADSC (om-ADSCo) were grown to confluency and medium replaced with serum-free defined medium, the mesenchymal stem cell basal medium (MSC-BM-CD from Lonza #00190620). Conditioned media (CM) was collected after 48 h. FIG. 14 shows lncRNAs expression in the four ADSC and its conditioned media (the fig demonstrates that subq and omental adipose depots have different lncRNA signatures; more lncRNAs are detected in whole CM compared to those packaged specifically in exosomes) FIG. 14 shows GAS5 is secreted with higher levels seen in CM compared to cells. Further, obese ADSC have lower levels of GAS5 on CM compared to lean. CM is further processed to purify the smallest of microvesicles-exosomes. CM is centrifuged at 3000 g for 15 min to remove dead cells. ExoQuick™ (SBI) reagent was added to the CM and incubated overnight at 4° C. Following centrifugation at 1500 g for 30 min, the pellet was further processed. ExoCap™ (JSR Life Sciences) composite reagent containing magnetic beads for CD9, CD63 and CD81 was used to purify exosomes. Exosomes were eluted from beads using the manufacturers elution buffer and used in western blot analysis or in qPCR.

Results: lncRNA Content of ADSC Exosomes:

Long noncoding RNAs (lncRNAs) are important regulators of gene expression and epigenetic regulation and are packaged in exosomes to prevent degradation. Long noncoding RNAs secreted by adipocytes in their exosomes was evaluated. Using an lncRNA array (SABiosciences) a spectrum of lncRNAs within the ADSC and its secretome measured in the conditioned media was evaluated. The ADSC were obtained from either subcutaneous (sc-ADSC) or omental depot (om-ADSC) from the same individual. Total RNA from ADSC, conditioned media or from exosomes from was isolated. The analysis included only those lncRNAs which were consistently observed and were statistically significant (anti-NOS2a, GAS5, DLG2A5, HOTAIRM1, lincRNAP21, lincRNA-VLDL, MALAT1).

Figure 13:
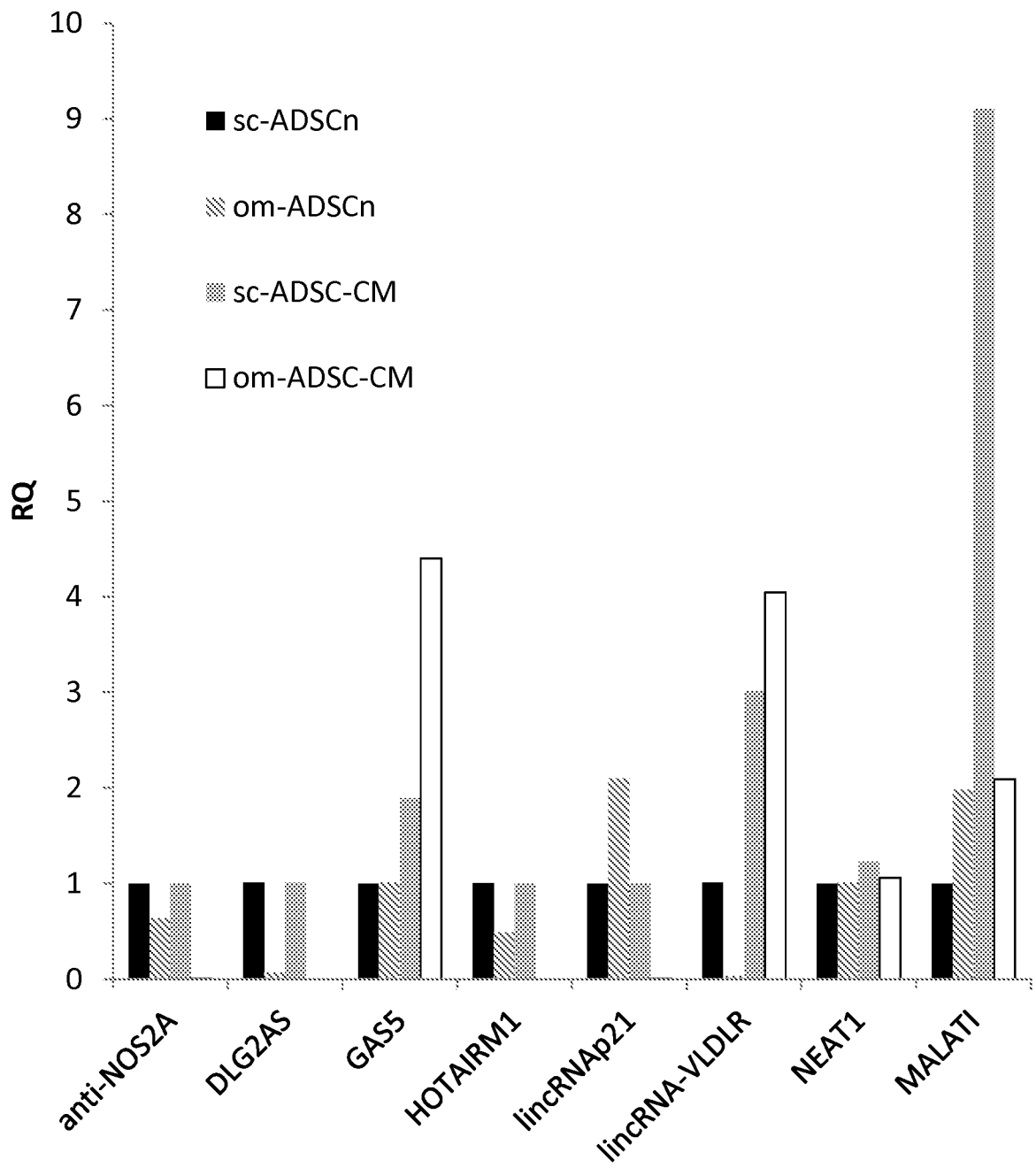
FIG. 13 shows a graph demonstrating the expression (relative quantification (RQ)) of anti-NOS2A, DLG2AS, GAS5, HOTAIRM1, lincRNAp21, lincRNA-VLDLR, NEAT1 and MALAT1 (x-axis) detected in the secretome of various adipose stem cells and its secretome (collected as conditioned media—CM) (sc-ASCn, om-ASCn, sc-ASCo and om-ASCo).

Results:

The results (FIGS. 13-14) indicated that the lncRNAs expression levels were different between sc-ADSC and om-ADSC with incRNAp21 and MALAT1 present in higher levels in om-ADSC. The expression of lncRNAs in the secretome (measured in conditioned media) was measured and it was observed that anti-NOS2a, GAS5, DLG2A5, HOTAIRM1, lincRNAp21, lincRNA-VLDLR, MALAT1 are significantly present at higher concentration in the CM of sc-ADSC. Greater amounts of GAS5, lincRNA-VLDLR, MALAT1 in the conditioned medium (CM) compared to the corresponding cells was detected.

I claim:

1. A method comprising:
   obtaining a blood serum sample from a non-obese subject;
   detecting an amount of GAS5 lncRNA present in the blood serum sample lower than 10 ng/µl by contacting the blood serum sample with one or more polynucleotides capable of specifically binding GAS5 lncRNA.

2. The method of claim 1, wherein the subject has not been diagnosed with diabetes.

3. The method of claim 1, wherein the GAS5 lncRNA has a sequence that is 80%-100% identical to SEQ ID NO: 12.

4. The method of claim 1, wherein the step of detecting the amount of GAS5 lncRNA present in the blood serum sample is performed using a method comprising a technique selected from the group consisting of: a microarray polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing, cell-based RNA detection assays, in situ hybridization, northern blot analysis, and combinations thereof.

5. The method of claim 1, wherein the one or more polynucleotides is selected from the group consisting of SEQ ID NO: 1-2.

* * * * *